(12) United States Patent
Ouyang et al.

(10) Patent No.: US 12,320,731 B2
(45) Date of Patent: Jun. 3, 2025

(54) PLATFORM-INDEPENDENT MOBILE ENVIRONMENTAL SENSING SYSTEM

(71) Applicant: FLORIDA ATLANTIC UNIVERSITY BOARD OF TRUSTEES, Boca Raton, FL (US)

(72) Inventors: Bing Ouyang, Boca Raton, FL (US); Paul Wills, Boca Raton, FL (US); Casey Den Ouden, Boca Raton, FL (US); Lucas Lopes, Boca Raton, FL (US); William Fairman, Miami, FL (US)

(73) Assignee: FLORIDA ATLANTIC UNIVERSITY BOARD OF TRUSTEES, Boca Raton, FL (US)

( * ) Notice: Subject to any disclaimer, the term of this patent is extended or adjusted under 35 U.S.C. 154(b) by 0 days.

(21) Appl. No.: 18/839,209

(22) PCT Filed: Dec. 19, 2022

(86) PCT No.: PCT/US2022/053371
§ 371 (c)(1),
(2) Date: Aug. 16, 2024

(87) PCT Pub. No.: WO2023/158489
PCT Pub. Date: Aug. 24, 2023

(65) Prior Publication Data
US 2025/0110025 A1    Apr. 3, 2025

Related U.S. Application Data

(60) Provisional application No. 63/311,937, filed on Feb. 18, 2022.

(51) Int. Cl.
*G01N 1/16* (2006.01)
*G01N 33/18* (2006.01)

(52) U.S. Cl.
CPC ........... *G01N 1/16* (2013.01); *G01N 33/1886* (2013.01)

(58) Field of Classification Search
CPC ................. G01N 1/16; G01N 33/1886; G01N 2001/1031
(Continued)

(56) References Cited

U.S. PATENT DOCUMENTS 11,150,658 B2    10/2021   Ouyang et al.
2019/0166765 A1   6/2019   Maor
(Continued)

FOREIGN PATENT DOCUMENTS

WO    2013131882 A2    9/2013

OTHER PUBLICATIONS

Y. Li, W. Liu, Y. Deng, W. Hong and H. Yu, "Miuraori enabled stretchable circuit boards," Nature Partner Journals—Flexible Electronics, 2021.
(Continued)

*Primary Examiner* — Robert R Raevis
(74) *Attorney, Agent, or Firm* — Meunier Carlin & Curfman LLC

(57) ABSTRACT

An exemplary platform independent sensing platform system and method that streamline the sensing operations of unmanned aerial-amphibious vehicles for remote or wide area analysis and/or monitoring of a body of water. The exemplary sensing platform system and method employ a remote sensing payload that wirelessly tethers to an edge sensing platform to operate synchronously with one another as the remote sensing payload samples a body of water at different depths and at different locations while being deployed and extracted from a given different locations by the unmanned aerial-amphibious vehicle.

20 Claims, 27 Drawing Sheets

(58) Field of Classification Search
USPC .............. 73/64.56, 863, 863.01, 864, 864.31, 73/864.34; 702/22, 30, 127
See application file for complete search history.

(56) References Cited

U.S. PATENT DOCUMENTS

| | | |
|---|---|---|
| 2021/0064034 A1 | 3/2021 | Ouyang et al. |
| 2021/0068909 A1 | 3/2021 | Eyre et al. |
| 2022/0242561 A1 | 8/2022 | Marion |

OTHER PUBLICATIONS

Z. Song, Studies of Origami and Kirigami and Their Applications, Arizona State University, 2016.

M. Wooten, "UGA researchers unfold advances in cardiac catheters," UGA Research, Jul. 28, 2016. https://research.uga.edu/news/uga-researchers-unfold-advances-in-cardiac-catheters/.

"From Origami to a Prototype Stent," MDDI, Apr. 27, 2012.

K. Miura and T. Tachi, "Synthesis of rigid-foldable cylindrical polyhedra," Gmuend, Austria, 2010.

A. A. Deleo, J. E. O'Neil, H. Yasuda, J. Yang and M. Salviato, "Composite Origami: Foldable Structures Based on Tachi-Miura-Polyhedron Origami Technique," 2018.

S. A. Zirbel, B. P. Trease, S. P. Magleby and L. L. Howell, "Deployment Methods for an Origami-Inspired Rigid-Foldable Array," in 40th Aerospace Mechanisms Symposium, Greenbelt, Maryland, 2014.

T. Tachi, "Rigid-Foldable Thick Origami," 2011.

T. Tachi, "Geometric Considerations for the Design of Rigid Origami Structures," in International Association for Shell and Spatial Structures, Shanghai, China, 2010.

M. Schenk and S. D. Guest, "Geometry of Miura-folded metamaterials," PNAS, vol. 10, No. 9, pp. 3276-3281, 2013.

H. Yasuda, T. Yein, T. Tachi, K. Miura and M. Taya, "Folding behaviour of Tachi-Miura polyhedron bellows," Royal Society, pp. 1-18, 2013.

Y. Nishiyama, "Miura Folding: Applying Origami to Space Exploration," International Journal of Pure and Applied Mathematics, vol. 79, No. 2, pp. 269-279, 2012.

J. J. Park, P. Won and S. H. Ko, "Review on Hierarchical Origami and Kirigami Structure for Engineering Applications," International Journal of Precision Engineering and Manufacturing—Green Technology, vol. 6, pp. 147-161, 2019.

S. Chen, J. Chen, X. Zhang, Z.-Y. Li and J. Li, "Kirigami/origami: unfolding the new regime of advanced 3D microfabrication/nanofabrication with "folding"," CIOMP, vol. 9, No. 75, pp. 1-19, 2020.

T. van Manen, S. Janbaz, M. Ganjian and A. A. Zadpoor, "Kirigami-enabled self-folding origami," Materials Today, vol. 32, pp. 59-67, 2020.

A. Reid, F. Lechenault, S. Rica and M. Adda-Bedia, "Geometry and design of origami bellows with tunable response," 2016.

K. Saito, A. Tsukahara and Y. Okabe, "Designing of self-deploying origami structures using geometrically misaligned crease patterns," Royal Society, pp. 1-16, 2015.

N. Turner, B. Goodwine and M. Sen, "A review of origami applications in mechanical engineering," Institution of Mechanical Engineers, vol. 230, pp. 2345-2362, 2016.

S.J. Kim, D.Y. Lee, G.P. Jung, K.J. Cho, "An origami-inspired, self-locking robotic arm that can be folded flat," Science Robotics, vol. 3, pp. 1-10.

International Search Report and Written Opinion issued in PCT/US2022/053371, mailed Jun. 1, 2023.

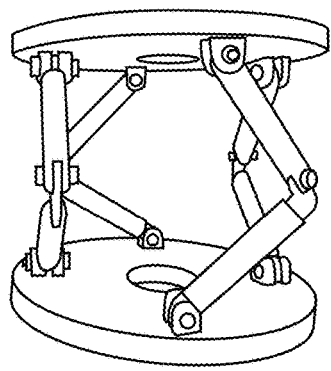 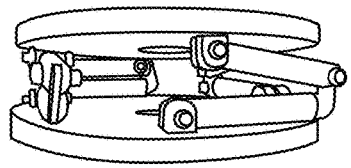 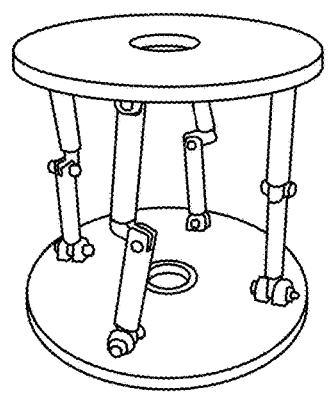
FIG. 11A   FIG. 11B   FIG. 11C
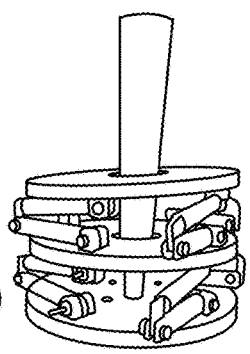 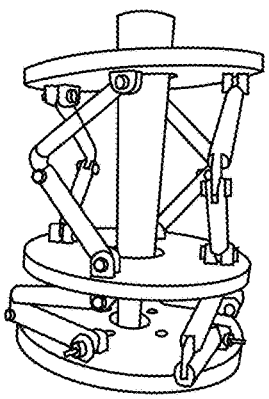
FIG. 11D   FIG. 11E
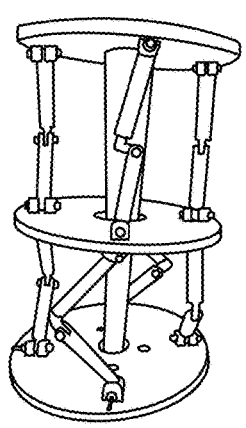 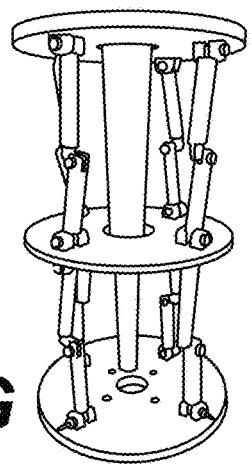
FIG. 11F   FIG. 11G

PLATFORM-INDEPENDENT MOBILE ENVIRONMENTAL SENSING SYSTEM

STATEMENT REGARDING FEDERALLY SPONSORED RESEARCH OR DEVELOPMENT

This invention was made with government support under Contract No. 2019-67022-29204 awarded by the National Institute of Food and Agriculture/USDA. The government has certain rights in the invention.

BACKGROUND

There is a commercial interest in monitoring bodies of water and industrial production, such as aquaculture farms, for safety monitoring, quality management, and to understand changing or dangerous conditions in such waters.

Aquaculture farming, or fish farming, plays an important role in securing food safety in the United States and around the world. Since 2014, more farmed fish than wild-caught fish have been consumed globally, and half of all seafood comes from farms. However, for fish farming to be sustainable and economically viable, drastic improvements to current labor-intensive and resource-inefficient operations are required.

Lakes, rivers, and streams are critical water infrastructure in the United States and are continually subjected to changes due to natural factors as well as industrial output into them.

Monitoring bodies of water can be challenging due to the wide area of interest and the complex nature of the analysis. Pond buoy sensing systems are static and thus expensive to implement across multiple locations, and truck-mounted sensing platforms do not allow for the monitoring of water beyond their edges. While waterproof drones are commercially available, the use of such drones in monitoring such bodies of water by directly sampling them is nevertheless also challenging as the drones are not designed as sensing platforms to carry such payloads and measuring data in an open body of water poses technical challenge associated with flowing water.

SUMMARY

An exemplary platform independent sensing platform system and method are disclosed that streamline the sensing operations of unmanned aerial-amphibious vehicles for remote or wide area analysis and/or monitoring of a body of water. The exemplary sensing platform system and method employ a remote sensing payload that wirelessly tethers to an edge sensing platform to operate synchronously with one another as the remote sensing payload samples a body of water at different depths and at different locations while being deployed and extracted from a given different location by the unmanned aerial-amphibious vehicle.

The exemplary system is beneficially platform-neutral from a sensing perspective and data perspective. That is, the system is re-configurable to be equipped with a host of sensors of interest for a given sensing application. Examples include inertial measurement units ("IMUs"), barometers, temperature sensors, humidity sensors, wind speed sensors, wind direction sensors, rain sensors, solar radiation sensors, water pollution sensors, water contaminant sensors, water level sensors, turbidity sensors, pH sensors, fungus detectors, parasite detectors, biological oxygen demand sensors, oxidation-reduction potential sensors, colored dissolved organic matter sensors, salinity/conductivity sensors, cameras (e.g., digital, hyperspectral, etc.), a microphone, spectrographic sensors, chlorophyll sensor, vibration sensors, dissolved oxygen concentration sensor, various chemical concentration sensors, among others described herein. The system can interface with a cloud infrastructure and/or internet-of-things infrastructure to aggregate data from a variety of sensing platforms to provide a wholistic view of a given body of water.

In some embodiments, the exemplary unmanned aerial-amphibious vehicle system is configured with a sensor payload to measure water vertical distribution, e.g., depth versus temperature and dissolved oxygen, to allow for the measurement of pond temperature stratification and determine potentially dangerous conditions, e.g., that can cause dissolved oxygen (DO) depletion.

The exemplary unmanned aerial-amphibious vehicle may be equipped with a robust winch system that can automatically fold during flight by turning downward for payload release during sensing and folding back up after sensing. The winch system may be optimized to operate via a single actuator to minimize weight, perform the remote sensor release and capture, and extend the remote sensor into the body of water.

In an aspect, a method is disclosed for operating a system for water sampling or collection at a wastewater site, a body of water, or an aquaculture farm, the method comprising positioning a sensing platform (terrestrial, or aero-amphibious, or fixed location system) over or next to a water body medium in a sampling or collecting operation, wherein the sensing platform comprises an elongated or elongate-able structure that can extend or hinge-ably move to a first position to put a remote sensor connected to the sensing platform by the elongated or elongate-able structure into the water body medium for water collection or sampling; transmitting, over a wireless communication channel, a wireless command signal from a first controller located on the sensing platform to the second controller located in the remote sensor, wherein the second controller located in the remote sensor is fully autonomous and is not electrically connected by wire to the first controller; executing, at the second controller, a set of instruction for a sensing or collection protocol to perform a sensing or collection operation at the remote sensor; concurrent with the execution of the set of instruction for the sensing or collection protocol, adjusting at the sensing platform the remote sensor from the first position to a plurality of positions, including a second position and a third position, each corresponding to a different water depth to perform the sensing or collection operation of the remote sensor at the respective water depth; wherein the sensing or collection protocol for the sampling or collecting operation is synchronized to the plurality of positions corresponding to a pre-defined water depth.

In some embodiments, the sensing platform is configured to adjust the remote sensor to the plurality of positions at pre-defined time intervals defined in the set of instructions for the sensing or collection protocol, and recordation of measurements by the second controller of the remote sensor is performed according to the pre-defined time intervals, wherein initialization of the pre-defined time intervals is based on the wireless command signal.

In some embodiments, the sensing platform comprises an aero-amphibious vehicle comprising a winch assembly and the remote sensor, wherein the aero-amphibious vehicle is configured to perform the sensing or collection operation at a plurality of locations, and wherein the winch assembly is configured to i) release the remote sensor from a stowed position to a deployed position and ii) draw the remote sensor from the deployed position to the stowed position in between each of the sensing or collection operations at the plurality of locations.

In some embodiments, the release of the remote sensor from a stowed position to a deployed position and the draw of the remote sensor from the deployed position to the stowed position is performed by actuation of the winch assembly to extend or retract a tether connecting to the remote sensor, the winch assembly comprising a retaining arm subassembly (i) through which the tether connects to the remote sensor and (ii) that which moves (a) from a stowed position to a deployed position when the winch assembly extends the tether to release the remote sensor from the retaining arm subassembly and (b) from the deployed position to the stowed position when the winch assembly retracts the tether to engage the remote sensor with the retaining arm subassembly.

In some embodiments, the sensing platform comprises a terrestrial vehicle.

In some embodiments, the sensing platform comprises an aero-amphibious vehicle.

In some embodiments, the sensing platform comprises a fixed location system.

In another aspect, a sensing platform system (terrestrial, aero-amphibious, or fixed location system) is disclosed comprising a processor; and a memory having instructions stored thereon, wherein execution of the instructions by the processor causes the processor to perform any one of the above-discussed methods.

In another aspect, a winch payload deployment assembly apparatus (e.g., for attachment to an aero-amphibious vehicle) is disclosed comprising a winch chassis comprising a spool, an actuator, and a coupling between the spool and the actuator; a tether configured to be wound around the spool, the tether being fixably attached to the winch chassis at a first end a payload at a second end; and a bracket coupled to the winch chassis, wherein the bracket is configured to move between a stowed position to a deployed position when the spool actuates from an initial position to an extended position to release the payload abutting against the bracket, and wherein the bracket is configured to move from the deployed position to the stowed position when the spool actuates from the extended position to the initial position to draw the payload to abut against the bracket.

In some embodiments, the bracket is biased by a torsional spring towards the deployed position.

In some embodiments, the bracket comprises an angled body having (i) a retaining portion configured to abut against a spool plate (that guides the tether from the spool) and (ii) a payload portion configured to support the payload when the bracket is in the stowed position, wherein the retaining portion abuts against the spool plate when the spool is in the initial position.

In some embodiments, the initial position is the most retracted position of the spool.

In some embodiments, the actuator actuates to unwound the spool from the initial position, the extension of the tether releasing the payload abutting against the bracket to allow the bracket to move from the stowed position to the deployed position.

In some embodiments, the winch payload deployment assembly apparatus further includes a second actuator to actuate the bracket.

In some embodiments, the winch payload deployment assembly apparatus further includes a contact sensor (e.g., Hall effect sensor) configured to detect when the bracket is in the stowed position, the contact sensor providing a signal to control the actuation of the spool (e.g., stop the actuation of the pool drawing of the remote sensor to the stowed position).

In some embodiments, the payload comprises waterproof housing.

In some embodiments, the winch chassis comprises a first side wall and a second side wall to fixably retain the spool, the actuator, and the bracket and couple the winch payload deployment assembly apparatus to a vehicle.

In some embodiments, the sensing platform comprises an aero-amphibious vehicle comprising a connection arm having a plurality of sections configured to be rotatable to move between a stowed configuration and a deployed configuration, to extend or extract the remote sensor into and out of the water body medium.

In some embodiments, the connection arm comprises a telescoping rod assembly that couples to the plurality of sections to move the plurality of sections between a stowed configuration and a deployed configuration.

In another aspect, a robotic sensing package is disclosed, including an undercarriage substrate disposed on a moving platform and a connection arm. The connection arm includes a first end operatively coupled to the moving platform, a second end removably coupled to a sensing module, a plurality of plates separated and spaced apart from each other, including a first and a second plate, and a plurality of sets of elongated links. The plurality of sets of elongated links includes a first set of links and a second set of links. The first set of links includes a first link hingeably connected to the first plate and a second link. The second link is hingeably connected to the second plate. Each of the first link and second link is rotatable to move the second plate between a stowed configuration and a deployed configuration.

In some implementations, the connection arm further includes a telescoping rod assembly having at least one telescoping section that is slidably coupled to the first plate. The at least one telescoping section extends through the first plate to connect to the second plate through a center hole in the first plate. Rotation of the telescoping rod assembly causes at least the second plate to rotate to move the second plate between the stowed configuration and the deployed configuration.

In some implementations, the connection arm further includes a telescoping rod assembly having a plurality of sections, including a first section and a second section. The first section is slidably coupled to the first plate. The second section is slidably coupled to the second plate. Rotation of the telescoping rod assembly causes the first plate and the second plate to rotate to move the second plate between the stowed configuration and the deployed configuration.

In some implementations, the first link has an L-shaped region at a connection point with the second link to facilitate rotation in one direction.

In some implementations, the first link and the second link can rotate up to 180 degrees with respect to each other.

In some implementations, the second plate is a distance apart from the first plate in the stowed configuration. The second plate is a second distance apart from the first plate in the deployed configuration, the second distance being defined by an angle of rotation of the telescoping rod assembly.

In some implementations, the connection arm further includes a gear assembly coupled between the undercarriage substrate and the telescoping rod assembly of the connection arm. The gear assembly engages with an actuator to move the second plate between the stowed configuration and the deployed configuration.

In some implementations, the sensing module includes at least a first wireless transmitter to wirelessly communicate a signal to a receiver distally located on the moving platform.

In some implementations, the sensor module includes a water contact sensor to determine when the sensing module is located within a liquid medium.

In some implementations, the moving platform is an aerial vehicle.

In some implementations, the moving platform is an unmanned ground vehicle.

In some implementations, the moving platform is an unmanned surface vehicle.

In some implementations, the moving platform is a manned vehicle or all-terrain vehicle.

In some implementations, the sensing modules include a temperature sensor.

In some implementations, the sensing modules include a pressure sensor.

In some implementations, the sensing modules include a dissolved oxygen sensor or other water quality sensor.

In another aspect, a method of remotely gathering samples from a liquid medium or making a direct measurement of the liquid medium is disclosed. The method includes: (i) deploying a mobile vehicle platform to a predefined geographic location over the liquid medium. The mobile vehicle platform includes an undercarriage substrate and a connection arm operatively coupled to the undercarriage substrate of the vehicle. The connection arm includes a first end operatively coupled to the moving platform, a second end removably coupled to a sensing module, a plurality of plates separated and spaced apart from each other, including a first plate, a second plate, and a third plate, a plurality of telescoping rod sections operatively coupled to a center hole of each plate, and a plurality of sets of elongated links, including a first set of links and a second set of links. The first set of links includes a first link hingeably connected to the first plate and a second link. The second link is hingably connected to the second plate. Each of the first link and second link is rotatable to move the second plate between a stowed configuration and a deployed configuration. (ii) activating an actuator located on the mobile vehicle platform. The activating causes an output of the actuator to drive the rotation of at least one of the plates or the telescoping rod sections, so to place a sensor module or sampling container located at the end of the connection arm into the liquid medium.

In some implementations, the method further includes: detecting a sensing signal to start a sampling operation, wherein the sampling operation continues for a predetermined period of time, stopping the motor for the duration of the sampling operation to collect sensor data, and starting the motor in an opposite direction so to remove the sensor module from the liquid medium and collapse the connection arm towards the stowed configuration.

In some implementations, the method further includes sending the sensor data from the sensing module to the mobile vehicle platform, and relaying the sensor data from the mobile vehicle platform to a central control center.

In some implementations, the liquid medium is a body of water.

In some implementations, the mobile vehicle platform is an aerial vehicle.

In some implementations, the gathered samples or direct measurements include dissolved oxygen, pressure, and/or temperature data.

In some implementations, the activating an actuator occurs upon the mobile vehicle platform reaching a predefined GPS location.

BRIEF DESCRIPTION OF DRAWINGS

The above aspects and other features, aspects, and advantages of the present disclosure will become better understood with regard to the following description, appended claims, and accompanying drawings in which:

FIG. 6H shows an example of a remote-sensing deployment operation of the waterproof aerial drone system conducted in the study.

FIGS. 11A-11G shows a progression of images of a connection arm in accordance with an illustrative embodiment.

DETAILED DESCRIPTION

Each and every feature described herein, and each and every combination of two or more of such features, is included within the scope of the present disclosure, provided that the features included in such a combination are not mutually inconsistent.

Example System

Figure 1A:
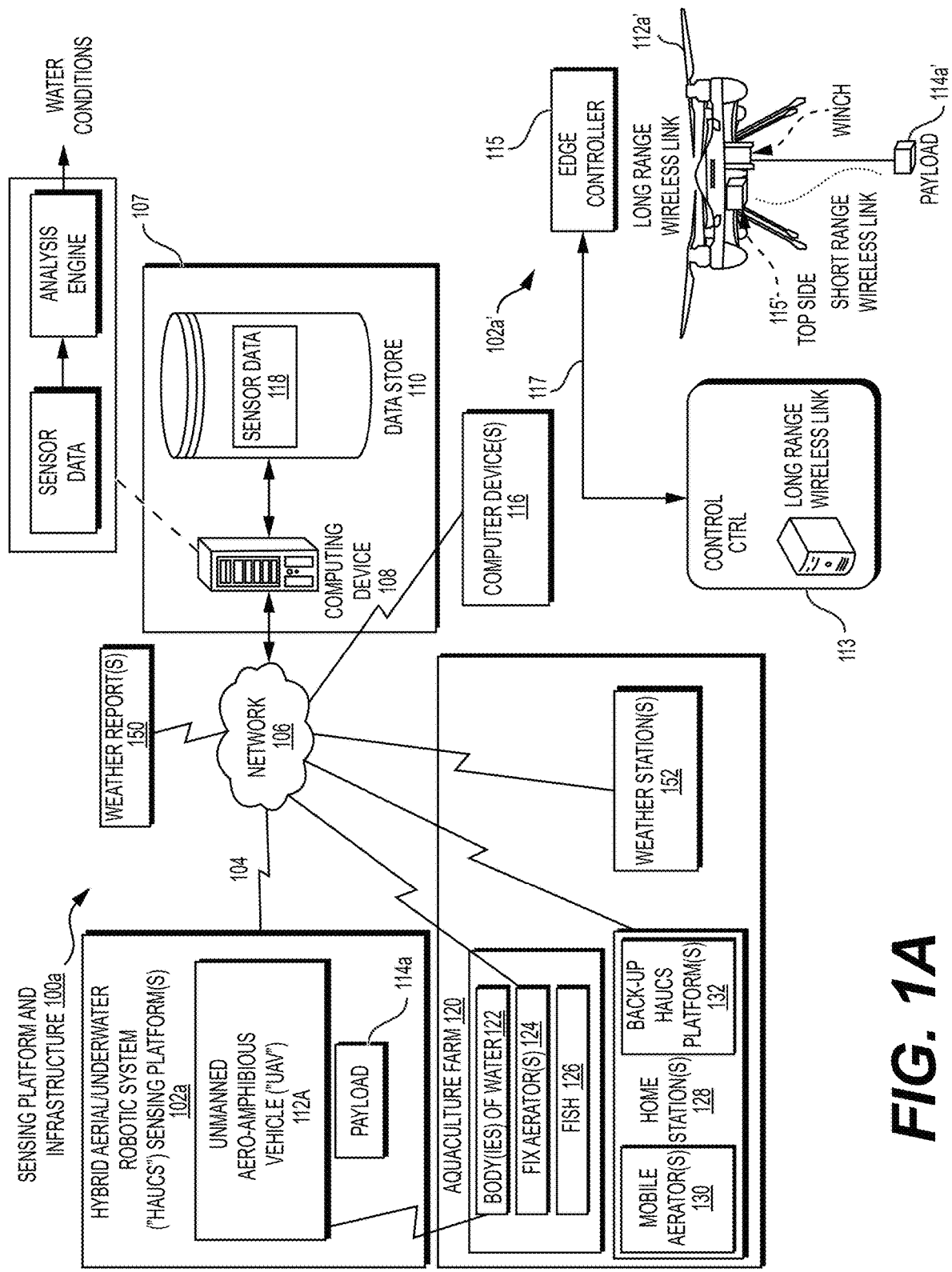
FIGS. 1A and 1B each shows an illustration of an example sensing platform system and infrastructure in accordance with an illustrative embodiment.
Figure 1B:
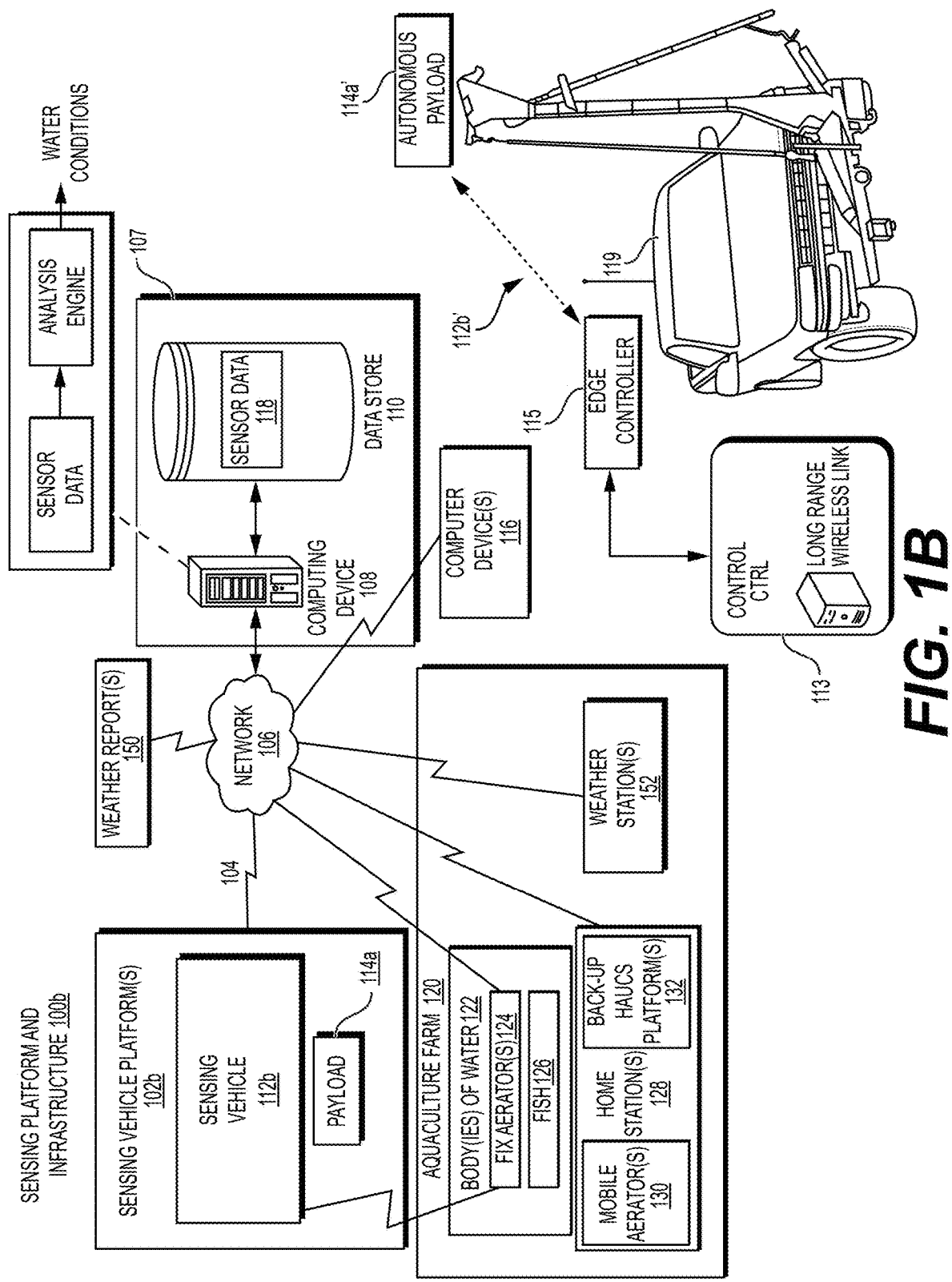

FIG. 1A and FIG. 1B each is an illustration of an example sensing platform system and infrastructure 100 (shown as 100a, 100b, respectively). In the example shown in FIG. 1A, System 100a includes at least one mobile sensing platform 102 (shown as "Hybrid Aerial/Underwater Robotic System ("HAUCS") Sensing Platform(s) 102a), static sensing platform 120 (shown as "Aquaculture Farm" 120), and cloud infrastructure and/or internet-of-things infrastructure 107. In the example shown in FIG. 1B, System 100b includes at least one mobile sensing platform 102 (shown as "Sensing Vehicle Platform(s) 102b), the static sensing platform 120, and the cloud infrastructure and/or internet-of-things infrastructure 107. In some embodiments, mobile sensing platforms 102a and 102b are employed in their combination within the system sensing platform system and infrastructure 100 to provide optimized use for the body of water monitoring and management.

The mobile sensing platform (e.g., 102a, 102b) facilitates improved aqua-culture farming, reduced water use, and pesticide use, improved water quality monitoring, and/or wetland assessment activities. For example, the sensing platform (e.g., 102a, 102b) can be used in agriculture fields to support precision agriculture initiatives designed to reduce water and pesticide use, in rivers to support water quality monitoring, and/or in swamps to support wetland assessment activities. In the scenario where the system (e.g., 100a, 100b) comprises two or more sensing platforms (e.g., 102a, 102b), operations of the sensing platforms (e.g., 102a, 102b) are coordinated to provide persistent, accurate and up-to-date situational awareness and to collaborate with human operators to accomplish water quality control. Each sensing platform (e.g., 102a, 102b) may be autonomously controlled and/or controlled remotely, in whole or in part, via a remote control operated by a human operator.

The aerial/amphibious sensing platform (e.g., 102a) is designed to be (1) power efficient so that it can cover multiple bodies of water on an hourly basis under all weather conditions, (2) relatively easy to maintain, (3) relatively inexpensive to manufacture, replace and/or repair, and/or (4) able to report sensor data to a centralized computing device(s) 108 associated with the cloud infrastructure and/or internet-of-things infrastructure 107 in real-time or almost real-time in all weather conditions. In the example shown in FIG. 1A, the sensing platform 102a includes a UAAV 112a that is operatively coupled to an autonomously operating payload 114 (shown as 114a) for sensing or sample collection. The UAAV 112a may include, but is not limited to, a Vertical Take-Off and Land ("VTOL") based drone, quad-copter, and/or a thrust vectoring coaxial drone. For example, the UAAV 112a comprises a coaxial-rotor-copter drone or coaxial drone that uses two contra-rotating rotors to compensate for each other's torque. Coaxial drones are well known in the art and, therefore, will not be described herein. Some of the known coaxial drones include a Sprite available from Ascent AeroSystems of Newtown, Conn.; a Navi drone available from Aeronavics of New Zealand; and a TDrone available from the Acceleration Technology Co. Ltd. of the Peoples Republic of China.

An example of the mobile sensing platform 102a is shown as 102a'. The mobile sensing platform 102a' includes a site controller 113 (shown as "Control Ctrl" 113) that operatively connects over a long-range wireless link 117 to an edge controller 115 (see also 115') mounted on a UAAV 112a (shown as 112a'). The UAAV 112a' includes a winch assembly that is configured to deploy and retract the remote payload 114a (shown as 114a') via a tether. The remote sensing payload 114a' is configured to wirelessly connect to the edge controller 115 to operate synchronously with one another as the remote sensing payload samples 114a' a body of water at different depths and different locations while being deployed and extracted from a given different location by the unmanned aerial-amphibious vehicle.

In the example shown in FIG. 1B, the mobile sensing platform 102b includes the site controller 113 that may operatively connect over the long-range wireless link 117 to the edge controller 115' mounted on a vehicle. The vehicle 119, in the example shown in FIG. 1B, includes a robotic arm that attaches to the vehicle 119 at one end and has the sensor payload 114a' at the other end. The robotic arm is an elongated or elongate-able structure that can extend or hinge-ably move to put the remote sensor or payload (e.g., 114a') into the water body medium for water collection or sampling. The remote sensing payload 114a' is configured to wirelessly connect to the edge controller 115 to operate synchronously with one another as the remote sensing payload samples 114a' a body of water at different locations. The remote sensing payload 114a' may be configured to be self-powered and autonomous in operation via a low-power controller, so it does not require any electrical wiring between it and the edge controller 115 or vehicle 119.

Referring to FIG. 1A, the UAAV 112a is able to travel on/in water, on land, and in the air. For example, the UAAV 112a can travel on/in bodies of water 122, fly over the bodies of water 122, travel on levees, fly over the levees, and/or travel to/from the home station(s) 128. The present solution is not limited to the particulars of this example. In this regard, it should be noted that the UAAV 112 may have environmentally sealed housing such that dirt and water do not enter the same and cause damage to the internal components of the UAAV. Environmentally sealed housings are well known in the art and, therefore, will not be described in detail here. The environmentally sealed housing can include plastic parts or carbon fiber parts that are coupled to each other with water-tight seals formed therebetween by gaskets, o-rings, welds, etc.

The UAAV 112a is also able to perform hybrid movements and flight mode transitions to adapt to the terrain and weather; capable of avoiding obstacles at fixed locations (e.g., fixed aerators 124) and/or moving obstacles (e.g., mobile emergency aerators 130 or human-operated vehicles (not shown)); and able to react to any body of water 122 in distress by increasing its patrolling frequency and/or dispatching mobile emergency aerator(s) to that body of water.

The UAAV 112a may provide an all-weather coverage capability to system 100a that is important for aquaculture farm monitoring operations (especially in high-wind conditions). The sensing platform 102a is able to cover an entire aquaculture farm 120 in a reasonable period of time with high location precision, cost reductions, and/or biofouling reductions.

Sensor or collection payloads (e.g., 114a) are, preferably, remotely coupled to the UAAV 112a over a short-range wireless link between the topside edge controller 115 and the sensor payload. The sensor and/or collection payload may be mechanically coupled to the UAAV (e.g., 112*a*) via a tether as shown in FIG. 1A or additionally via adhesives, mechanical couplers (e.g., straps, clamps, nuts/bolts, screws, etc.), weld(s), and/or other coupling means in other embodiments. The sensors 114*a* may include, but are not limited to, dissolved oxygen sensors, Inertial Measurement Units ("IMUs"), barometers, temperature sensors, humidity sensors, wind speed sensors, wind direction sensors, rain sensors, solar radiation sensors, water pollution sensors, water contaminant sensors, water level sensors, turbidity sensors, pH sensors, fungus detectors, parasite detectors, biological oxygen demand sensors, oxidation-reduction potential sensors, colored dissolved organic matter sensors, salinity/conductivity sensors, cameras (e.g., digital, hyperspectral, etc.), a microphone, spectrographic sensors, chlorophyll sensor, and/or vibration sensors. Each of the listed sensors is well known in the art and, therefore, will not be described herein. The payload (e.g., 114*a*) can be selected so that its collective weight is relatively light (e.g., 50 grams or less).

As the UAAV 112*a* travels in, over, or between bodies of water 122, the payload or sensors (e.g., 114*a*) may generate sensor data and communicate the same to the UAAV 112*a*. The payload or sensors (e.g., 114*a*) are preferably submerged or may be at least partially submerged in water by the UAAV 112*a* during sensing operations. The UAAV 112*a* (or sensing vehicle 119) is configured to communicate the sensor data acquired via the payload 114*a*, through the edge controller 115, directly to a remote or cloud computing device 108 via a wireless communication link 104 and a network 106. In the example shown in FIGS. 1A and 1B, the sensor data may be transmitted to the site controller 113 over the long-range wireless link 117; the controller 113 then communicates the sensor data, or an aggregation of the sensor data (from the same edge controller or multiple edge controllers), to the remote or cloud computing device 108. Network 106 can include, but is not limited to, a wide area network (e.g., a Long Range ("LoRa") communications network), the Internet, a cellular network, and/or a radio network. The long-range wireless link 117 may include a cellular network, radio network, or other wide-area communication networks described herein. The sensor data generated by the sensors 114 can be processed by the computing device 108 (or additional computing devices, not shown) using a machine learning-based data analytical engine (not shown in FIG. 1) to predict the condition of the body of water 122. The sensor data, timestamps, and/or the predicted condition, as well as other analyses, of the body of water 122 may be stored in a datastore 110 and employed to generate a report (e.g., to output in a display or printed report).

In some embodiments, the machine learning-based data analytical engine is configured to employ a prediction model that is trained using weather data from weather reposts 150 and/or weather stations 152, timestamp data, and/or sensor data associated with all bodies of water in the aquaculture farm 120 that are used to raise fish 126 or other animals. The prediction model may be used to cause changes in the behavior of the sensing platform (e.g., 102*a*, 102*b*) to mitigate emergency situations and/or optimize the yield of farmed fish or other animals. Additional descriptions of the various analyses that may be performed on the sensor data may be found in U.S. Pat. No. 11,150,658, which is incorporated by reference herein in its entirety.

For example, the patrolling frequency of the aerial/amphibious sensing platform (e.g., 102*a*) may be increased or decreased based on model predictions, and/or a fixed aerator 124 is caused to be automatically or manually activated based on model predictions. Additionally, or alternatively, a human operator or a sensing platform is instructed to deploy a mobile aerator in a partial body of water at a given location therein. The deployed mobile aerator is then automatically or manually enabled or activated. The present solution is not limited to the particulars of this example.

The sensor data and/or predicted conditions of the body (ies) of water 122 may be presented to users on a computing device(s) 116. Computing device(s) 116 can include but is not limited to a personal computer(s), laptop computer(s), tablet computer(s), personal digital assistant(s), and/or smart phone(s). The graphical user interface ("GUI") for accessing and viewing such information may be Personal Computer ("PC") software-based, web browser based, and/or mobile application based. In the mobile application scenarios, the GUI may include a dashboard panel with text message instructions to allow the operator to react quickly to any emergency situation.

The computing device 108 may be employed to handle automatic emergency responses by the platform(s) (e.g., 102*a*, 102*b*). Once a body of water 122 is declared by computing device 108 to be in distress using the prediction model, an automatic emergency response process of system 100 is invoked. The automatic emergency response process may include, but is not limited to, deactivating fixed aerators 124, instructing field operators to deploy mobile aerators 130, activating the deployed mobile aerators 130, and/or increasing patrolling by platform(s) (e.g., 102*a*, 102*b*). When the computing device 108 detects that the body of water 122 is no longer in distress, the deployed mobile aerators 130 may be automatically deactivated by the computing device 108 and/or the platform(s) (e.g., 102*a*, 102*b*). The aerial platform(s) (e.g., 102*a*) may also return to their home station(s) 128 and transition from emergency patrolling operations (e.g., with more frequent patrols) to normal patrolling operations (e.g., with less frequent patrols).

The sensing platform (e.g., 102*a*, 102*b*) may be used to convert the aquaculture farm 120 operations to an Internet of Aquaculture. In this regard, it should be understood that the design of the system (e.g., 100*a*, 100*b*) can be readily scaled up to a multi-area framework and/or multi-farm framework, where a data center gathers sensor data from all the areas and/or farms for analysis and prediction. In the multi-area framework scenarios, home station 128 may be provided at several different locations across the aquaculture farm 120. Each home station 128 may be assigned a coverage area (e.g., 100 ponds). Each home station 128 may host one or more HAUCS sensing platforms 102 that are provided to monitor conditions of the respective coverage area. This multi-home station arrangement decreases UAAV traffic within the aquaculture farm 120. Upon completing a sensing session, each HAUCS sensing platform 102 returns to a respective home station 128, where automatic sensor cleaning may be performed in addition to or as an alternative to a power source (e.g., battery) recharging. The home stations 128 may also serve as communication hubs through which sensor data is indirectly passed from the HAUCS sensing platforms 102 to the computing device 108. Each home station 128 may also house mobile aerators 130 and/or back-up HAUCS platform(s) 132.

Computing device(s) 108, 113, 116 may also facilitate(s) mission planning for each sensing platform (e.g., 102*a*, 102*b*) and/or the simulation of planned mission operations. In this regard, the computing device(s) 108, 113, 116 may employ a mission planner and a simulator (e.g., ROS Gazebo integrated with Ardupilot and/or a RealFlight simulator available from Horizon Hobby LLC of Illinois). A GUI of the computing device(s) 108, 116 may provide a synoptic visualization of the aquaculture farm's status produced by the prediction model and/or the statuses of other resources (e.g., fixed aerator(s) 124, mobile aerator(s) 130). The GUI may also provide automatic emergency response notifications.

The mission control and path planning algorithm employed by the system (e.g., 100a, 100b) may be crucial to achieving the coordination among multiple sensing platforms (e.g., 102a, 102b) to provide persistent, accurate, and up-to-date situational awareness and to collaborate with human operators to accomplish farm water quality control. The mission control of a sensing platform (e.g., 102a, 102b) may be designed to meet the following challenges: reaction to a pond in distress by increasing a HAUCS sensing platform's patrolling frequency and dispatching mobile emergency aerators to that pond; hybrid movements and flight mode transitions to adapt to the terrain and weather; and cable of avoidance of obstacles at fixed locations (e.g., fixed aerators) and moving obstacles (e.g., mobile emergency aerators or human-operated vehicles).

Flight mode changes of the aerial/amphibious sensing platforms (e.g., 102a) may be handled by location-based waypoint assignments: sampling waypoints (i.e., moving within the same body of water) and transition waypoints (i.e., moving to a different body of water or to a home station on land). To cope with severe weather, the computing device 108 may maintain the third type of waypoint-protective waypoints. For example, upon the detection of potentially strong wind, the computing device 108 can update the waypoints to protective waypoints to allow the aerial/amphibious sensing platforms (e.g., 102a) to take evasive actions. The computing device 108 can restore the waypoint status at a later time when the wind condition returns to normal.

Example UAAV System

Figure 2:
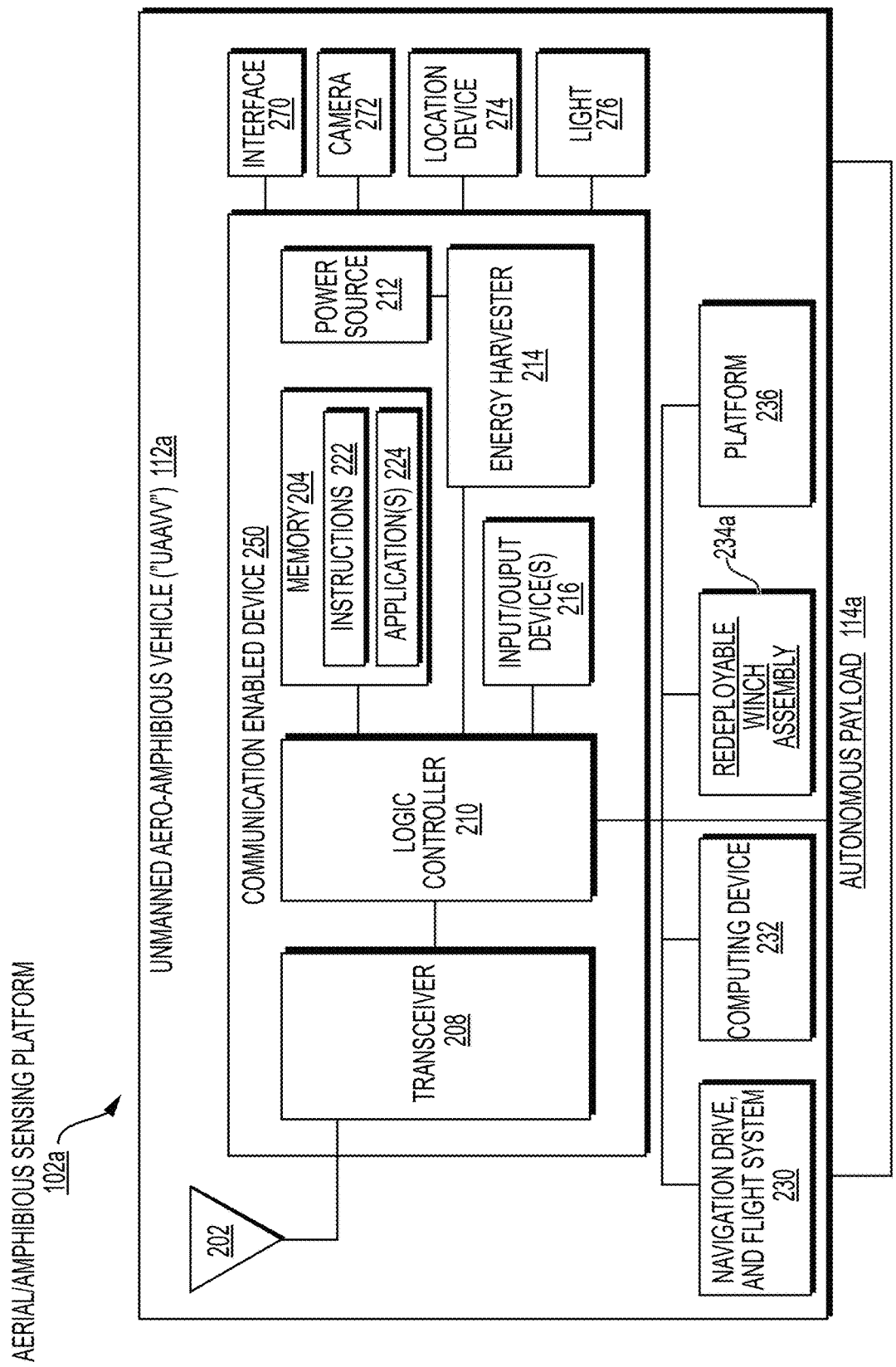
FIG. 2 block diagram of an illustrative architecture for the aerial/amphibious sensing platform of FIG. 1A.

FIG. 2 is a block diagram of an illustrative architecture for the aerial/amphibious sensing platform (e.g., 102a) of FIG. 1A. In the example shown in FIG. 1A, the aerial/amphibious sensing platform (e.g., 102a) includes components that can be implemented in hardware, software, and/or a combination of hardware and software. The hardware may include but is not limited to one or more electronic circuits. The electronic circuit may comprise passive components (e.g., capacitors and resistors) and active components (e.g., processors) arranged and/or programmed to implement the methods disclosed herein.

The hardware architecture of FIG. 2 represents an illustrative architecture of a representative aerial/amphibious sensing platform (e.g., 102a) configured to facilitate the mitigation of emergency situations and/or the optimization of the yield of farmed fish or other animals. In this regard, the aerial/amphibious sensing platform (e.g., 102a) comprises a UAAV 112a with a communication-enabled device 250 for allowing data to be exchanged with an external device (e.g., computing device 108 of FIG. 1A or 1B, e.g., by way of an edge controller 115, as well as aerators 124, 130 of FIG. 1A or 1B, other sensing platforms (e.g., 102, 132) of FIG. 1A or 1B, and/or other devices) via wireless communication technology. The communication technology can include but is not limited to cellular technology, radio frequency ("RF") technology, Bluetooth technology, and/or WiFi technology. The components 204-216 shown in FIG. 2 may be collectively referred to herein as the communication-enabled device 250.

In the example shown in FIG. 2, the communication-enabled device 250 includes a power source 212. The power source 212 includes, but is not limited to, a battery (e.g., a Lithium polymer ("Li—Po") battery), capacitor(s), and/or an aluminum powder-based energy source. The aluminum powder-based energy source implements a method of activating bulk aluminum and allowing the activated bulk aluminum to react with water to produce hydrogen gas and stream. The water used by the aluminum powder-based energy source may be stored in a tank of the UAAV (e.g., 112a). Additionally or alternatively, the water used by the aluminum powder-based energy source can be fetched by the UAAV (e.g., 112a) from a body of water 122 as the sensors or collection payloads (e.g., 114a) may sense conditions of the body of water 122.

The battery and/or capacitor(s) may be rechargeable. The battery and/or capacitor(s) may be recharged when it rests in a cradle of or otherwise on a home station 128 of FIG. 1A or 1B.

The communication-enabled device 250 may include an antenna 202 for allowing data to be exchanged with the external device via a wireless communication technology (e.g., RFID technology or other RF-based technology). The external device may comprise computing device(s) (e.g., 108, 113, 115, 116) of FIG. 1A or 1B, aerators 124, 130 of FIG. 1A or 1B, other sensing platforms (e.g., 102a, 102b, 132) of FIG. 1A or 1B, and/or other devices. In this case, the antenna 202 may be configured to transmit signals to and received signals from the listed external devices. In this regard, the communication-enabled device 250 may comprise a transceiver 208. Transceivers are well known in the art and, therefore, will not be described herein. However, it should be understood that the transceiver 208 receives signals, including information from a transmitting device, and forwards the same to a logic controller 210 for extracting the information therefrom.

The extracted information can be used to initiate, enable, disable or modify operations of the UAAV (e.g., 112a). Accordingly, the logic controller 210 can store the extracted information in memory 204 and execute algorithms using the extracted information. For example, the logic controller 210 can receive a command from the computing device(s) (e.g., 108, 113, 116) of FIG. 1A or 1B to initiate or activate normal or emergency sensing operations; cause a Navigation, Drive, and Flight ("NDF") system 230 to operate such that the aerial/amphibious sensing platform (e.g., 102a) follows a given path of travel through a geographic area via land/air/water, hover over certain geographic locations for given amounts of time (e.g., 30 seconds); cause the aerial/amphibious sensing platform (e.g., 102a) to submerge the sensor or collection payload (e.g., 114a) in water at certain locations and for certain periods of time; cause the aerial/amphibious sensing platform (e.g., 102a) to communicate sensor data to one or more external devices; cause the energy harvester 214 to collect energy and use the same to power one or more components of the aerial/amphibious sensing platform (e.g., 102a); cause the aerial/amphibious sensing platform (e.g., 102a) to return to a respective home station 128 of FIG. 1A or 1B (e.g., for recharging the power source 212 and/or maintenance of sensor or collection payload (e.g., 114a)); cause a camera 272 to capture video and/or images as the aerial/amphibious sensing platform (e.g., 102a) travels through the geographic area; cause the aerial/amphibious sensing platform (e.g., 102a) to communicate with other devices in the geographic area; cause a computing device 232 to process sensor data and/or communicate results of the processing to external devices; cause data to be stored in memory 204; and/or cause the aerial/amphibious sensing platform (e.g., 102a) to communicate with personnel. Camera 272 includes, but is not limited to, a visible camera, an IR camera, and/or a UV camera.

In some scenarios, the UAAV (e.g., 112a) comprises a manipulator 234 (shown as "Redeployable Winch Assembly" 234a) to place the sensor or collection payload (e.g., 114a), place aerators 130 or other devices at given locations in an aquaculture farm 120, and/or to collect samples of water, soil, plants and/or animals. In some embodiments, the manipulator 234 may include robotic manipulators that are well known in the art and, therefore, will not be described herein. Any known or to-be-known manipulator can be used herein without limitation. FIGS. 4A-4E are diagrams showing an example re-deployable winch assembly 234a that may be employed. The UAAV (e.g., 112a) may optionally return to the home station 128 each time one or more samples are collected and/or when a malfunction thereof is detected. The water samples can be analyzed by the UAAV (e.g., 112a), the home station 128, and/or at another location, for example, for off-flavor compounds (e.g., Geosmin and 2-Methylisoboerneol).

As noted above, the camera 272 and/or sensors or collection payloads (e.g., 114a) is configured to obtain information about the conditions of a geographic area and/or body of water. This information is logged in memory 204 and/or communicated to an external datastore (e.g., a remote database). Memory 204 may be a volatile memory and/or a non-volatile memory. For example, the memory 204 can include, but is not limited to, a Random Access Memory ("RAM"), a Dynamic Random Access Memory ("DRAM"), a Static Random Access Memory ("SRAM"), a Read-Only Memory ("ROM") and a flash memory. The memory 204 may also comprise unsecure memory and/or secure memory. The phrase "unsecure memory," as used herein, refers to memory configured to store data in a plain text form. The term "secure memory," as used herein, refers to memory configured to store data in an encrypted form and/or memory having or being disposed of in a secure or tamper-proof enclosure.

The camera 272 and/or sensors or payload 114 have fixed or variable positions relative to the platform 236. In the variable position scenario, the camera 272 and/or sensors 114 are mounted to a retractable mechanical or electro-mechanical device that allows the devices 272, 114 to be retracted during the UAAV's flight and extended during sensing operations. Retractable mechanical and electro-mechanical devices are well known in the art and, therefore, will not be described herein. For example, the retractable mechanical or electro-mechanical device can include but is not limited to a servo motor, a winch, gears, a mechanical linkage, a telescoping arm, a boom, and/or an articulate arm. The retractable feature of the sensor or collection payload (e.g., 114a) allows for the minimization of contact between the platform 236 and the body of water 122, which reduces the energy consumption during the operation of the aerial/amphibious sensing platform.

Instructions 222 are stored in memory for execution by the communication-enabled device 250 and that causes the communication-enabled device 250 to perform any one or more of the methodologies of the present disclosure. The instructions 222 are generally operative to facilitate the mitigation of emergency situations and/or the optimization of the yield of farmed fish or other animals. Other functions of the communication-enabled device 250 will become apparent as the discussion progresses.

In some scenarios, the computing device 324 employs an Open Autopilot software capable of controlling autonomous vehicles. The Open Autopilot software includes, but is not limited to, ArduPilot. A Robotic Operating System ("ROS") may be integrated with the Open Autopilot software in a Software-In-The-Loop ("SITL") fashion for tasks such as mission control and planning, flight mode modification, information retrieval, and/or sensor data acquisition. Interface 270 can provide a Human Machine Interface ("HMI") that will allow individuals to gain overall farm situational awareness, to tasks or re-task HAUCS platforms, and/or to issue instructions to field operators (e.g., to move mobile aerators).

The UAAV (e.g., 112a) may also include a lightweight, waterproof, mechanical platform 236. The platform 236 is adapted to hold, contain and/or otherwise support the components shown in FIG. 2 and/or other items. In some scenarios, the platform 236 comprises a deck or a bed with a single support surface or multiple support surfaces separated by dividers (e.g., bins, shelves, or drawers). Devices (e.g., aerators 130 of FIG. 1A or 1B) can be placed on or removed from the platform 236 via the manipulator(s) 234. The manipulator(s) 234 may also be used to place devices (e.g., aerators 130 or sensor or collection payload 114a of FIG. 1A or 1B) and/or other items at strategic or pre-defined locations within an area of interest. In this regard, the manipulator(s) 234 are generally configured to grasp or otherwise hold the devices (e.g., aerators 130 of FIG. 1A or 1B) and/or other items.

The Navigation, Drive, and Flight (NDF) system 230 of UAAV (e.g., 112a) is generally configured to move the aerial/amphibious sensing platform (e.g., 102a) within a surrounding environment without coming in contact with obstructions and without tipping over. In this regard, the NDF system 230 may include but is not limited to an air-based propulsion system, a water-based propulsion system, a drive train, drive wheels, tracks (such as those found on tanks), and/or a' GPS guidance system. The NDF system 230 is configured, in some embodiments, to continuously determine and track the UMM's position and location relative to other objects within a surrounding environment. NDF systems are well known in the art and, therefore, will not be described in detail herein. Any known or to be known NDF system can be used herein without limitation. In some scenarios, beacons and/or RFID tags are used by the NDF system 230 to track the UAAV's location within a given area. Additionally or alternatively, the NDF system 230 uses other techniques (e.g., triangulation) to track the UAAV's location.

The UAAV (e.g., 112a) is not limited to the architecture shown in FIG. 2. The UAAV (e.g., 112a) may include more or fewer components than shown in FIG. 2. For example, the UAAV (e.g., 112a) may include Light Detection And Ranging ("LIDAR") devices and/or hyperspectral imaging devices for further facilitating the generation of accurate relative distance and direction information. LIDAR devices and/or hyperspectral imaging devices are well known in the art and, therefore, will not be described herein. Any known or to be known LIDAR device(s) and/or hyperspectral imaging device(s) can be used herein without limitation.

The UAAV (e.g., 112) may also include lights 276, e.g., for signaling, sensing, or safety. The lights 276 may include but are not limited to camera lights, light emitting diodes, spot lights, and/or navigation lights. Each of the listed lights is well known in the art and, therefore, will not be described herein. The lights 276 may be selected in accordance with a given application and/or in accordance with applicable regulations.

Figure 3:
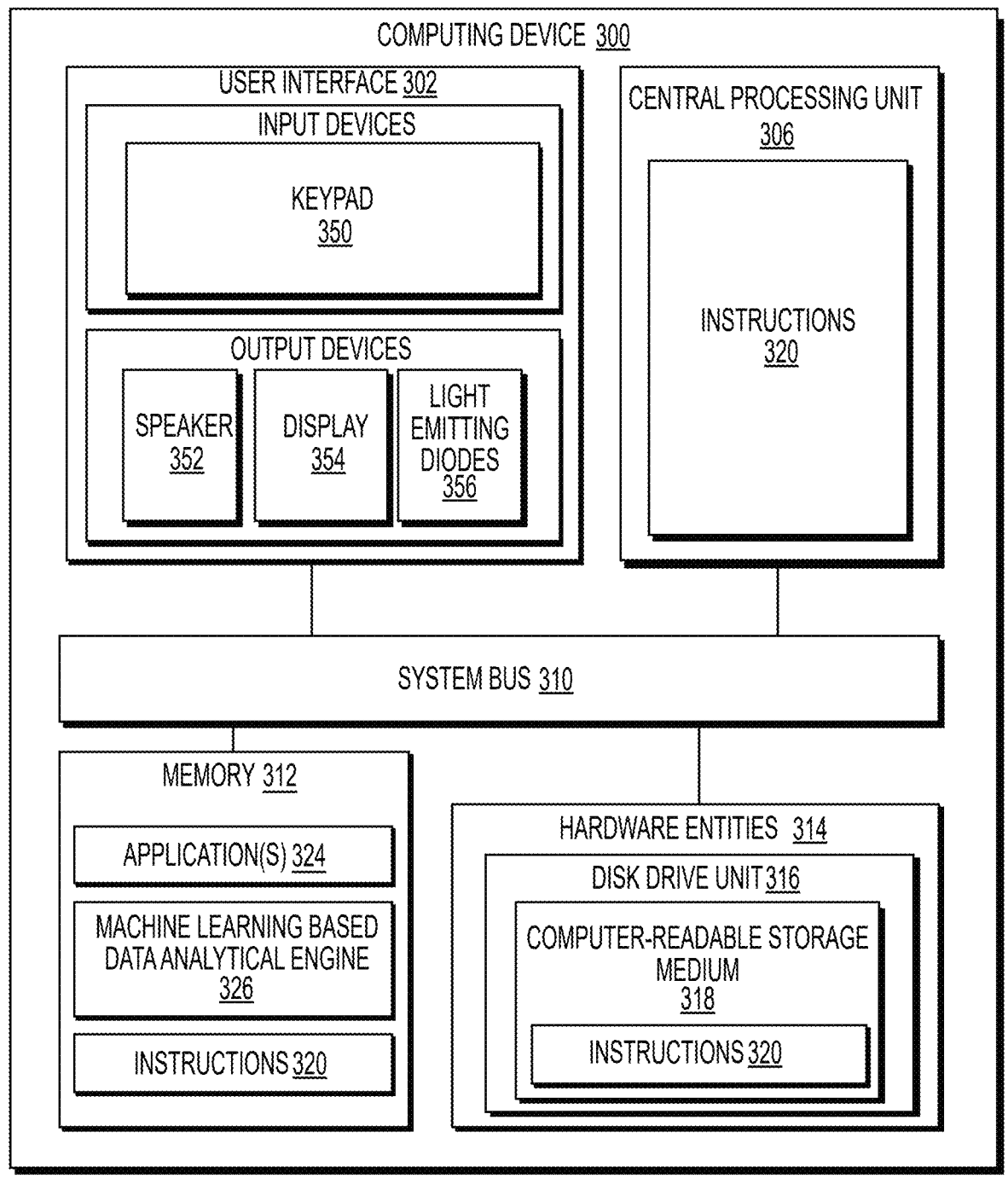
FIG. 3 is a diagram showing a block diagram of an illustrative architecture for a computing device of an aerial/amphibious sensing platform or analysis system.

FIG. 3 is a diagram showing a block diagram of an illustrative architecture for a computing device 300, e.g., for the computing device(s) 108, 113, 116 of FIG. 1A or 1B and/or computing device 232 of FIG. 2. Because they are the same as or substantially similar to computing device 300, as such, the following discussion of computing device 300 is sufficient for understanding computing device(s) 108 and 116 of FIG. 1A or 1B and/or computing device 232 of FIG. 2. Computing device 300 may include more or fewer components than those shown in FIG. 3. However, the components shown are sufficient to disclose an illustrative embodiment of implementing the present solution. The hardware architecture of FIG. 3 represents one embodiment of a representative computing device configured to facilitate the mitigation of emergency situations and/or the optimization of the yield of farmed fish or other animals. As such, computing device 300 of FIG. 3 implements at least a portion of the methods described herein.

Some or all the components of the computing device 300 can be implemented as hardware, software, and/or a combination of hardware and software. The hardware includes, but is not limited to, one or more electronic circuits. The electronic circuits can include but are not limited to passive components (e.g., resistors and capacitors) and/or active components (e.g., amplifiers and/or microprocessors). The passive and/or active components can be adapted to, arranged and/or programmed to perform one or more of the methodologies, procedures, or functions described herein.

As shown in FIG. 3, the computing device 300 comprises a user interface 302, a Central Processing Unit ("CPU") 306, a system bus 310, a memory 312 connected to and accessible by other portions of computing device 300 through the system bus 310, and hardware entities 314 connected to the system bus 310. The user interface can include input devices (e.g., a keypad 350) and output devices (e.g., speaker 352, a display 354, and/or light emitting diodes 356), which facilitate user-software interactions for controlling operations of the computing device 300. In some scenarios, the CPU 306 additionally or alternatively includes a Graphical Processing Unit ("GPU"). In some embodiments, the CPU 306 includes an AI processor, application-specific integrated circuits (ASICs), field-programmable gate arrays (FPGA), or other programmable digital logic systems.

At least some of the hardware entities 314 perform actions involving access to and use of memory 312, which can be RAM, a disk driver, and/or a Compact Disc Read Only Memory ("CD-ROM"). Hardware entities 314 can include a disk drive unit 316 comprising a computer-readable storage medium 318 on which is stored one or more sets of instructions 320 (e.g., software code) configured to implement one or more of the methodologies, procedures, or functions described herein. The instructions 320 can also reside, completely or at least partially, within the memory 312 and/or within the CPU 306 during execution thereof by the computing device 300. The memory 312 and the CPU 306 also can constitute machine-readable media. The term "machine-readable media," as used here, refers to a single medium or multiple media (e.g., a centralized or distributed database and/or associated caches and servers) that store one or more sets of instructions 320. The term "machine-readable media," as used here, also refers to any medium that is capable of storing, encoding, or carrying a set of instructions 320 for execution by the computing device 300 and that causes the computing device 300 to perform any one or more of the methodologies of the present disclosure.

In some scenarios, the hardware entities 314 include an electronic circuit (e.g., a processor) programmed for facilitating the mitigation of emergency situations and/or the optimization of the yield of farmed fish or other animals. In this regard, it should be understood that the electronic circuit can access and run application(s) 324 installed on the computing device 300. The software application(s) 324 is (are) generally operative to facilitate: the training of a prediction model for a machine learning-based data analytical algorithm; the planning of missions for sensing platforms (e.g., 102a, 102b, 132) of FIG. 1A or 1B based on the prediction model; the simulations of the planned missions and corresponding operations to be performed by the sensing platforms (e.g., 102a, 102b, 132) of FIG. 1A or 1B; the verification, approval, and/or authorization of the planned missions; the remote control or programming of the sensing platforms (e.g., 102a, 102b, 132) of FIG. 1A or 1B to implement the planned missions; the reception of sensor data from the sensing platforms (e.g., 102a, 102b, 132) of FIG. 1A or 1B; the analysis of the sensor data to accurately predict water quality variation; the detection of emergency situations; the emergency notifications; and/or the performance of remedial measures in emergency situations. Other functions of the software application 324 will become apparent as the discussion progresses.

The software application(s) 324 (e.g., executing on cloud infrastructure) may utilize a machine learning-based data analytical engine 326. The engine 326 may employ a recurrent neural network ("RNN"). The RNN can include, but is not limited to, a long-short-term memory ("LSTM") model that preserves long-range dependencies in time series prediction. The LSTM model does not operate satisfactorily when there is incomplete data (i.e., gaps in the time series data). Incomplete data or missing data can be expected to occur frequently in the field due to interferences from various sources. Additional description of the cloud infrastructure and/or internet-of-things infrastructure may be found in U.S. Pat. No. 11,150,658, which is incorporated by reference herein in its entirety. Additional examples of optimized hardware for the edge controller is additionally provided herein.

Example Precision Agriculture Application

Precision agriculture ("PA") is the application of robotic field machines and information technology in agriculture. PA plays an increasingly important role in farm production. PA-related robotic technology has been an active research topic and has seen robust growth. By USDA estimation, between 1998 and 2013, the three key PA technologies (i.e., Global Positioning System ("GPS") yield and soil monitors/maps, Variable-Rate input application Technologies ("VRT"), and GPS guidance systems) have seen adoption rates ranging from twenty-five percent to fifty percent. Many PA applications call for multiple collaborative robots, which are closely related to the general topics of the Multi-Robot Patrol Problem ("MRPP") or the Multi-Robot Persistent Coverage Problem ("MRPCP"). MRPCP aims to continuously monitor an area of interest and to minimize the time between visits to the same region. These topics have gained a strong interest in the research community and NSF support. However, aquaculture farming is an important sector of agriculture that has seen minimal robotic development.

The Internet of Things ("IoT") has been adopted to improve productivity and efficiency in agriculture. Aquaculture farming is an important, fast-growing sector of agriculture that has seen the applications of advanced technologies such as robotics and IoT.

IoT solutions have been adopted to realize automated feeding on fish farms to reduce feed waste and avoid water pollution from the application of excessive feed. In computer-vision-based automatic feeder designs, videos are streamed via Bluetooth to a control center where the fish feeding behavior is analyzed to determine the degree of hunger, which in turn, controls feeder operation. While such a system might be viable for a small-scale fish tank, it would be challenging to scale up to a fish farm with numerous larger ponds (e.g., >2 hectares). To this end, eFishery is a more realistic IoT-based fish feeder system. The eFishery system is essentially an enhancement demand feeder. One novel design in eFishery is that a vibration sensor is adopted to detect fish activity near the feeder. The sensor data is sent back to the control center for analysis to determine the degree of hunger in the pond, which controls the operation of the feeder. Every feeding event initiated by the feeder is recorded automatically to allow the farm to monitor feed expenses In aquaculture fish farms, management of water quality (e.g., Dissolved Oxygen ("D.O.")) is critically important for successful operation. D.O. depletion is a leading cause of fish loss on farms. Catastrophic loss can occur within hours if ponds aren't managed properly. The current management practice on pond-based farms is the use of human operators who drive trucks or other all-terrain vehicles throughout the day and night, sampling D.O. in each culture pond, targeting a sampling frequency of at least once per hour. The associated labor and equipment costs limit the scope and frequency of such sampling efforts since dozens of ponds must be managed by each truck. Large farms require multiple drivers and sampling instruments to attain the required monitoring frequency. Also, the level of resolution that this approach is able to achieve on any single pond is generally restricted to a single near-shore measurement at a point on the pond that has a well-maintained roadbed. On large ponds (e.g., 2 to 8 hectares or 5 to 20 acres), this can result in a failure to promptly identify localized water quality problems that can ultimately affect a large proportion of the crop. Multiple measurements are only taken on ponds that are in a state of depressed D.O. and receiving supplemental aeration. The measurement of additional water quality parameters cannot be done due to the demanding schedules required of drivers to achieve the minimum measurement frequency. Even though readings should be taken hourly on each pond, very large farms (e.g., farms that are greater than 1000 acres) with hundreds of ponds may only be able to take readings every other hour or every third hour due to labor and equipment costs of operating large fleets of monitoring vehicles. Furthermore, with the current practice, operators have a very limited window of time (e.g., less than an hour or so in the middle of the night) to react to potential oxygen depletion, increasing the potential likelihood of catastrophic events, and the response (e.g., putting emergency aeration equipment in a pond) takes time away from achieving D.O. measurement frequencies.

There have been attempts to reduce labor costs by automating aquaculture pond monitoring, such as the Aquaculture Pond Buoy from In-Situ Inc. of Fort Collins, Colo. Other IoT water quality monitoring solutions include Neer Yantra from PranisCOM and PondGuard from Eruvaka. These and many other solutions employ buoy-based monitoring stations that measure pond-water quality parameters such as D.O., temperature, pH, etc. Sensor data can be sent via WiFi or cellular link to a control center for analysis. However, such stationary instruments are difficult to maintain due to biofouling and can be cost-prohibitive since they require one sensor for each pond. Also, a stationary instrument suffers from the same limitation as truck-based monitoring since only a single location is monitored unless multiple expensive sensor buoys are deployed in each pond. Sensor buoys are an obstruction in the pond during harvest since they have to be removed or lifted over the seine. This is mitigated a bit by wireless buoys, but wired buoys are excessively cumbersome for operators.

To mitigate these issues, the present solution provides a HAUCS sensing platform. HAUCS is a transformative robotic system that brings fundamental innovations to how aquaculture farms operate. HAUCS conducts automated sampling at frequencies relevant for accurate prediction of water quality variation (e.g., hourly diel readings), providing significant advantages in speed, cost, resource efficiency, and adaptability over the traditional manual and truck-mounted water quality measurement systems on the farms. HAUCS is capable of collaborative monitoring and decision-making on farms of varying scales. HAUCS is an end-to-end framework consisting of three essential subsystems: a team of collaborative aero-amphibious robotic sensing platforms capable of air, land, and water movements, integrated with underwater sensors; a land-based home station that provides automated charging and sensor cleaning; and a backend processing center consisting of a machine learning based water quality prediction model and farm control center. Each HAUCS platform covers a subset of ponds and automatically acquires sensor data in each pond at regular intervals. The amphibious design enables the platform to move over the levee separating the ponds and to better cope with severe weather, such as high wind. The automatic cleaning at the land-based home station significantly reduces the risk of sensor biofouling. The "brain" in the backend processing center provides "several-steps-ahead" predictions of the pond water quality, detects upcoming compromised water quality (such as dissolved oxygen depletion), and mitigates pond distress either automatically or in close collaboration with the human site managers and operators.

The HAUCS framework is a disruptive technology that has the potential to markedly increase the adoption of robotic technology in the field of aquaculture farming, a sector of agriculture that has seen minimal robotics development. The HAUCS framework allows one critical factor plaguing aquaculture farming to be overcome—the high-cost and unreliability of water quality controls, in particular, dissolved oxygen depletion. Moreover, the underlying rationale and methodology of building an "internet of things" framework is to enhance the HAUCS's capacity to integrate multiple tasks typically performed on aquaculture farms. This technology, therefore, has significant social, environmental, and economic benefits and can fundamentally transform how pond aquaculture is conducted in the United States and around the world.

As a whole, the HAUCS or aerial/amphibious framework described herein is innovative and streamlines continuous monitoring, maintenance, and forecasting of next-generation fish farms. The framework offers a highly flexible and scalable solution that can be adapted to a diversity of farms to achieve farm-level and pond-level monitoring. The machine learning-based data analytical engine allows farmers to stay "several-steps-ahead" of any potential catastrophic event, such as dissolved oxygen depletion. The platform design integrates an aero-amphibious platform and underwater sensors, providing a foundation for fully automated aquaculture maintenance. The water quality data collected provides for a better understanding of water quality dynamics in aquaculture ponds that will lead to improvements in the efficiency and reliability of pond aquaculture and thus help to ensure food security. Compared with state-of-the-art, the HAUCS framework has the following advantages: improved scalability (capable of collaborative monitoring and decision-making on farms of varying scales); more accurate reporting of pond conditions (capable of sampling multiple locations in the pond to monitor spatial and temporal pond variations); mitigating biofouling (avoiding maintaining sensors in bio-productive water); and avoiding single point coverage (novel sensing patterns can be realized to cover different areas on a large pond).

A major reason for the low adoption of robotic technology in aquaculture fish farming is the lack of accessibility to technology for fish farmers.

Example Device

Figure 4A:
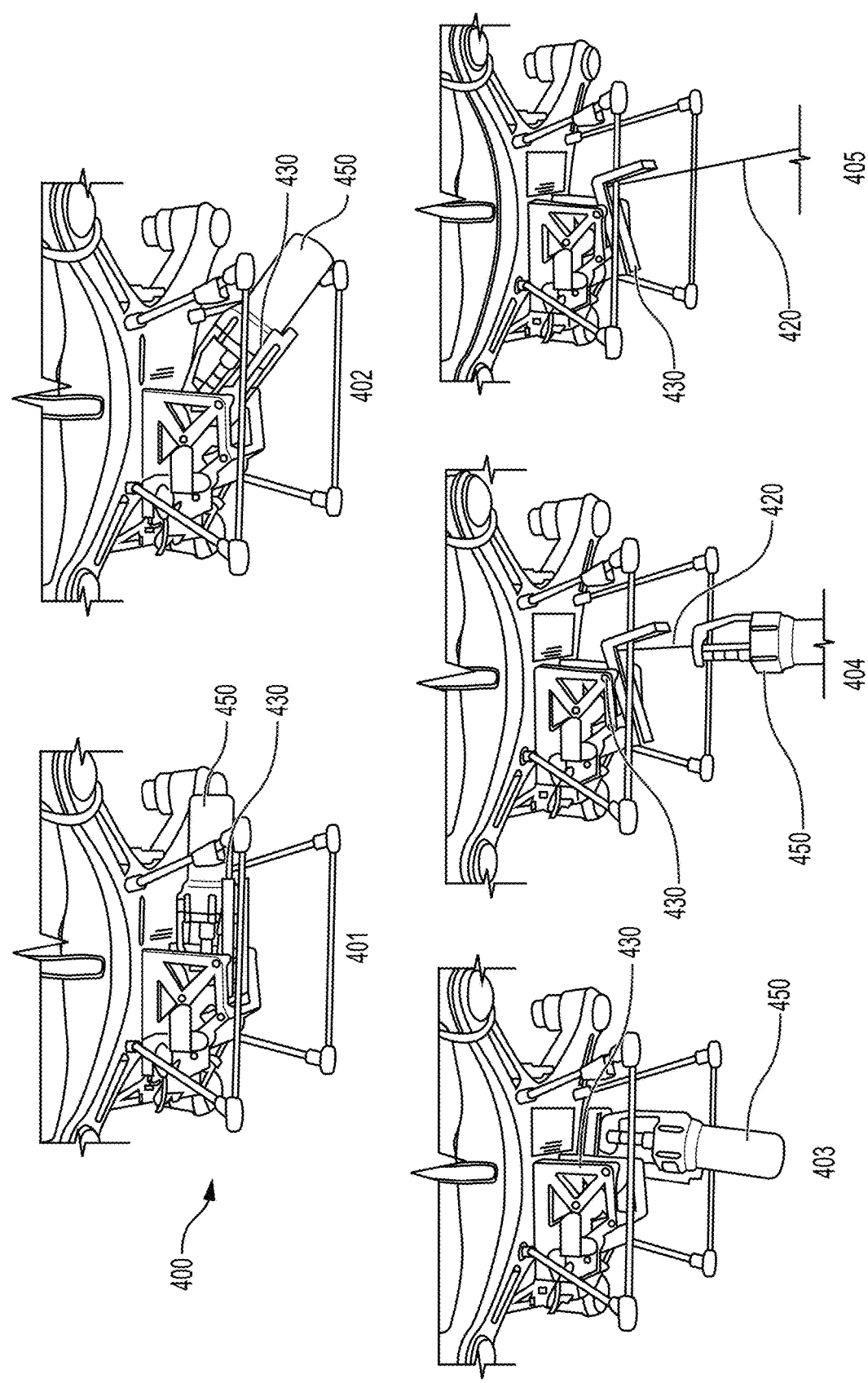
FIGS. 4A and 4B are each a series of images showing a deployment and extraction operation, respectively, of an example aerial/amphibious sensing platform configured with an example winch payload deployment assembly apparatus in accordance with an illustrative embodiment.
Figure 4B:
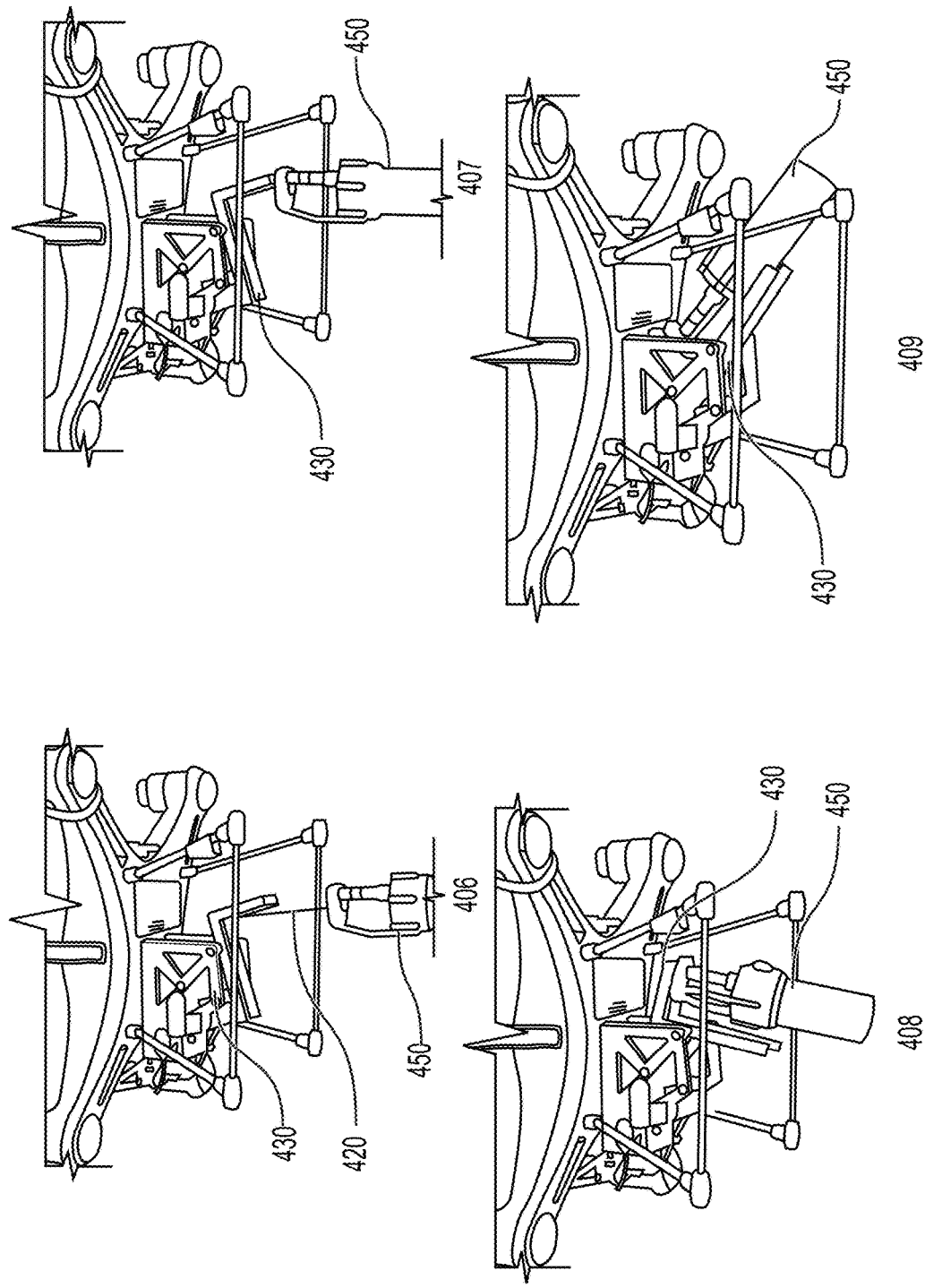
Figure 4C:
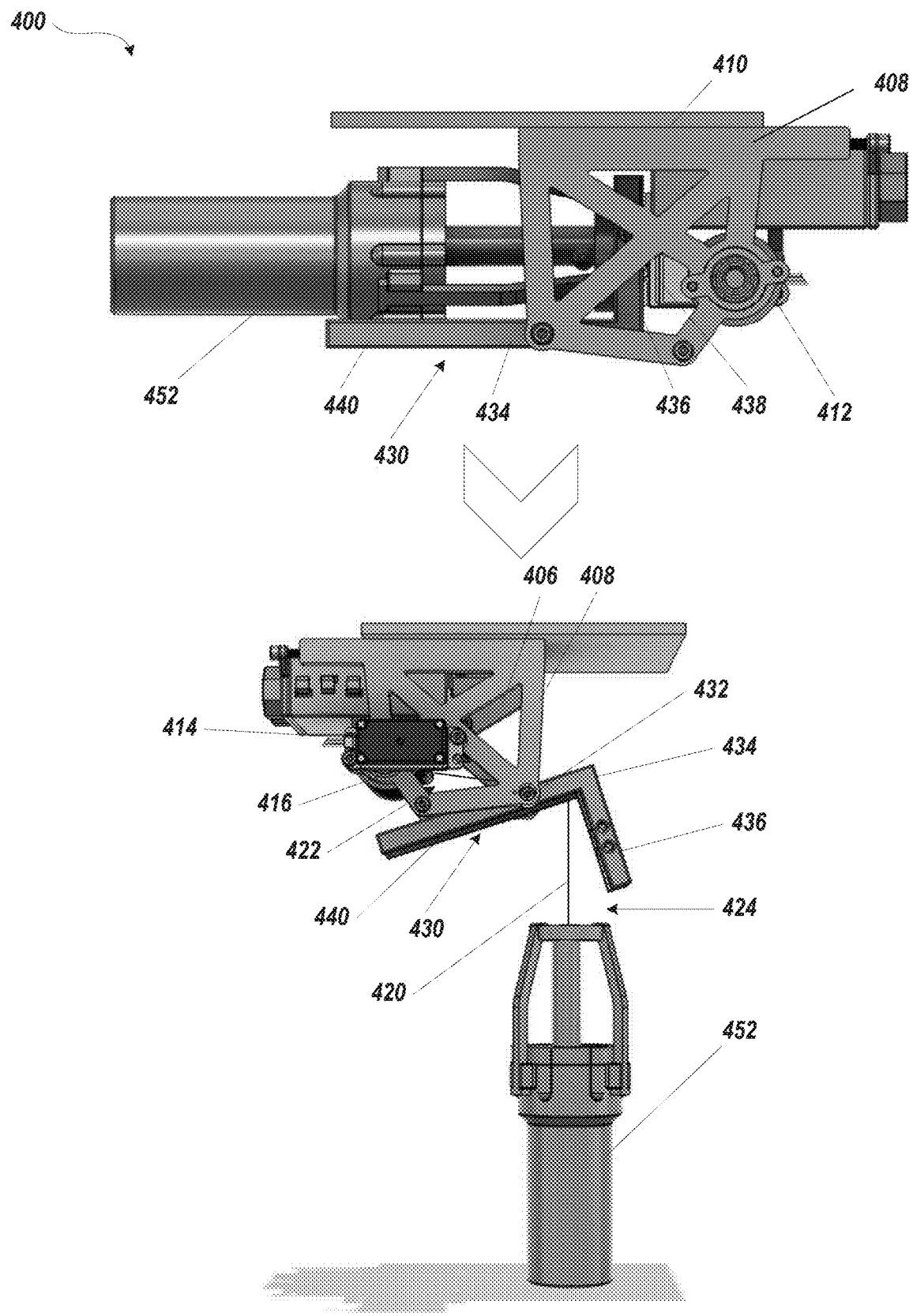
FIGS. 4C, 4D, and 4E are each a diagram of the example winch payload deployment assembly apparatus of FIGS. 4A and 4E in accordance with an illustrative embodiment.
Figure 4D:
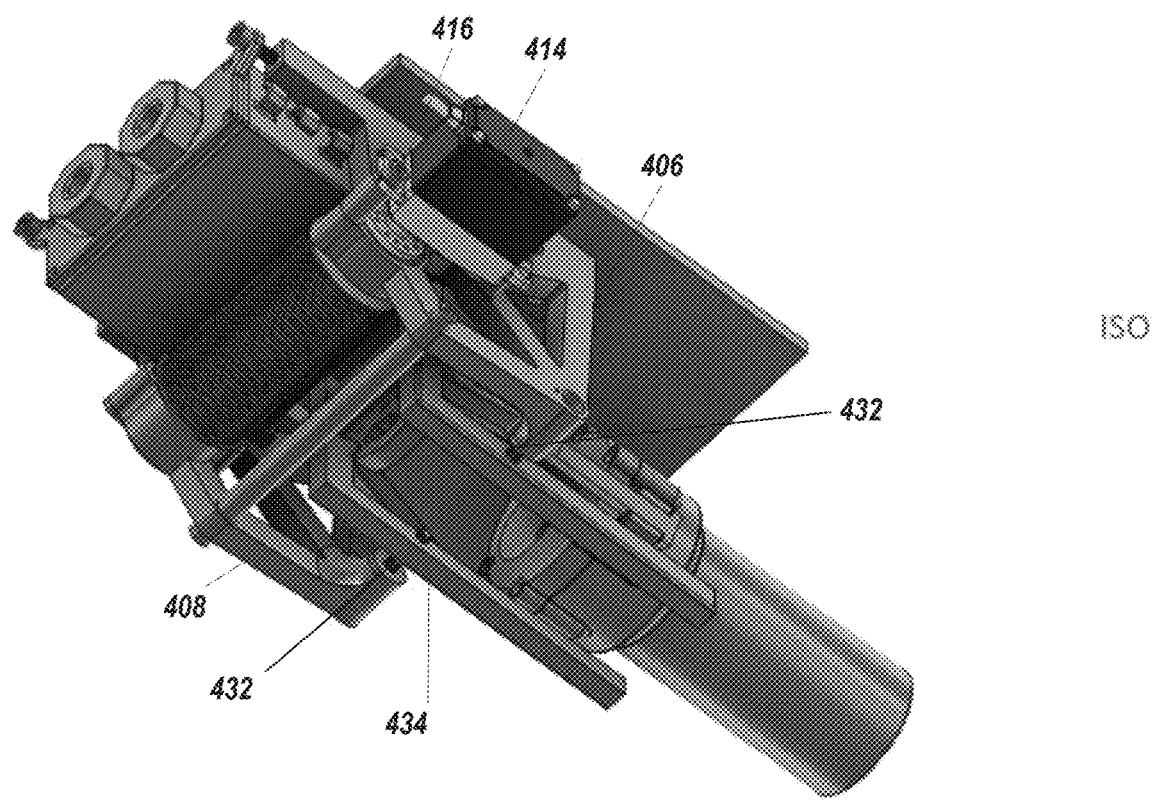
Figure 4E:
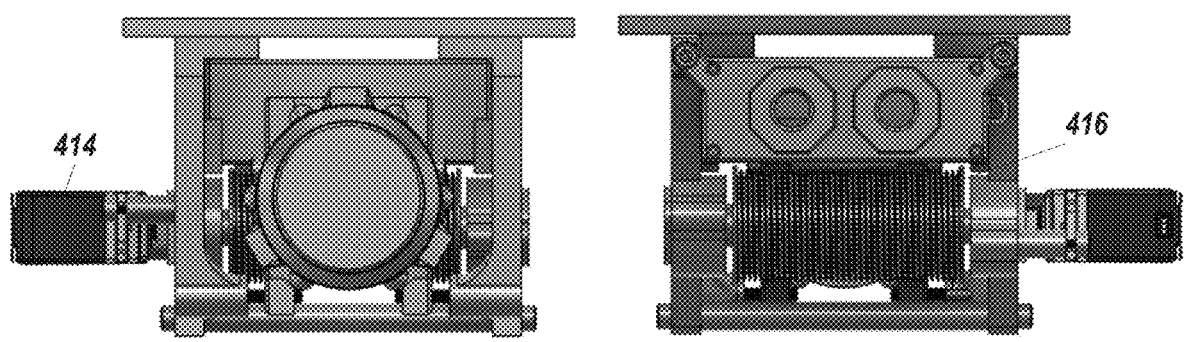

FIGS. 4A and 4B are each a series of images showing a deployment and extraction operation, respectively, of an example aerial/amphibious sensing platform configured with an example winch payload deployment assembly apparatus 400 (or, simply "apparatus" 400), to deploy and extract a sensor or collection payload (e.g., 114a), in accordance with an illustrative embodiment. FIGS. 4C, 4D, and 4E are each a diagram of the example winch payload deployment assembly apparatus of FIGS. 4A and 4E in accordance with an illustrative embodiment.

The apparatus 400 is configured to attach to an aero-amphibious vehicle (e.g., 112a) to provide a robust winch system that can automatically fold during flight by turning downward for payload release, e.g., during the sensing/collection operation and folding back up after the sensing/collection operation. The winch system may be optimized to operate via a single actuator to minimize weight, perform the remote sensor release and capture, and extend the remote sensor into the body of water. By stowing the payload during flight, the UAAV reduce risks of unintended movement resulting from the motion of the payload. This reduce the risk of damage to the drone, as well as reduce power consumption wasted to counter such unintended movement, and reduce the UAAC requirements (e.g., power and size) for a given payload.

In FIG. 4C, the apparatus includes a winch chassis 410, a tether 420, a bracket 430, a spool 412, and an actuator 414.

The winch chassis 410 includes a coupling assembly 416 between the spool 412 and the actuator 414. The actuator 414, as a motor, includes a motor output that is coupled to the spool 412 via one or more gears or a gearbox. The winch chassis 410 employs a first side wall 408 and a second side wall 406 for fixably retaining the spool 412, the actuator 414, and the bracket 430. The first and second side walls 408, 406 also couple the apparatus 400 to the vehicle (e.g., 112a). The actuator 414, in some embodiments, is a servo motor; however, in other implementations, the actuator 414 may be any other component capable of rotating the spool 412 (e.g., a stepper motor, DC motor, and the like).

The tether 420 is configured to wound around the spool 412. The tether 420 is fixably attached to the winch chassis 410 at its first end 422 (of the winch) and to the payload 114a and at its second end 424. The tether 420 is preferably a metal cable (e.g., a tension wire); however, in other implementations, the tether is any other wire-like material capable of supporting the payload and being wound around the spool (e.g., string, paracord, chain, etc.).

The bracket 430 is configured to automatically fold during flight by turning downward for payload release, e.g., during the sensing/collection operation and folding back up after the sensing/collection operation. In the example shown in FIGS. 4C-4E, the bracket 430 is coupled to the winch chassis 410, e.g., via a torsional spring 432 to bias in a payload release configuration and may be configured to operate via the pull or release of the tether 420. The bracket 430 is configured to move between a stowed position to a deployed position (e.g., see FIG. 4C). In the stowed position, the sensor or collection payload (e.g., 114a) abuts against a back portion 436 of the bracket 430. In the stowed position, the tether 420 is almost completely wound around the spool 412 to pull the sensor or collection payload (e.g., 114a) against the back portion 436 of the bracket 430. In the deployed position, the tether 420 is partially or fully unwound from the spool 412, and the lack of tension in the tether allows the sensor or collection payload (e.g., 114a) to freely move away from its stowed position at the back portion 436 of the bracket 430. While the torsional spring 432 is shown in this example, in other implementations, a second actuator or other spring-mechanism may be employed to actuate the bracket.

Referring to FIG. 4C, the bracket 430 is formed of an angled body 434 having the retaining back portion 436 configured to abut against a spool plate 438 and, in some embodiments, guide the tether 420 from the spool 412. The angle body 434 also includes an elongated payload support portion 440 configured to support the sensor or collection payload (e.g., 114a) when the bracket 430 is in the stowed position. The retaining back portion 436 may abut against the spool plate 438 when the spool 412 is in the initial position. In the initial position, the spool 412 is at the most retracted position.

In the example shown in FIG. 4C, the sensor or collection payload (e.g., 114a) includes a waterproof housing 452. As further explained with reference to FIGS. 5A-C below, the waterproof housing 452 is reconfigurable to retain a sensor or sensor head of a variety of sensors described herein and/or a uniform control system and front-end electronics for the signal acquisition of the sensor head.

In use, the actuator 414 is configured to cause the spool 412 to unwind and to move from an initial position to an extended position to release the sensor or collection payload (e.g., 114a) by unspooling the tether 420. As the sensor or collection payload (e.g., 114a) is released, and the tether 420 continues to unspool, the bracket 430 is configured to move, e.g., by gravity feed and/or the torsional spring, from a stowed position to the deployed position.

When moving from the deployed position to the stowed position, the actuator 414 is configured to cause the spool 412 to move from the tether from an extended position to its initial position, the course of which retrieves the sensor or collection payload (e.g., 114a) by pulling the top region of the sensor or collection payload (e.g., 114a) against the back portion of the bracket. The bracket 430 is caused to move from a deployed position to a stowed position by the force of the sensor or collection payload (e.g., 114a) being spooled up. The provided force to retrieve the sensor or collection payload (e.g., 114a) via the spool 412 and actuator 414 is greater than the force of the torsional spring 432 pushing the bracket towards the deployed position. This configuration provides an optimized mechanical design that employs a single actuator to operate the spool and the bracket, a technical benefit for a weight-constrained or weight-optimized aerial vehicle.

The apparatus 400 further includes a contact sensor 460 (e.g., a Hall effect sensor, a capacitance sensor, an optical sensor, a mechanical switch, and the like). The contact sensor 460 is configured to detect when the bracket 430 is in the stowed position. The contact sensor 460 provides a signal to control the actuation of the spool 412. When the bracket 430 moves from the deployed position to the stowed position (i.e., when retrieving the sensor or collection payload (e.g., 114a)), the contact sensor 460 is configured to output a signal that can be provided to the vehicle controller, or a cut-off circuit, to stop the rotation of the spool 412.

Example Deployment and Extraction Sequence. In the example shown in FIG. 4A-4B, the above-described sequence regarding apparatus 400 can be seen. FIG. 4A shows the deployment sequence, while FIG. 4B shows the stowing sequence. Image 401 of FIG. 4A shows the apparatus 400 with the bracket 430 in the stowed position, cradling the sensor or collection payload (e.g., 114a). In image 402, the spool is moving from the initial position to the extended position such that bracket 430 is in the process of moving from the stowed position to the deployed position. In image 403, the sensor or collection payload (e.g., 114a) is vertical with respect to the gravitational vector, and the sensor or collection payload (e.g., 114a) is in contact with bracket 430 for the last instant in the deployment sequence. In image 404, the bracket 430 is in the deployed position, and the sensor or collection payload (e.g., 114a) is hanging from tether 420. In image 405, the sensor or collection payload (e.g., 114a) is not visible because it is being deployed into a liquid medium for data gathering.

In the example shown in FIG. 4B, the retrieval process is shown, which is essentially a reverse of the deployment process. In image 406, the sensor or collection payload (e.g., 114a) is being retrieved while the spool is moving from the extended position to the stowed position. In image 407, the sensor or collection payload (e.g., 114a) abuts the bracket 430, beginning the process of moving the bracket 430 from the deployed position to the stowed position. In image 408, a transition point is shown wherein the sensor or collection payload (e.g., 114a) continues to move the bracket 430 from the deployed position to the stowed position. Image 409 shows a similar transition point as image 408, where the bracket 430 is almost in the stowed position. Once the sensor or collection payload (e.g., 114a) is fully retrieved, the apparatus 400 will be back in the original state shown in image 401, ready to start the process again.

Example Remote Autonomous Sensor

Figure 5A:
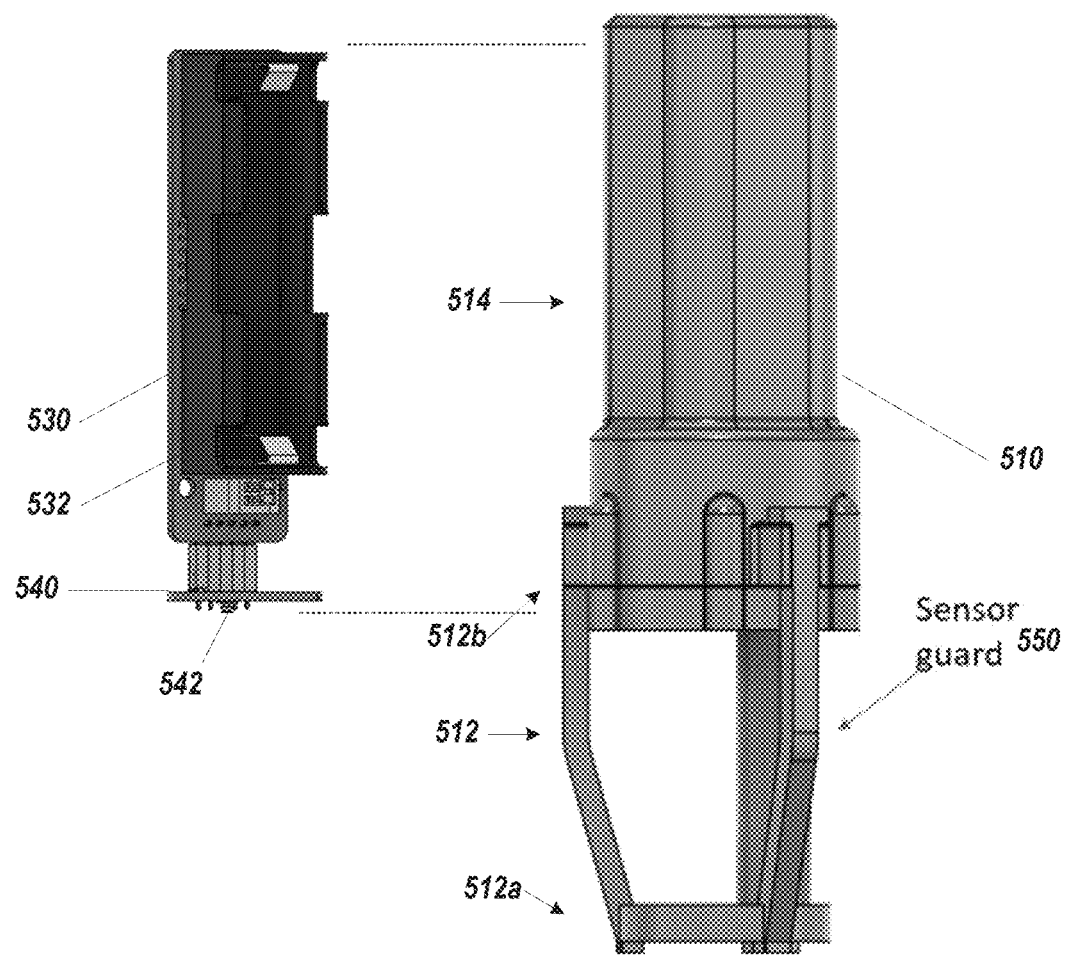
FIGS. 5A, 5B, and 5C are each a diagram of a mechanical configuration of example sensor or collection payload devices in accordance with an illustrative embodiment.
Figure 5B:
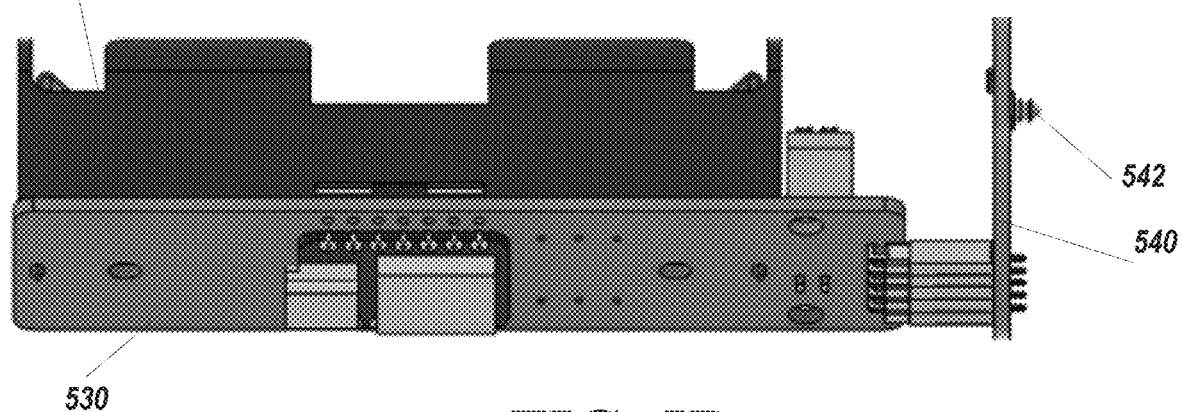
Figure 5C:
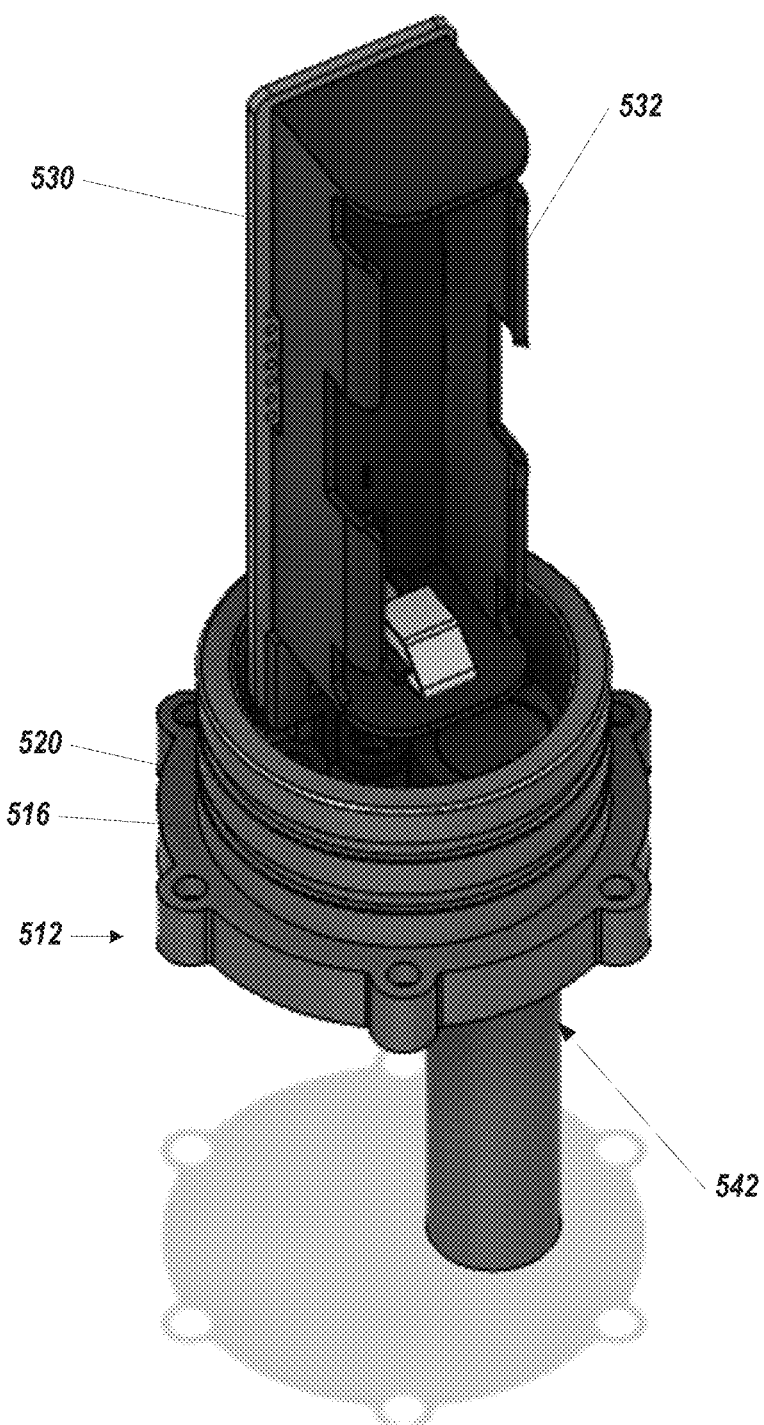
Figure 5D:
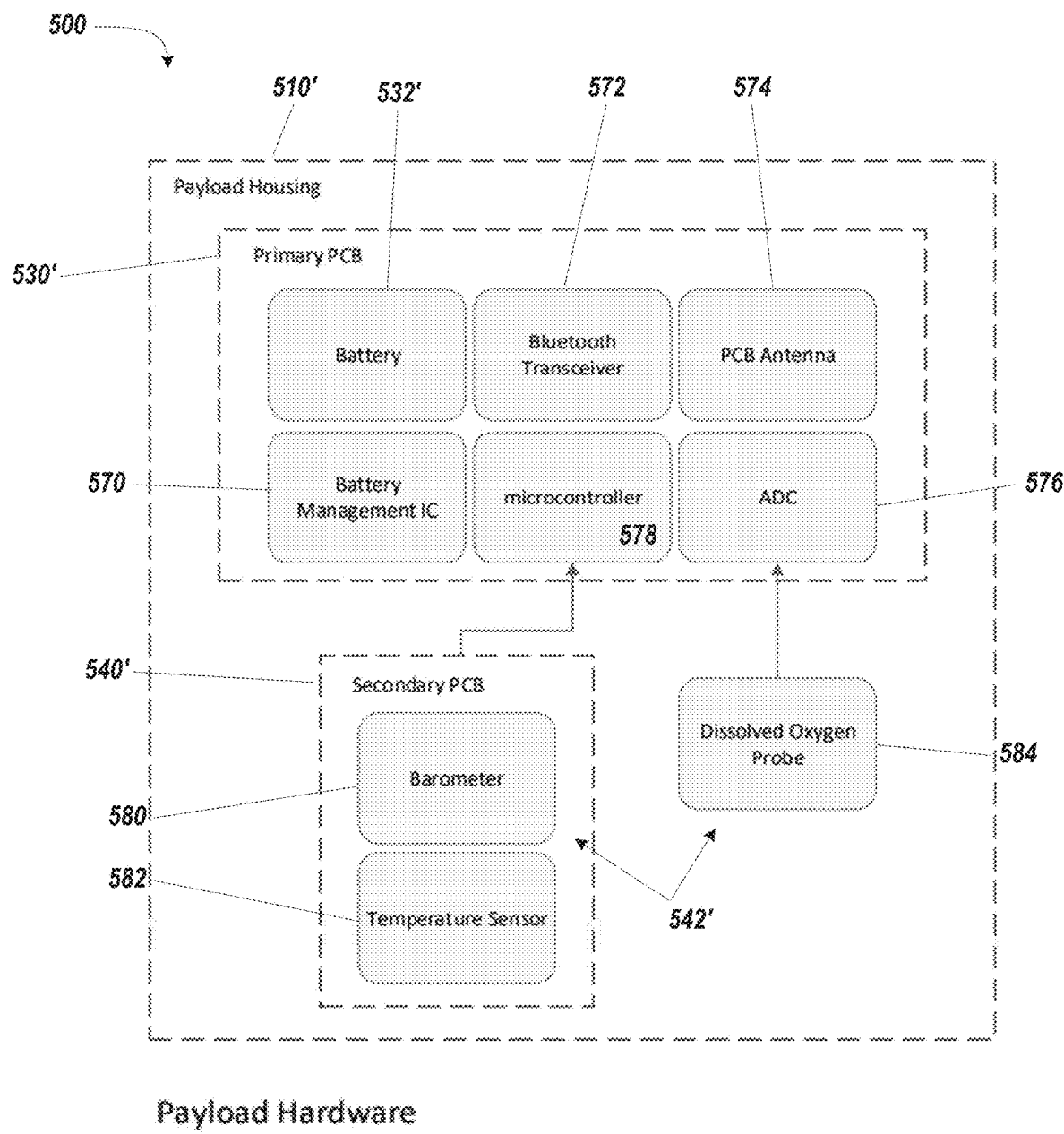
FIG. 5D is a diagram showing an example system configuration of the example sensor or collection payload devices of FIGS. 5A-5C in accordance with an illustrative embodiment.

FIGS. 5A, 5B, and 5C are each a diagram of a mechanical configuration of example sensor or collection payload devices (e.g., 114a) in accordance with an illustrative embodiment. FIG. 5D is a flowchart showing an example system configuration of the example sensor or collection payload devices of FIGS. 5A-5C in accordance with an illustrative embodiment.

The sensor or collection payload (e.g., 114a) may be the same payload described in relation to FIG. 1A, 1B, or 4A-4E. The sensor or collection payload (e.g., 114a) is configured to be coupled to a tether as part of, and deployable from, the winch assembly apparatus (e.g., 400), e.g., as described in relation to FIGS. 4A-4E above.

In the example shown in FIG. 5A-5C, the sensor or collection payload (114a) is configured as a remote autonomous dissolved oxygen (DO), temperature, and pressure sensor system. In FIG. 5A, the payload 114a includes a housing 510, an electronic circuit board 530, a power source 532, a sensor unit 540 (e.g., for DO sensor head, temperature sensor, and pressure sensor), and a sensor guard 550. The waterproof housing 510 includes a sensor portion 512 (e.g., a sensor head having the sensor device), defining a top region, and a control/circuit portion 514 514, defining a bottom region; the two are removably coupled to one another. The sensor portion 512, in the example shown in FIG. 5A, includes a top/first portion side 512a and a bottom/second sensing portion side 512b to which the sensor head may be placed therebetween. In some embodiments, the sensor portion 512 includes a protrusion region that extends past the top/first portion side 512a that houses the sensor head. In the example shown in FIG. 5A-5C, the sensor portion 512, and control/circuit portion 514 include corresponding threads 516 to releasably attach to one another and form a watertight seal. The sensor portion 512 or the control/circuit portion 514 may include one or more rubber seals 520 to improve the waterproof seal of the housing 510.

Referring to FIG. 5A, the sensor portion 512 is coupled to an electronic circuit board 530 located at the control/circuit portion 514. The power source 532 (e.g., batteries) is in housed in the control/circuit portion 514 (to provide a bottom-heavy center of weight) and is in operative communication with the electronic circuit board 530. The power source 532 is, preferably, a battery, but in other implementations, it may be any other means of providing power to the electronic circuit board as described herein in relation to FIGS. 1A and 1B.

The sensor unit 540 includes one or more sensing elements and is in electronic communication with the electronic circuit board 530. The housing may include the sensor guard 550, which is attached to the sensor portion 512 and partially surrounds the sensor unit 540. The sensor guard 550 may keep a leak from damaging the sensor unit 540.

While the example shown in FIGS. 5A-5C illustrates the sensor unit of the payload 114a having a temperature sensor, a dissolved oxygen (DO) sensor, and a pressure sensor, the sensor unit may include other sensors as described herein, e.g., to acquire or measure data about a liquid medium and/or trace compositions therein. The combination of sensors, particularly pressure sensor and the like, facilitates analysis of the stratification of depths in the liquid medium. An array of data points may be collected, e.g., for temperature and DO, alongside the pressure to ascertain or map the measurements to the depth of the liquid medium, which can be aggregated to provide a depth profile of the acquired measurements.

In use, the sensor or collection payload (e.g., 114a) is configured to be deployed and released into a liquid medium. The electronic circuit board 530 includes instructions for performing a data gathering task and memory for storing the data gathered by the sensor unit 540. Once lowered into the liquid medium, the sensors 542 measures and collect data about the liquid medium over a predefined period of time (e.g., the temperature and DO of pond water for a period of 8 seconds or the DO data at various depths/pressures over a 15 second time period). All data gathered by the sensor 542 is, preferably, communicated to and stored on the electronic circuit board 530. Then, once the payload 500 is retrieved (e.g., by the apparatus described in FIGS. 4A-4E above), the electronic circuit board 430 communicates the data to a different system of a topside module.

FIG. 5D is a diagram showing an example system configuration of the example sensor or collection payload devices of FIGS. 5A-5C in accordance with an illustrative embodiment. In use, the example sensor or collection payload (e.g., 114a) is shown in FIGS. 5A-5C may include an electronic system 500 shown in FIG. 5D. Diagram 500 includes like-elements of the above example of FIGS. 5A-5C, such as payload housing 510' (corresponding to housing waterproof housing 510 in FIG. 5A). The sensor may include a primary PCB 530' that is disposed within payload housing 510'.

In an example, the primary PCB 530' is an ESP32S configured to consume less power than ESP32 LoRA (used in the topside module) while supporting multiple analog-to-digital converter (ADC) channels and WiFi links. The communications between the topside and the sensing modules may be achieved using an ESP-NOW link, or Bluetooth. ESPNOW is a connectionless communication protocol that supports short packet transmission (up to 250 bytes) between ESP32 boards. This protocol can facilitate multiple devices talking to each other using the 2.4 GHz RF circuits on the ESP32x boards without the WiFi protocol. The lightweight link (e.g., ESP-NOW link) may reduce or eliminate the need for a physical, electrical connection between the topside controller and the sensing modules, thereby simplifying the winch system.

Primary PCB 530' includes a battery 532', battery management IC 570, Bluetooth transceiver 572, PCB Antenna 574, ADC (Analog-to-Digital Converter) 576, and microcontroller 578. A secondary PCB 540' includes sensors 542', including a barometer 580 and temperature sensor 582, and operatively connects to the microcontroller 578 or the primary PCB 510'. Another sensor 542' is the dissolved oxygen probe 584, which is in electrical communication with the ADC 576.

The battery 532' and battery management IC 570 provide power to the elements in the sensor or collection payload (e.g., 114a) while it engages in data collection. The battery 532' can be replaced or recharged once data collection is complete.

As described above, the sensor or collection payload (e.g., 114a) is lowered into a liquid medium to gather data. To start this process, the primary PCB 530' is configured to receive signals from the topside module/edge controller (e.g., 115; see also a description with reference to FIGS. 8 and 9A-9D). The signals from the topside module/edge controller are sent and received by the PCB antenna 574 or a Bluetooth (BLE) receiver 572, depending on the type of signal sent/received. That signal is processed through the microcontroller 578, which can direct the sensors 542' and the secondary PCB 540' to begin collecting and storing data. Each sensor 542' may collect data over a predetermined period of time, storing the data until the sensor or collection payload (e.g., 114a) exits the liquid medium. The microcontroller 578 may process and store data from the barometer 580 and temperature sensor 582, while the ADC 576 converts the signals from the dissolved oxygen probe 584 before sending them to the microcontroller for storage.

Once the sensor or collection payload (e.g., 114a) can communicate with the topside module/edge controller once again (e.g., a Bluetooth link is reestablished outside of the liquid medium), then one of the Bluetooth transceiver 572 or PCB antenna 547 will send the collected data to the topside module/edge controller for further processing and storage. See FIGS. 8 and 9A-X and the corresponding description for those processing details.

Figure 7A:
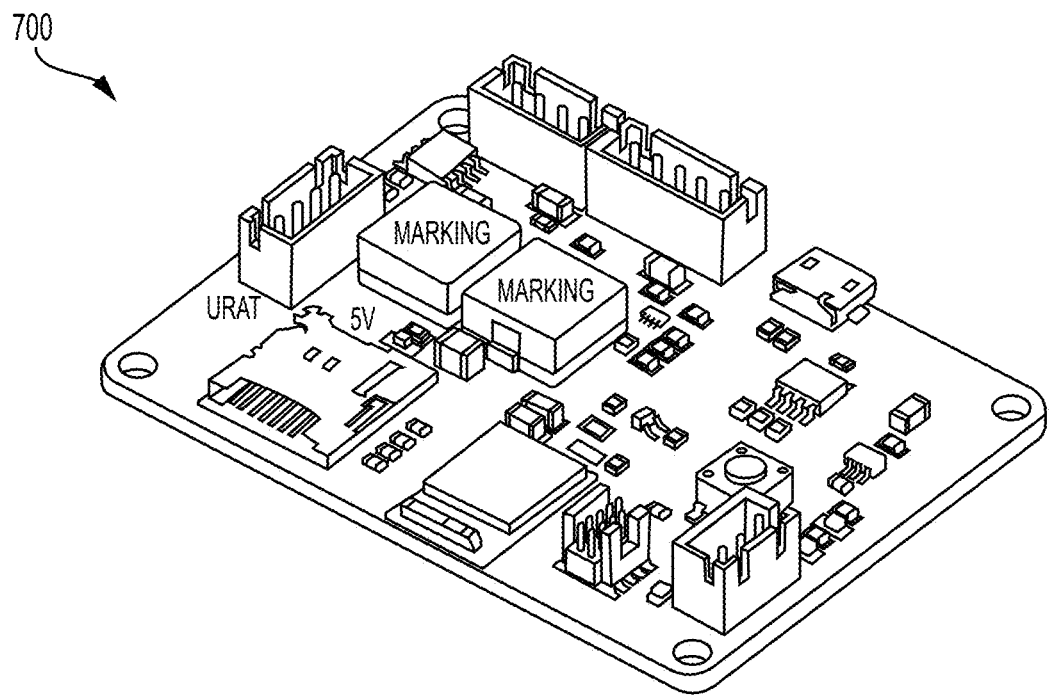
FIGS. 7A and 7B each show a diagram of a topside controller of an aerial/amphibious sensing platform in accordance with an illustrative embodiment.
Figure 7B:
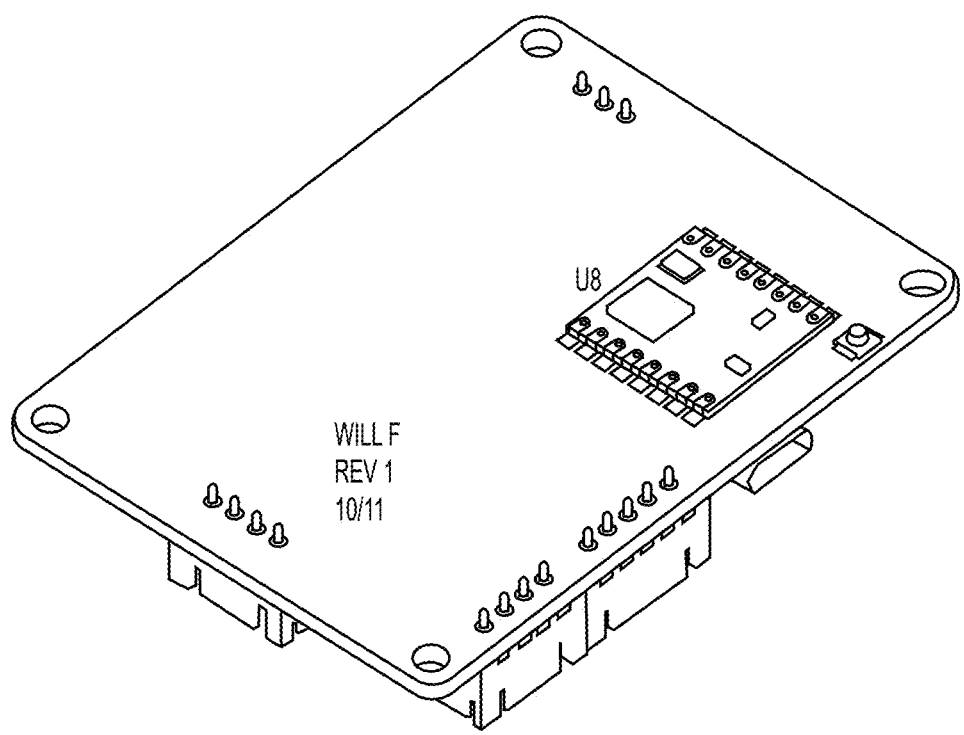

In the example shown in FIGS. 7A-B, an example embodiment of a topside controller (or site controller) is shown. The topside controller 700 is configured to the housing of the topside module, e.g., mounted onto the UAAV 112a. The topside controller 700 is configured to send signals between a sensor or collection payload (e.g., 114a) and a site controller (e.g., 113). An example of the communication and signaling process is provided in FIG. 8.

Figure 8:
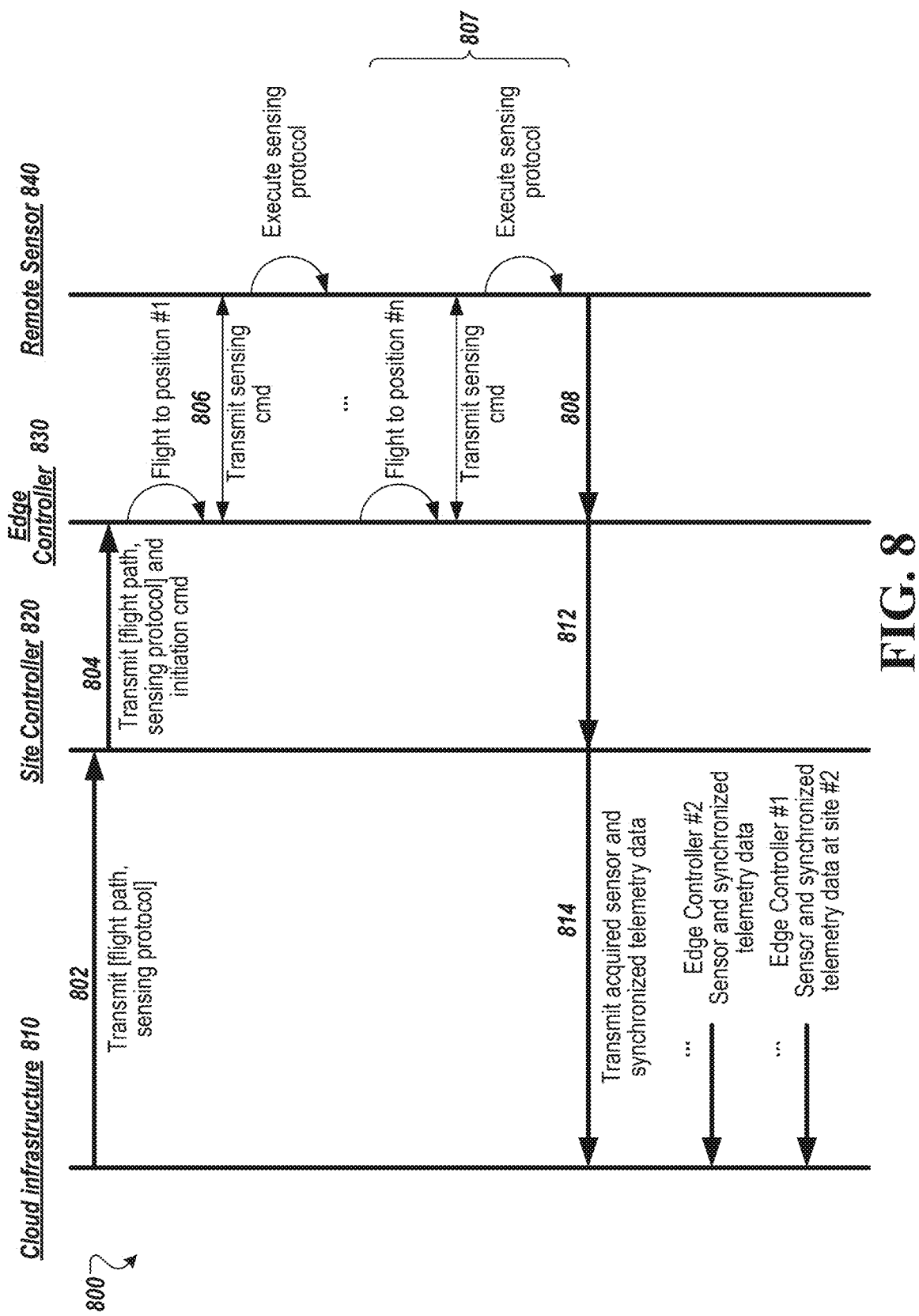
FIG. 8 is a diagram showing the operation of the example sensing platform system and infrastructure in accordance with an illustrative embodiment.

FIG. 8 is a diagram showing operation 800 of the example sensing platform system and infrastructure in accordance with an illustrative embodiment. In the example shown in FIG. 8, a cloud infrastructure 810 (previously shown as 107), site controller 820 (e.g., previously described as a site controller 113), edge controller 830 (e.g., previously described as edge controller 115), and remote sensor 840 (previously shown as sensor and collection payment 114a) are shown.

In FIG. 8, operation 800 initiates with the cloud infrastructure 810 transmitting data sensing or collection instructions 802 having at least one of flight path data, sensing or collection protocols, etc., to the site controller 820. The site controller 820 receives and processes the instructions 802 and transmits the same or commands, derived therefrom, as command signals 804 to the appropriate edge controller(s) 830, e.g., mounted to a UAAV platform (e.g., 112a) or other vehicle sensing system (e.g., 112b). Among other edge controllers (e.g., for other vehicle systems), the edge controller 830 for a UAAV platform receives the command signal 804 and flies to the respective positions over the body of water, as provided in the flight path details. Once at the geographic position of interest, the edge controller 830 then directs 806, via a wireless command, the remote sensor to initiate execution of its sensing protocol prior to the remote sensor being submerged and then extended, via winch operation, to the desired depth. The sensing is then performed at the remote sensor 840 in a predefined sequence (e.g., based on time) while the actuation of the winch by the edge controller 830 is performed in a similar sequence (e.g., based on time). At the end of the sensing sequence, the remote sensor 840 can be extracted from the body of water, and the edge controller 830 directs the UAAV platform a next position. The process can be repeated (807) for n number of positions.

In between scanned geographic positions, or at the end of the sensing protocol, the remote sensor can provide (808) the data to the cloud infrastructure 810. FIG. 8 shows the data being send to the cloud infrastructure 810 through the edge controller 830 (see transmit 812) and the site controller 820 (see transmit 814). In the example shown in FIG. 8, the cloud infrastructure 810 can receive similar data acquired by the same UAAV at a second instance (shown as site #2) or from other UAAV or other sensing vehicles described herein. In some embodiments, the site controller 820 may compile data from multiple edge controllers 832 before sending the aggregated data to the cloud infrastructure 810. In other embodiments, the site controller 820 relays the data from a received edge controller 830.

Once at the cloud infrastructure 810, or site controller 820, a user can view and/or analyze the acquired data. A user may also initiate data collection processes from the cloud infrastructure, starting the process over again.

Synchronized Autonomous Sensing Operation

Figure 9A:
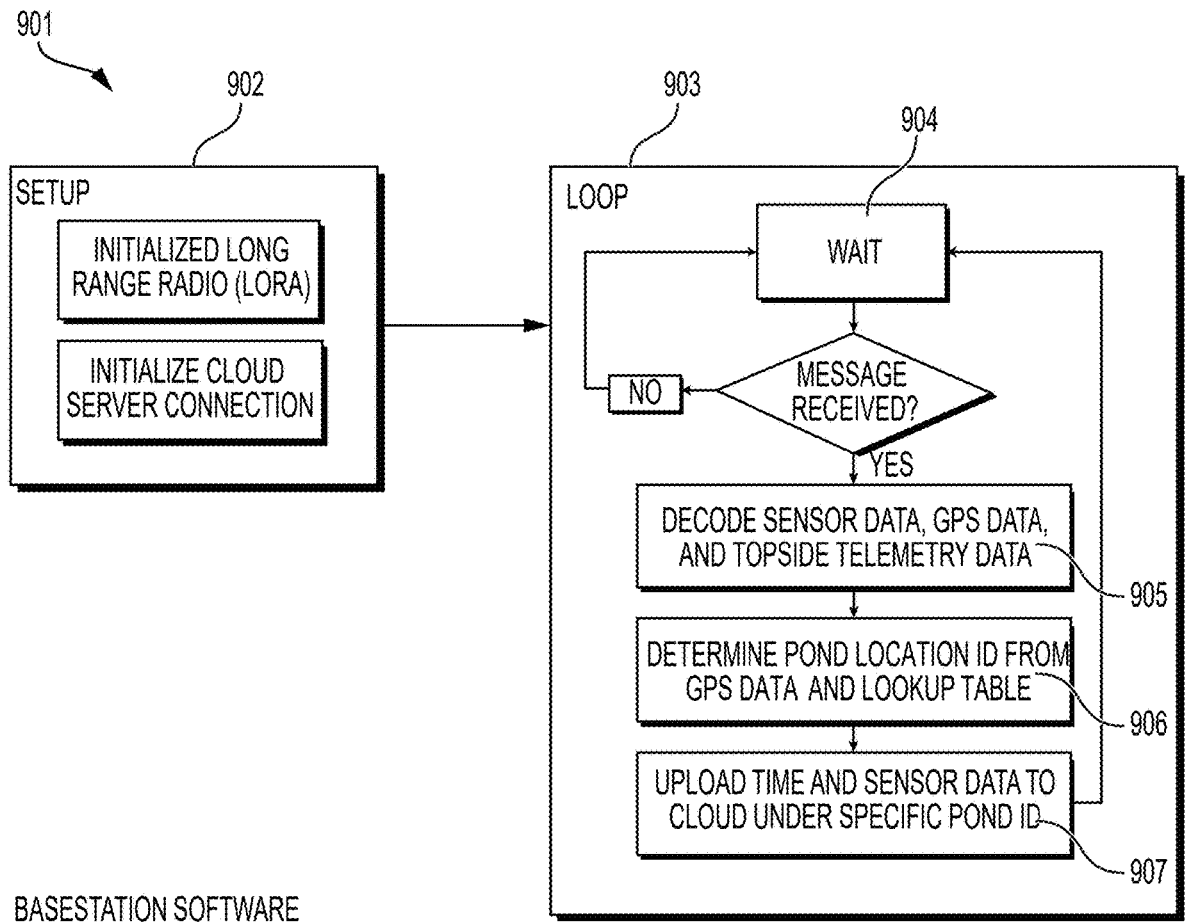
FIGS. 9A, 9B, and 9C are diagrams each showing a flowchart of the operations of an example base station system, the aerial/amphibious sensing platform, and remote sensors of the example sensing platform system and infrastructure in accordance with an illustrative embodiment.
Figure 9B:
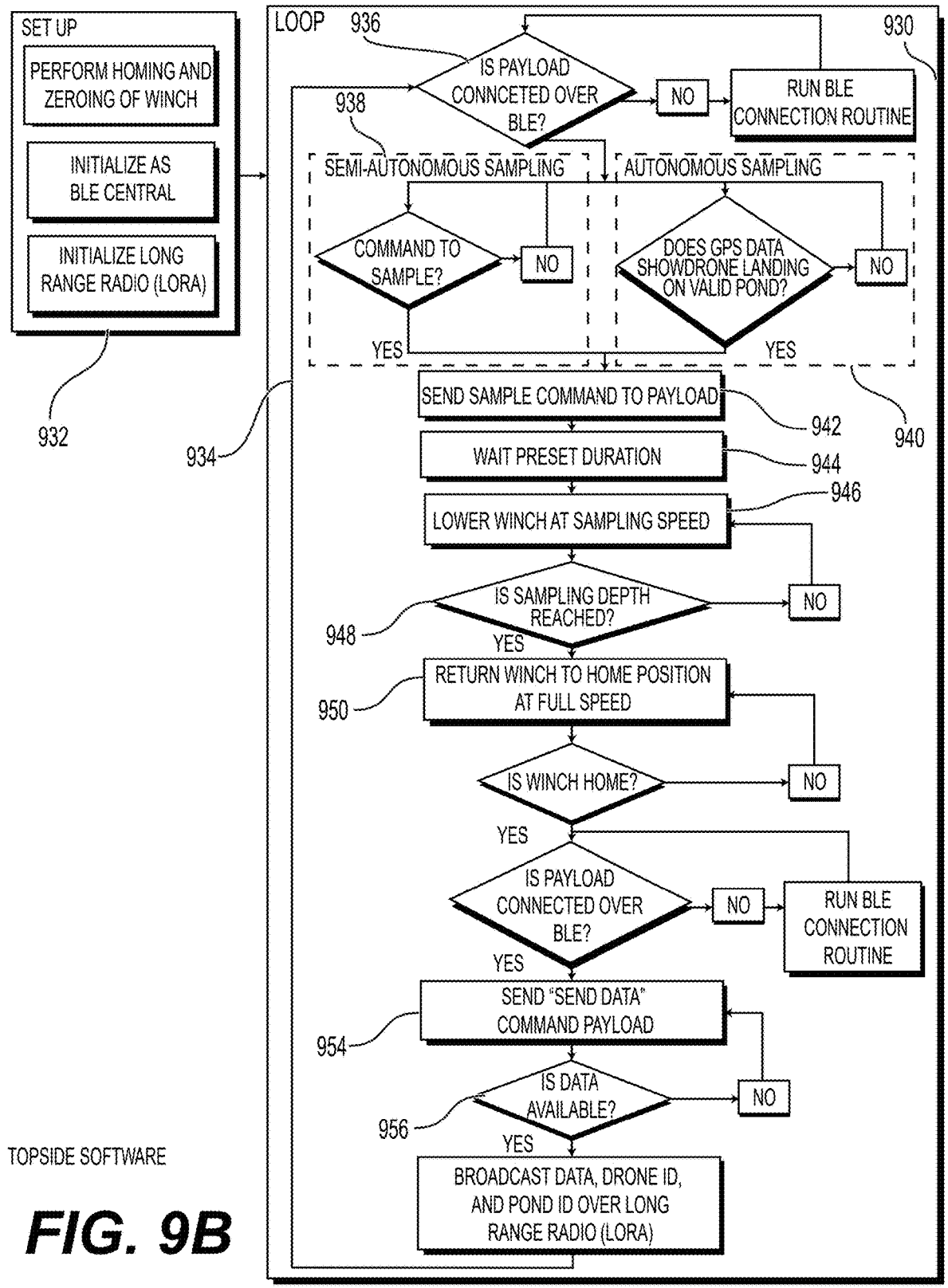
Figure 9C:
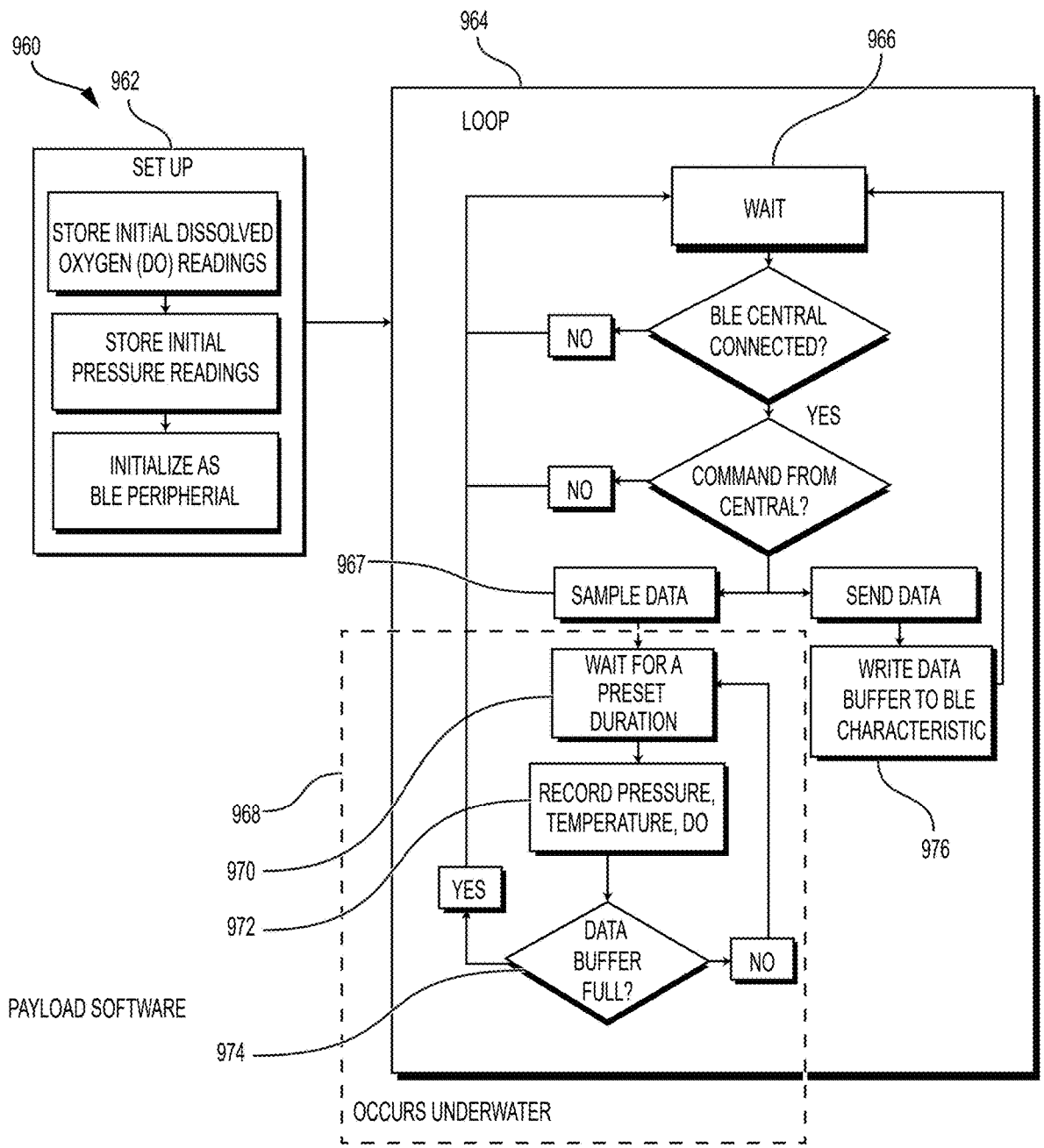

As noted above, FIGS. 9A, 9B, and 9C are diagrams, each showing a flowchart of the operations of an example base station system, the aerial/amphibious sensing platform, and remote sensors of the example sensing platform system and infrastructure in accordance with an illustrative embodiment. FIG. 9A shows an example local operation for a base station. FIG. 9B shows an example local operation for a site controller. FIG. 9C shows an example local operation for the edge controller.

Base Station Operation. In the example shown in FIG. 9A, after the setup sequence 902, the base station performs the base station loop 903. The base station loop 903 includes a waiting step 904 for a message to be received. Once a message is received, the base station is configured to (i) decode sensor, GPS, data, and telemetry data (action 905), (ii) determine pond location ID from GPS data and lookup table (action 906), and (iii) upload the time and sensor data to the cloud with a specific pond ID (action 907).

Top-Side Operation. In the example shown in FIG. 9B, the topside operation includes a setup operation 932 and a runtime operation 930. The setup operation 932 includes (i) performing homing and zeroing operation of the winch (to ensure a correct starting positioning), initializing short-range communication to communicate with the remote sensor (shown as BLE central), and initializing long-range communication to communicate with the site controller (shown as LoRa).

The runtime operation 930 includes a loop (see 936) to ensure that the short-range communication with the remote sensor is established. Depending on whether a semi-autonomous or autonomous sampling operation is selected, the runtime operation 930 includes waiting for a command to initiating sensing (see "semi-autonomous sampling") or determine if the GPS shows the UAAV being located at the correct location following a global command being received (see "autonomous sampling").

Once the command is set, the runtime operation 930 includes sending (942) sampling command to the payload, waiting for a preset duration (944), and then lowering the winch in a controller manner (see 946, 948) by incrementally changing the winch position (946) at a pre-defined sampling speed until a position is reached (948). The process 946, 948 may be repeated for a number of sensing operations to generate a sensing data set along a depth profile. After the sensing protocol is completed for a given location, runtime operation 930 directs the winch to return the remote sensor to the home or initial position (948).

Once the winch has been retracted (952) to its home position, the runtime operation 930 may direct the UAAV to reestablish short-range communication with the remote sensor and send (954) a "send data" request in a loop until the data buffer of the remote sensor is empty. The runtime operation 930 includes broadcasting the data, drone ID, and pond ID over the long-range communication to the cloud infrastructure.

Figure 9D:
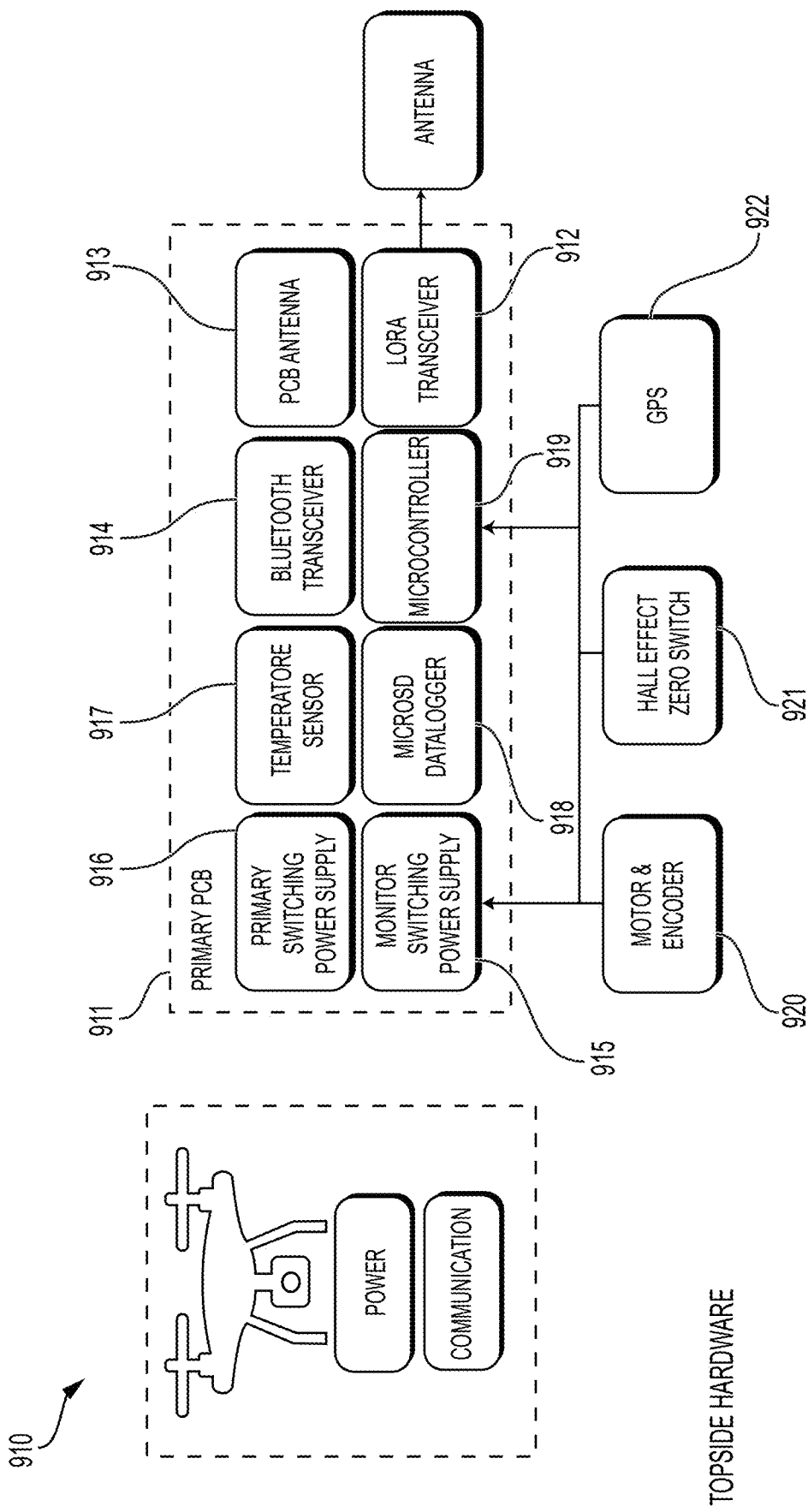
FIG. 9D shows a diagram of a topside controller of an aerial/amphibious sensing platform in accordance with an illustrative embodiment.

Example Topside Controller. FIG. 9D shows an example hardware configuration 910 of the top controller. In the example shown in FIG. 9D, the hardware configuration 910 includes a main PCB 911 that includes a power supply 916, a temperature sensor 917, a Bluetooth transceiver (914), a PCB antenna (913), a motor switching power supply 915, a datalogger 918, a microcontroller 919, and a long-range transceiver 912.

The LoRa transceiver 912, PCB Antenna 913, and Bluetooth transceiver 914 may be configured to communicate with antennas on other modules (e.g., communicating with the sensor or collection payload (e.g., 114*a*) or the site controller). In some embodiments, the LoRA controller is an ESP32 LoRa controller configured with WiFi, LoRa, and Bluetooth. The ESP32 LoRa controller may communicate with the topside controller using the ESP-NOW link. In another example, SIYI 2.4G Datalink may be used, which can support video links up to 15 km range.

The primary switching power supply 916 is configured to supply power to the topside controller and other UAAV electronics. The motor switching power supply 915 is configured to supply power to the motor and encoder 920 is located external to the primary PCB 911.

The UAAV includes a motor 920, the contact sensor 921 (shown as Hall effect switch 921), and GPS 922; these modules 920, 921, 922 are operatively coupled to the microcontroller 919 to receive runtime feedback data to execute the operation described in FIG. 9B.

The motor and encoder 920 may provide motor output information and motor position. The contact sensor 921 provides information when the remote sensor is in a fully extracted position. Together, the microcontroller 919 and motor and encoder 920 can communicate a start or stop signal to the motor switching power supply 915 to stop the motor on the topside module.

FIG. 9C shows operations 960 at the remote sensor (e.g., sensor or collection payload (e.g., 114*a*)). The operation 960 includes a setup operation 962 and runtime operation 964. The setup operation 962 includes (i) storing initial dissolved oxygen reading, (ii) storing initial pressure readings, and (iii) initializing short-range communication to the topside controller (e.g., using BLE communication). The runtime operation 964 includes ensuing (966) that short-range communication is established with the topside controller. The communication is established, the runtime operation 964 includes sampling (967) data, waiting (970) for a present duration, then recording (972) the measurement (e.g., pressure, temperature, and DO, in this example). Subsequently, once the provided sensing protocol is complete, the runtime operation 964 includes writing (976) the data to the short-range communication buffer to transmit to the topside controller. If the data buffer becomes full (974), the runtime operation 964 includes going back to the initial stage (966).

The timed sequences of FIGS. 9B and 9C provide synchronized operation such that the sensing or collection protocol for the sampling or collecting operation is synchronized to the plurality of positions corresponding to a different (e.g., pre-defined) water depth. This facilitates sampling at multiple depths with high precision and accuracy while the remote sensor and the vehicle are each subjected to their respective movements for different environmental forces.

Experimental Results and Examples

A study was conducted to investigate a framework for monitoring aquaculture farms. There have been attempts to reduce labor costs by automating aquaculture pond monitoring. Most of these solutions employ buoy-based monitoring stations that measure pond-water quality parameters such as DO, temperature, pH, etc. Sensor data can be sent via WiFi or cellular link to a control center for analysis [11, 13, 14, 16-19, 21]. However, these stationary instruments deployed in the water are difficult to maintain due to biofouling. In addition, sensor buoys are an obstruction in the pond during harvest as they must be removed or lifted over the seine. Another drawback is that while these solutions may provide high temporal sampling frequency but they lack spatial sampling density, which may be even more important to evaluate the water quality of the ponds.

Overview of the HAUCS Framework: The overarching goal of HAUCS was to relieve human operators from the most labor-intensive, time-consuming, and expensive operations in aquaculture farming operations through a group of cooperative robotic sensing and actuator platforms. With support from the National Institute of Food and Agriculture (NIFA), USDA, through the Ubiquitous Collaborative Robots (NRI-2.0) program, the project was launched in the Spring of 2019.

Figure 10:
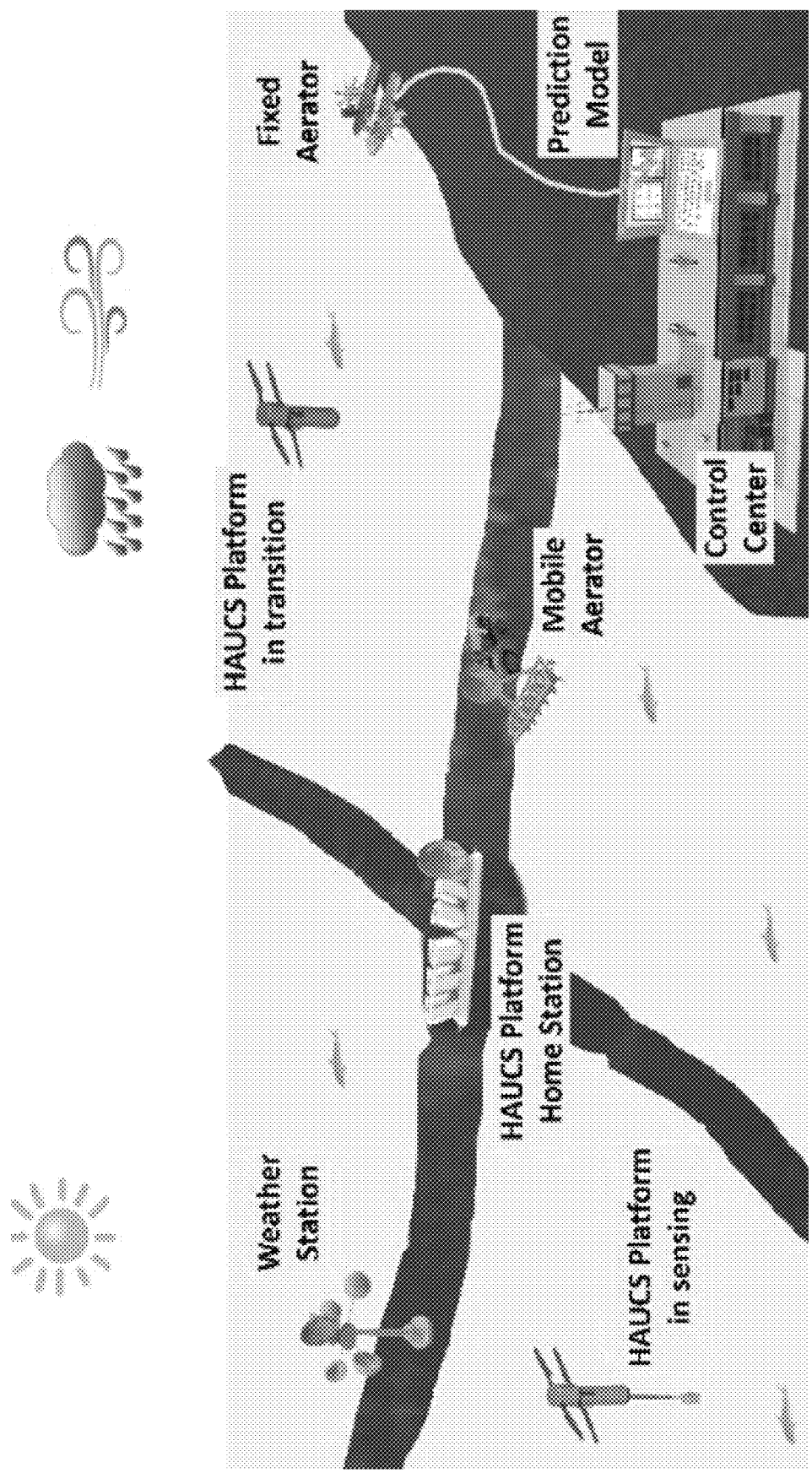
FIG. 10 is a diagram showing an example operational scenario in accordance with an illustrative embodiment.

HAUCS was a framework that aimed to achieve collaborative monitoring and decision-making on aquaculture farms of varying scales. The HAUCS framework consisted of the three basic modules: aero-amphibious robotic sensing platforms integrated with underwater sensors; land-based infrastructure (e.g., weather stations and home stations that provide automated charging and sensor cleaning); and back-end modeling and processing infrastructure, in particular, an ML-based water quality prediction model. A LoRa communication network was employed to connect the different components in HAUCS. The communication hub may also be integrated with land-based components to overcome obstacles, such as treelines [IEEE IoT]. HAUCS was capable of automated sampling at frequencies relevant for accurate prediction of water quality variation (e.g., hourly diel readings), providing significant advantages in speed, cost, resource efficiency, and adaptability over traditional water quality measurement systems. Each HAUCS autonomous unmanned platform (AUP) consisted of an unmanned robotic vehicle and submerged underwater sensors. The HAUCS AUPs covered the entire farm in a reasonable period with high location precision. Data from the lightweight underwater sensors attached to the vehicle, such as DO sensors, was sent to the farm control center via a radio link during sensing operations. An ML-based data analytics engine analyzed the sensor data to predict pond conditions at the backend. Sensor data from all the ponds on the farm and the associated weather data were used to train the prediction model. The model prediction can, in turn, guide other instruments to mitigate an emergency situation (e.g., turning on a fixed aerator or instructing human operators to move mobile emergency aeration equipment into place in a pond). The overall concept of operations is illustrated in FIG. 10.

This highly scalable framework converts aquaculture farm operations to an "Internet of Aquaculture." Compared with the state-of-the-art solutions, the advantages of HAUCS include: Improved scalability-compared with the sensor buoys; HAUCS design can be easily adapted to farms of varying scales; Broad spatial coverage-capable of realizing novel sensing patterns to cover different areas on a large pond; to provide more accurate reporting of pond conditions; Mitigated biofouling-avoiding sensors in bio-productive water.

Figure 6A:
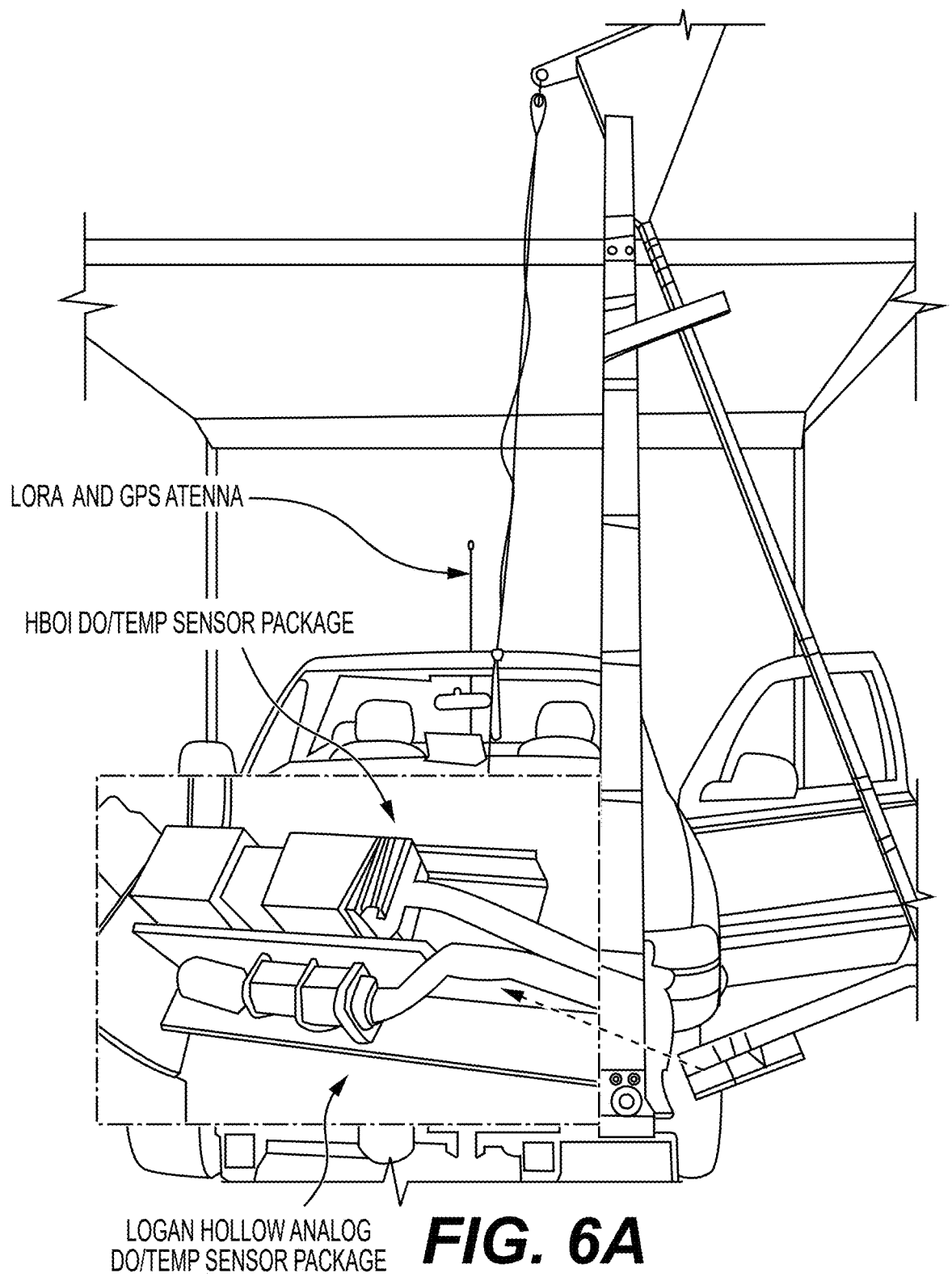
FIGS. 6A-6B are photographs of a truck-based sensor system and components thereof fabricated in a study in accordance with an illustrative embodiment.

Initial HAUCS prototype and deployment efforts: The truck-based sensor system (see FIG. 6A) was configured to provide an automated DO data acquisition system compatible with the current monitoring practice on the farm; to evaluate the infrastructure needed for future deployment of HAUCS platforms on the farm; and finally, to collect high-quality data to support prediction model development. This prototype sensor system consisted of a mobile data acquisition system (DAQ) and a central server. The mobile DAQ was installed on the farm sensing truck, side by side, with the DO sensor used in the farm operation at the Logan Hollow Fish Farm. See the figures immediately below showing the DO sensing truck with the HBOI sensor head co-mounted with the original DO sensor. The figures also show HBOI sensors mounted side-by-side with Logan Hollow sensors and the in-truck control unit. The central server was located inside the farm manager's office.

Figure 6B:
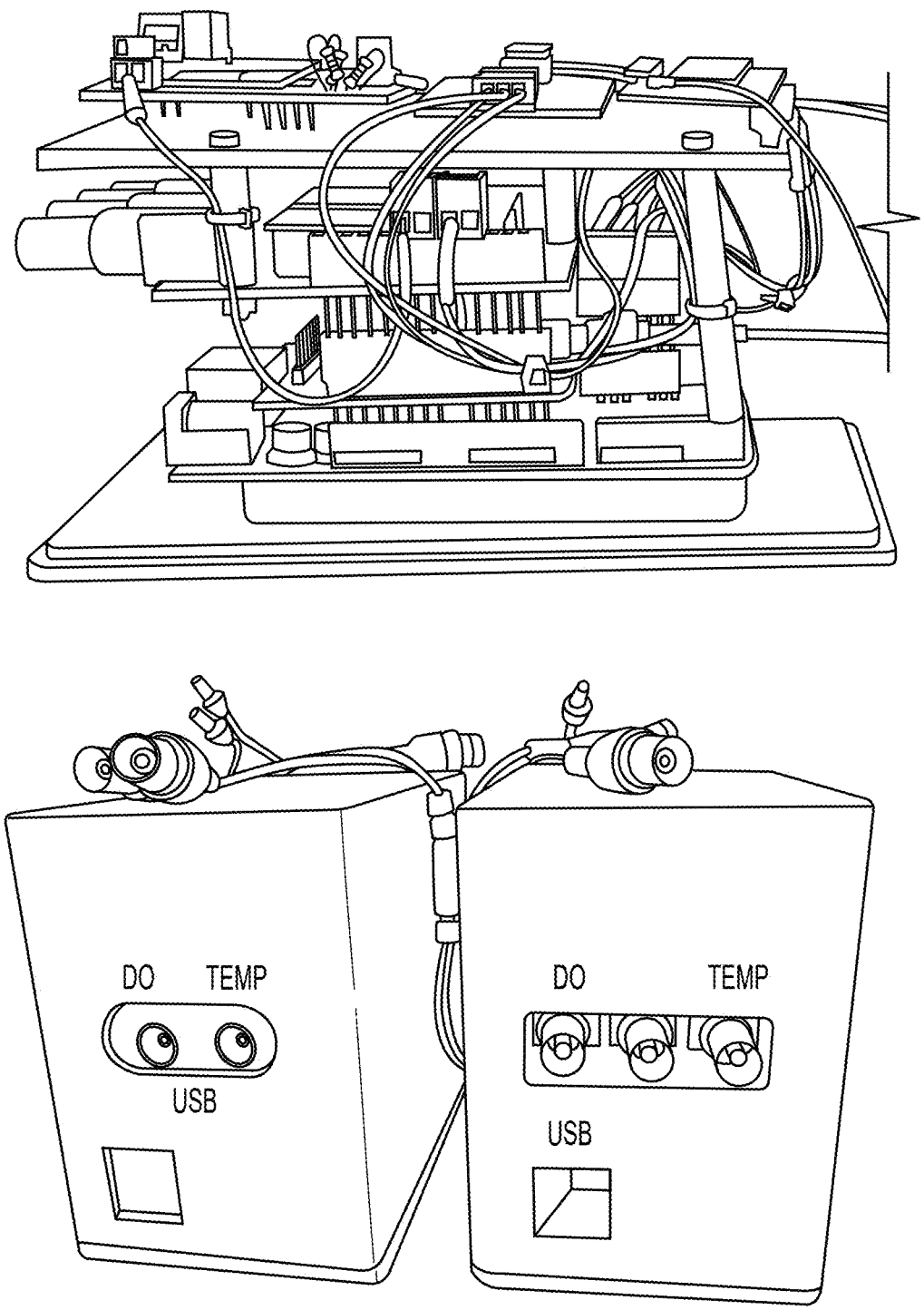

FIG. 6B shows the sensor control system comprising an Arduino Mega integrated with Atlas Scientific™ DO and temperature shields which simplify the integration of the sensor with the backend controller. In addition to the sensor shields, a GPS shield was used to associate with the pond being sampled. For communication, a Dragino LoRa shield was used to stream DO and temperature sensor data to the server in the farm manager's office. The LoRa antenna was mounted on a pole at the back of the truck.

Development and Field Demonstration of Drone-based HAUCS Sensing Payload

Development of Drone-based HAUCS Sensing. For this aspect, the study adopted the Swellpro Splashdrone 3+ (https://www.swellpro.com/waterproof-splash-drone.html) for payload integration. Splashdrone (see FIG. 6C) is a waterproof drone that is surface buoyant. In addition, the vendor provides API to support the integration of external logic with the drone in the near future. This will be highly desirable for the future implementation of environmental adaptive path planning algorithms [Srijita conference paper]. However, one important insight the study uncovered in the process of the project is that instead of being locked into certain platform designs, the HAUCS sensing payload should be platform neutral. While this study, with the new sensing payload, is targeted an aerial drone, it can be easily adapted to other platforms, such as ground vehicles (i.e., all-terrain vehicles or trucks) or unmanned surface vehicles.

The payload had two subsystems: a topside module that interfaces with the platform (aerial drone in this case), and the sensing module contains the sensors. The two modules were connected with a winch that will be released to allow the sensors to go underwater during the sensing operations. See below the platform-neutral sensing payload integrated with the Splashdrone.

Figures 6C, 6D:
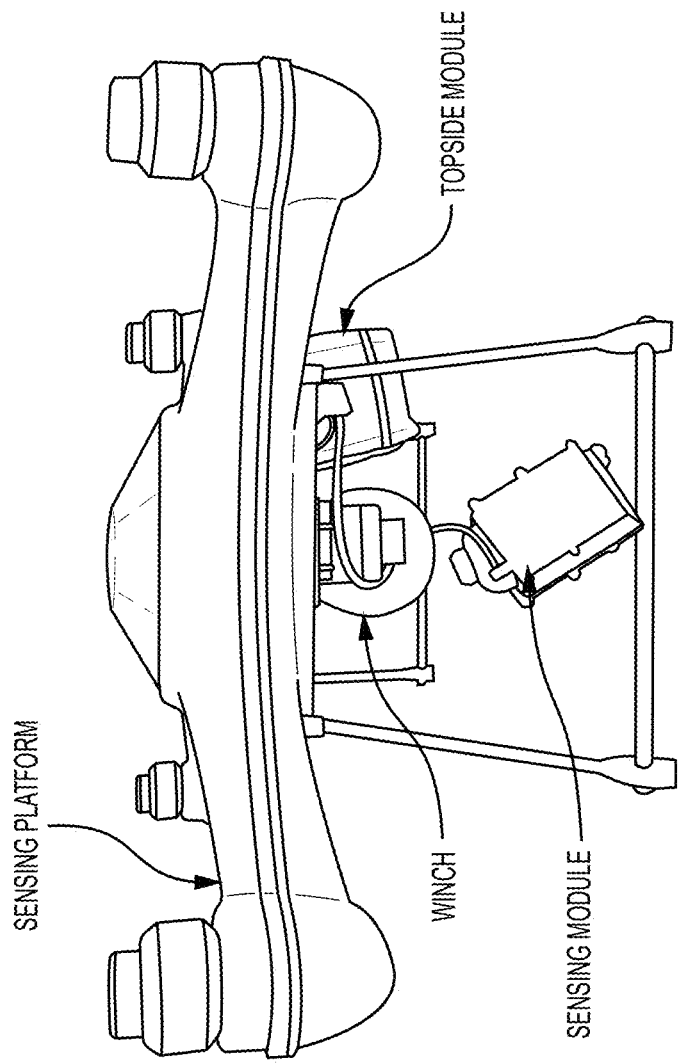
FIGS. 6C-6H are photographs of a waterproof aerial drone system fabricated in a study and components and operations thereof in accordance with an illustrative embodiment. In particular.
Figure 6E:
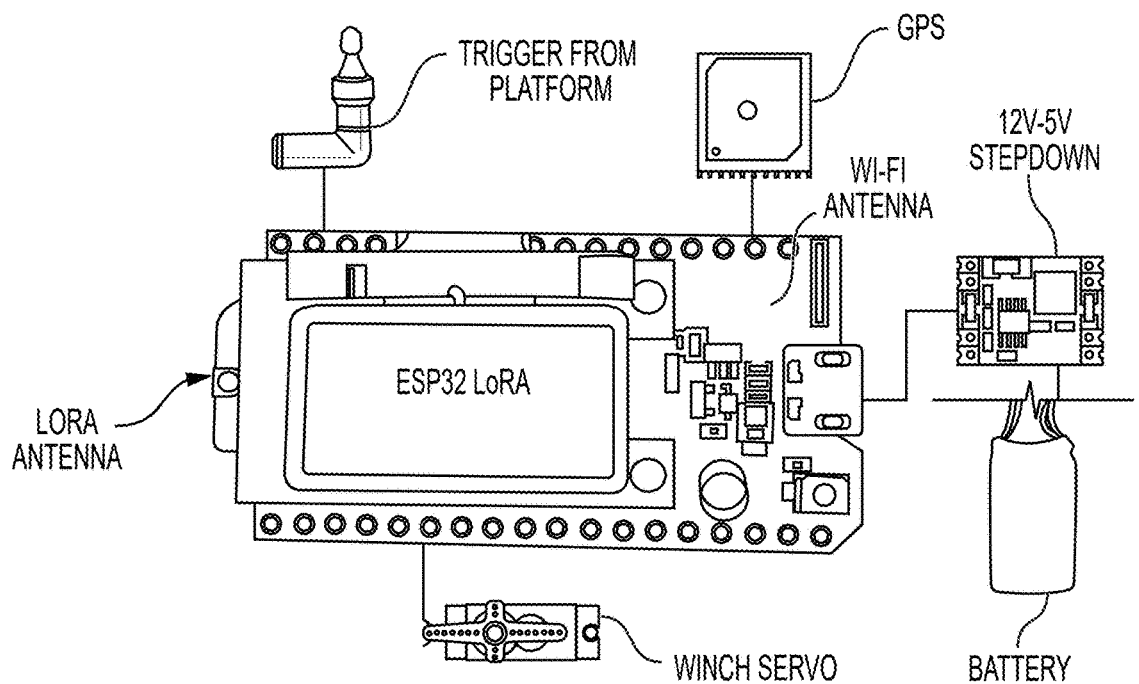

The topside was the gateway between the sensing module and the control center. During the sensing operation, the topside engaged the winch to release and retrieve the sensing module. The engagement can be triggered by signals from the sensing platform (which was the current implementation) or by GPS-driven waypoint programming. To perform these tasks, the topside module contained a micro-controller, a GPS unit, and a servo that controls the winch (FIG. 6D). For the micro-controller, an ESP32 LoRA is employed due to its rich connectivity options: LoRA, Wi-Fi, and Bluetooth [https://microcontrollerslab.com/ttgo-lora32-sx1276-oled-board-pinout-getting-started-with-arduino-ide/].

Figure 6F:
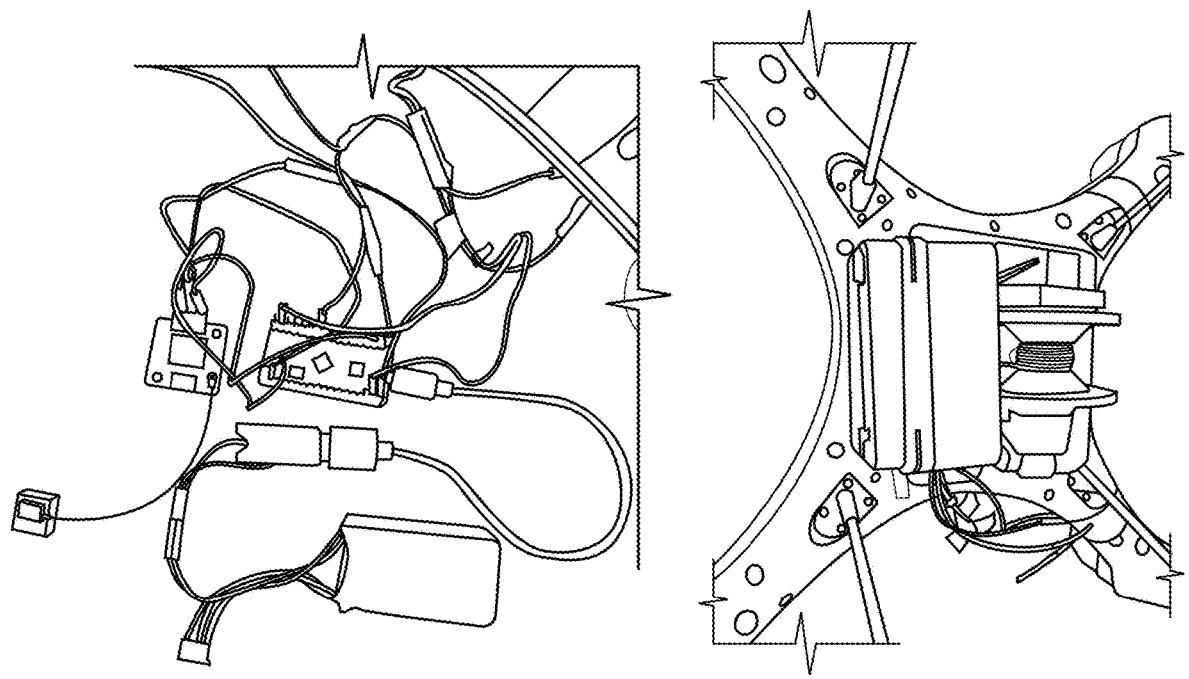

FIG. 6F illustrates the topside electronics and the mounting mechanism of the topside to the drone. The sensing module handled the sensor data acquisitions and quality control (QC). Temperature and DO sensors are included in the module. The controller was an ESP32S which consumed less power than ESP32 LoRA while still supporting multiple analog-to-digital channels and Wi-Fi links.

Figure 6G:
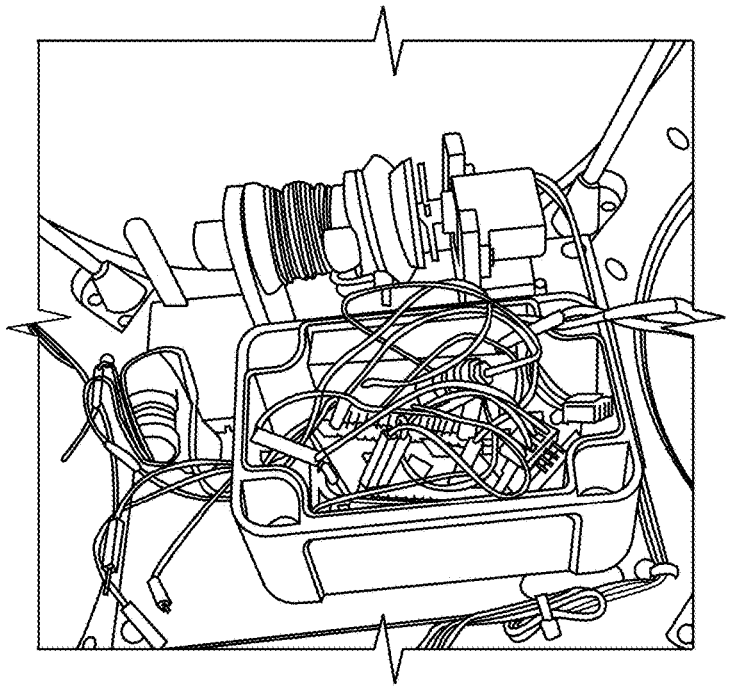

The communications between the topside and the sensing modules were achieved using the ESP-NOW link [https://docs.espressif.com/projects/esp-idf/en/latest/esp32/api-reference/network/esp_now.html]. ESP-NOW is a connectionless communication protocol developed by Espressif to support short packet transmission (up to 250 bytes) between ESP32 boards. This protocol enables multiple devices to talk to each other using the 2.4 GHz RF circuits on the ESP32x boards without the need for the Wi-Fi protocol. Therefore, this protocol was ideal for the link between the topside and sensing modules. The lightweight ESP-NOW link helped to eliminate the need for a physical, electrical connection between the topside and sensing modules and simply the implementation of the winch system. As a result, the winch essentially consisted of a servo that controls the release and retrial of the sensing module using a metal chain (FIG. 6G).

During the sensing operation, the aerial drone was programmed to reach a predefined location over the pond and transition to hovering mode. Once the drone was on location, the sensing module release was triggered (either via a signal from the sensing platform or a pre-determined waypoint). The topside, in turn, engaged the winch to lower the sensor module into the water. The indication that the sensing module was fully submerged in water was that it could no longer communicate with the topside module. The sensing module would then start acquiring DO and temperature data for a pre-determined period of time (i.e., 20 seconds) and store them onboard the sensing module controller. The topside then retrieved the winch following the data acquisition period. Once the sensor module was fully retrieved (the communications between the topside and sensor modules were re-established). The data stored on the sensing module controller was sent via ESP-NOW link to the topside, which then repackaged the data and forwarded on to the control center for processing.

Figure 6H:
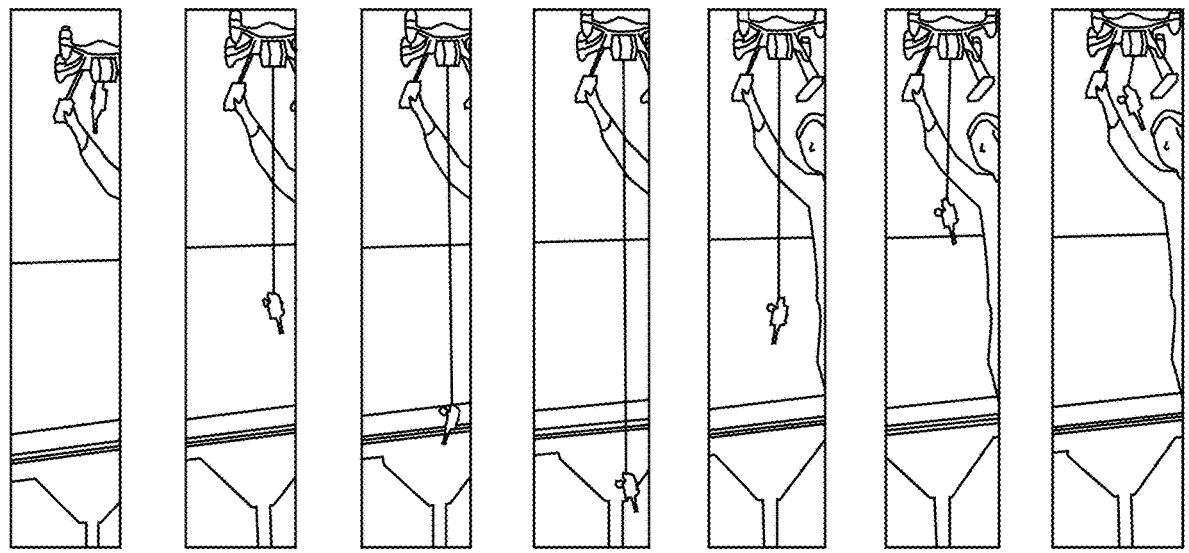

Lab and Field Deployment. The initial test was a static test inside the SAIL lab (FIG. 6H). During the test, the payload was mounted on the drone, and the drone was fixed to the ceiling of the lab and kept idle. During the test, a trigger signal was sent from the drone transmitter to the drone. The signal then triggered the sensing operation: topside engaged the winch to release the payload; the payload then idled for 20 seconds to simulate data acquisition; the topside then retrieved the payload (FIG. 6H). The test was performed in an automated fashion. The communication link from the sensing module to the topside (through ESP-NOW), and from the topside to the control center (via LoRA) was also validated.

While the field tests using the initial prototype validated the basic concept, one issue the study identified during the tests was that, since the payload was connected to the drone body through a string, it was more susceptible to ambient conditions. For example, strong side wind may induce a pendulum effect of the payload, which in turn will impact the flight stability of the drone. The stowing system as described in relation to FIG. 4A-4E was adopted to address this technical issue.

Kresling Kirigami Robotic Extension Design. The study developed a connection arm system that is configured to provide sensing or collection operation, e.g., in strong wind and pendulum effects on the payload based on Kresling kirigami design. Unlike convention winch system, the connection arm provides added rigidity between the payload and the drone body. This helps provide a controllable extension mechanism. For example, the connection arm can extend continuously, stopping at any distance from the drone body as desired and extending in a straight line away from the drone body.

Feasibility Study. The design choice was motivated by several factors. First, the robotic extension for the HAUCS needed the flexibility of support varying extension lengths. Secondly, the folding and unfolding needed to be confined to the same horizontal footprint to avoid interference with other sensors to be integrated into the drone, such as cameras and other environmental sensors. Thirdly, the actuation needed to be supported via the drone flight controller. For this reason, a study was conducted to investigate a Kresling buckling pattern-based design. Furthermore, the study opted for Kirigami instead of Origami. In addition to folding, Kirigami also involves cutting. There is more than simple semantics differences between Kirigami and Origami. For example, Li et al. adopted Kirigami enhancement to prevent wrinkling during continuous folding/unfolding and achieve improved structure reliability [12]. Yasuda uses a similar methodology where he makes small, precise cuts and inserts small holes in areas where continual stresses may lead to creasing and deformation in the mesh [13]. Many others use kirigami to construct self-folding structures [14, 15]. For the HAUCS robotic extension, the study recognized the need for continuous folding/unfolding during the sensing operations. This, therefore, motivated the adoption of a Kirigami-based design.

Kresling Kirigami Prototype Design: The robotic extension employed in the study consisted of multiple Kresling Kirigami sections. Each section includes plates connected with hinges (i.e., Kirigami creases). The torsional loading was realized via the plate rotating at the center axis, driven by a gear system at one end and a ball bearing at the other. The hinges then rotated in conjunction with the rotation of the main body allowing the structure to fold and unfold. The gear and bearing were both mounted on a set of collapsible taped rods.

A Solidworks model of this design was developed to support laboratory evaluations. In the prototype design, the fully extension of one Kirigami section was 82.8 mm, and a folded section measuring a height of 20.2 mm. The diameter of the structure was 85 mm. The central axis was a telescopic rod that could collapse multiple Kirigami sections. Each Kresling Kirigami section could collapse independently to realize a variable-length robotic extension.

In the study, different hinge designs were considered and evaluated. One Kirigami design included hinges that can rotate 180 degrees—an action that is not supported by traditional straight hinge pin. The devised hinge pin included an 'L' shaped attachment joint. This hinge design accomplished two very important requirements, the first, as previously mentioned was the ability to rotate 180 degrees. The hinge has a locking mechanism that can provide rigidity in one direction while compression only in the other direction.

Laboratory Validations: The study constructed small-scale models and subjected them to dynamic force to determine efficacy. During the CAD modeling, "mockups" were first created by utilizing the most simplistic materials (e.g., foam board and bend-straws) to provide physical proof of concept. Once CAD models were established, the components were printed on an 3D printers and assembled. FIGS. 11A-11G illustrate the folding of a single-section structure and a two-section structure. FIGS. 11A-11C illustrate the single-section structure begins in the locked position, with hinges at full extension. Through manual actuation, the structure compresses along the z-axis until it is fully folded. The same process for a two-section is shown in FIGS. 11D-11G.

Load tests were performed on the single-unit model. The tests were conducted by adding water to various containers that were then placed on the top of the unit. Through this test, it was determined that the model would suffer structural failure at 1802 g of applied weight. The test measured structural integrity in relation to the applied load. A value of 2 was given when the structure maintained its integrity with little to no deflection, similar to the elastic region. 1 was given when the structure exhibited signs of deflection consistent with the plastic region. And a zero was given for the point of failure or fracture. Similar tests were conducted on a two-section structure but with the top section folded. Upon completion of these experiments, the model was examined, and while it was structurally weakened, it was not irreparably damaged. It is still able to perform its revolute motion and withstand force, although decidedly lighter weights than previously observed. This can be remedied in the future by exploring alternative materials for both the panels and the hinges.

Figure 12:
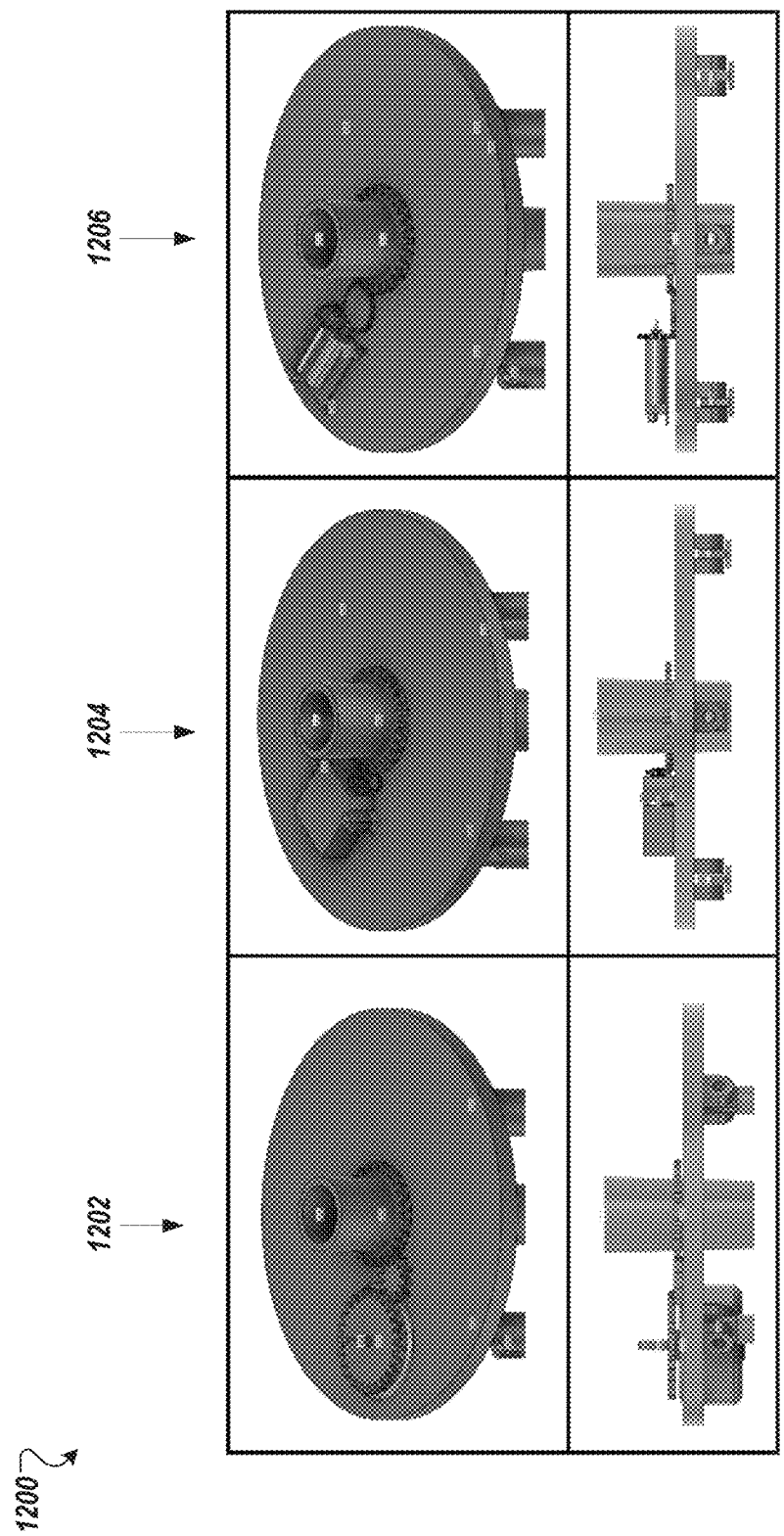
FIGS. 12, 13A, 13B, and 13C are diagrams or photographs, each showing an example connection arm system that may be employed in an example sensing platform system and infrastructure in accordance with an illustrative embodiment.

The study also explored actuation techniques. Actuation may be conducted using a gear system driven by a servo, worm drive, or stepper motor. Models of each of these designs are shown in FIG. 12, but they were not tested beyond CAD modeling. As shown, the actuation gear drive 1200 includes the embodiments of a step motor 1202, micro servo 1204, and linear actuator 1206.

Figure 13B:
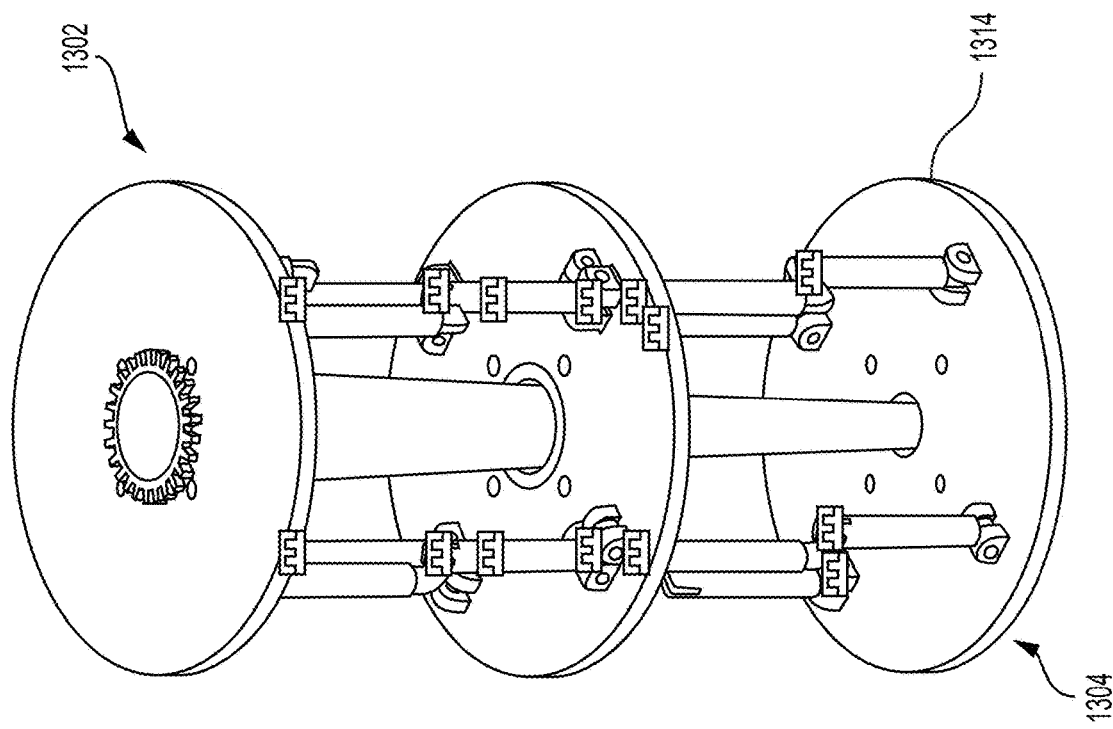
Figure 13A:
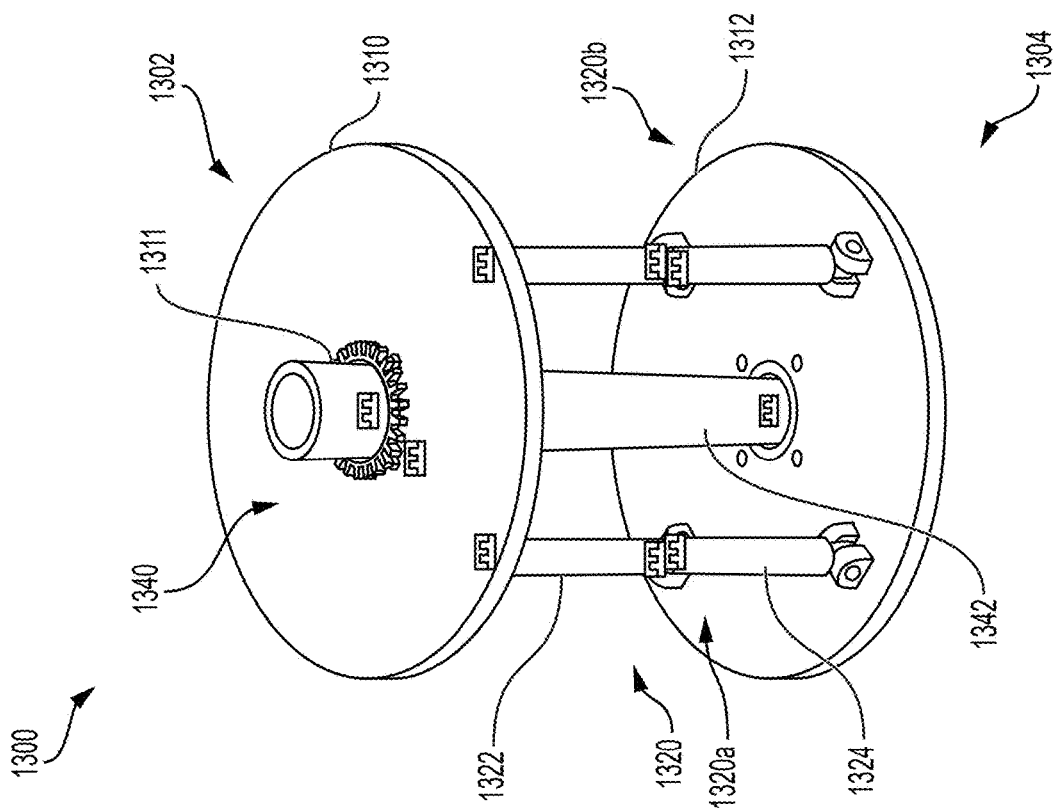
Figure 13C:
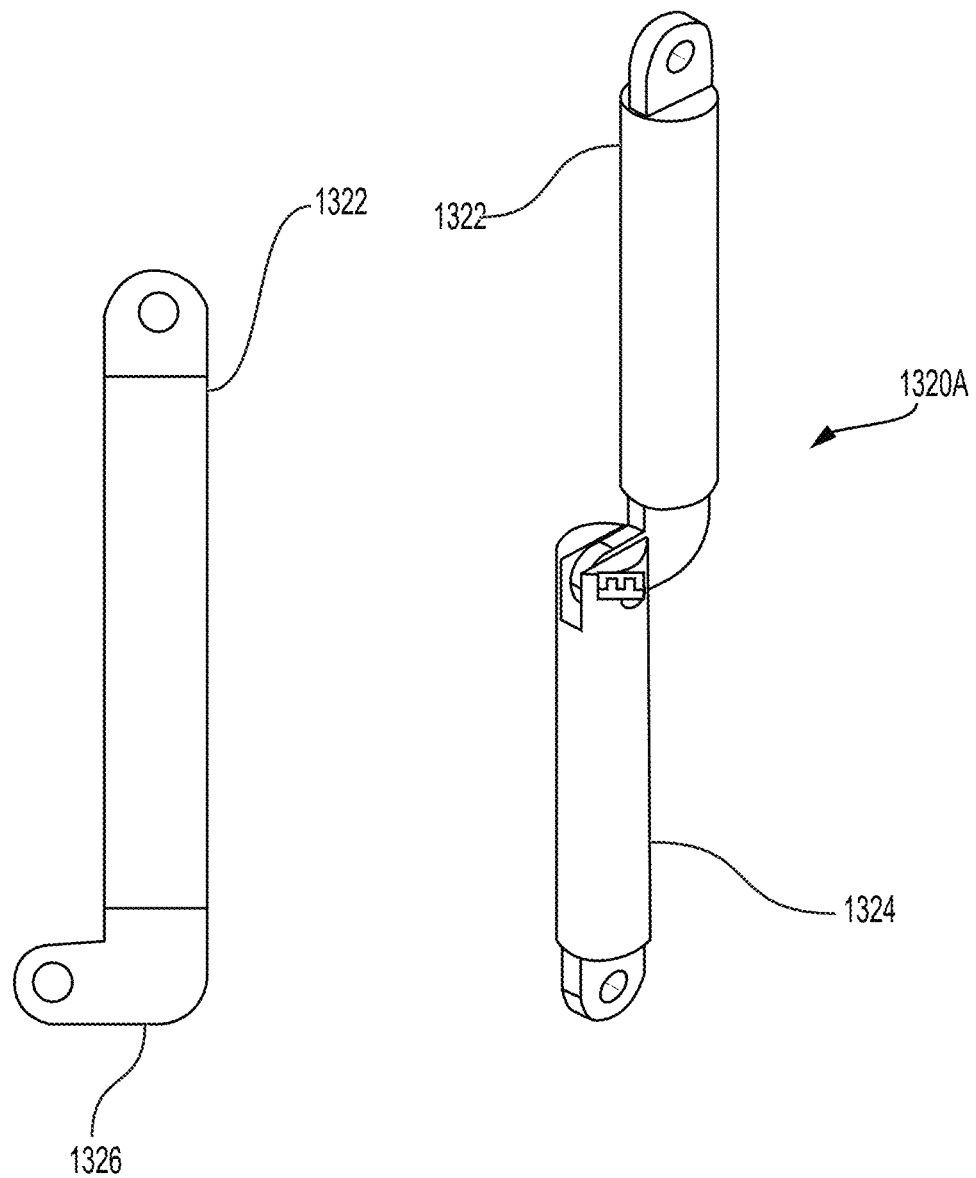

The example shown in FIGS. 13A-13C shows a connection arm 1300 according to one implementation. The connection arm 1300 is configured to connect a mobile platform with a topside module (e.g., a drone or UAAV 112*a*) with a payload (e.g., sensor or collection payload 114*a*).

In the example shown in FIG. 13A, the connection arm 1300 includes a first end 1302, a second end 1304, a first plate 1310, a second plate 1312, four sets 1320 of elongated links, and a telescoping rod assembly 1340. The first end 1304 is configured to operatively couple to a moving platform. The second end 1306 is configured to removably couple to a sensing module. The first and second plates (1310, 1312) are separated and spaced apart from each other. The example shown in FIG. 13B includes a third plate 1314, which operates in a similar manner to the descriptions of FIG. 13A.

The sets 1320 of elongated links include at least a first set 1320*a* of links and a second set 1320*b* of links. The first set 1320*a* includes a first link 1322 hingeably connected to the first plate 1310 and a second link 1324. The second link 1324 is hingably connected to the second plate 1312.

The example shown in FIG. 13C provides more details on the first set 1320*a* of first link 1322 and second link 1324. In particular, the first link 1322 includes a L-shaped region 1326 at the connection point with the second link 1324 to facilitate rotation in one direction. The first link 1322, and second link 1324 can rotate up to 180 degrees with respect to each other.

The telescoping rod assembly 1340 includes a first telescoping section 1342 (where the FIG. 13B embodiment also includes a second telescoping section 1344). The first telescoping section 1342 is slidably coupled to the first plate 1310, where the first telescoping section 1342 extends through a center hole 1311 in the first plate 1310 to connect to the second plate 1312.

In use, rotation of the telescoping rod assembly 1340 causes the second plate 1312 to rotate to move the second plate 1312 between a stowed configuration and a deployed configuration. The distance between the first plate 1310 and the second plate 1312 is greater in the deployed configuration than it is in the stowed configuration. When moving between configurations, as the rotation occurs, the first and second links (1322, 1324) rotate with respect to each other and move the second plate 1312.

While the example of FIG. 13B shows three plates, in other implementations, more than three plates (with corresponding sets of links) may be used (e.g., four, six, eight, or ten plates corresponding to the distance of sampling required). While the examples of FIGS. 13A-B show four sets of links; in other implementations, the connection arm may have as few as two sets of links or a number greater than four sets of links (e.g., six or eight sets of links).

By use of the connection arm 1300, a mobile platform (e.g., a drone with a topside module) can deploy a payload with more stability and accuracy. Wind conditions are less likely to affect the overall system, and exact sampling distances can be achieved.

DISCUSSION

Challenges in Aqualture Farming. Precision agriculture (PA) is the application of robotic field machines and information technology in agriculture, and it is playing an increasingly important role in farm production. PA-related advanced technologies such as the internet of things (IoT), Robotics, and Artificial Intelligence (AI) have been an active research topic and have seen robust growth [1, 2, 3]. Importantly, research results in the area of CPS have been successfully adopted in many sectors in the agriculture industry. A BI Intelligence survey (https://artillry.co/wp-content/uploads/2019/08/Business-Insider-IoT-101.pdf) expects the adoption of IoT devices in the agriculture industry to reach 75 million in 2020, growing 20% annually. The global smart agriculture market size is expected to triple by 2025, growing from $5 billion in 2016 to over $15 billion.

However, one important sector of agriculture that has been left behind is aquaculture. Aquaculture is farming in an aquatic environment. As an agricultural practice, aquaculture is characterized by considerable diversity in its habitats, methods, and species. The species range from "livestock" (e.g., fish, mollusks, and crustaceans) to plants (e.g., microalgae, macroalgae, and vascular plants). The systems employed include earthen ponds, tanks, or open water (nearshore or offshore), depending on the habitat where production is occurring. Pond and tank systems are generally land-based, and net pens or bottom culture are in open water. Underpinning all of these are the energy systems powering the farm operations.

Worldwide, aquaculture plays an essential role in food security in the seafood sector, filling the need and demand gap due to stagnant capture fisheries output. The transition from fisheries to aquaculture has been growing at an average rate of >6% annually. Since 2014, more farmed seafood than wild-caught seafood has been consumed globally, with more than half of all seafood coming from farms [1]. It is also important to emphasize that, compared with other farmed proteins (e.g., chicken and beef), seafood has the highest resource efficiency and lowest feed conversion ratio (i.e., most efficient in converting feed to animal proteins). Aquaculture produces lower greenhouse gas emissions than other types of farming [2]. (See graphic (a) below, showing the high resource efficiency of fish compared with other farmed proteins. Farmed fish are less resource-intensive overall than other common animal-based protein products and consume less water for production than pork and beef in many cases [3] [4].

Regrettably, only 1% of aquaculture products are produced here in the US, and, as a result, over 90% of US seafood is imported. The current state of US aquaculture can be best summarized in two negative ways: The US fish farming operations are labor-intensive and resource-inefficient. Although ideally situated for the infusion of new advances in Artificial Intelligence (AI), robotics, and the Internet of Things (IoT), their adoption in aquaculture has been very limited in the US. Even with vast, abundant coastal zones and ranking third in the world in total renewable water resources [5], the US suffers a $14 Billion annual seafood trade deficit and ranks seventh among the G20 nations in aquaculture productions. See graphic (b) below, displaying aquaculture production in 2017 among the G20 countries. China (66.14 Mts) and the US (0.47 Mts) are highlighted in red [6]. Therefore, there is a strong urgency for a coherent effort to realize the future of aquaculture in the US through robotics, AI, and CPS.

In aquaculture fish farming, the management of water quality, particularly dissolved oxygen (DO), is critically important for successful operation. DO depletion is a leading cause of fish mortality on farms. Catastrophic loss can occur within hours if ponds are not appropriately managed. The current management practice on pond-based farms is the use of human operators who drive trucks or other all-terrain vehicles throughout the day, but especially at night, to sample and monitor DO in each pond. The associated labor and equipment costs limit the scope and frequency of such sampling since dozens of ponds must be managed by each sensor-equipped truck. Large farms require multiple drivers and sampling instruments to attain the required monitoring frequency for proper management. The level of resolution that this approach can achieve on any pond is generally restricted to a single near-shore measurement at a point on the pond with a well-maintained roadbed. On large ponds (e.g., 2 to 8 hectares), this may result in a failure to promptly identify localized water quality problems that can ultimately affect a large proportion of the stock. Even though readings should be taken hourly on each pond, very large farms (>400 hectares) with hundreds of ponds may only be able to take readings at much lower frequencies due to the labor and equipment costs of operating large fleets of monitoring vehicles. Measurements of additional water quality parameters cannot be performed due to the demanding schedules required of drivers to achieve the minimum frequency for DO management. Furthermore, with the current practice, operators have a very limited window of time (e.g., less than an hour in the middle of the night) to react to potential oxygen depletion, increasing the potential likelihood of catastrophic events. The response (e.g., putting emergency aeration equipment in a pond) takes time away from achieving DO measurement frequencies.

The Hybrid Aerial/Underwater RobotiC System (HAUCS) framework can mitigate the aforementioned issues by providing automated, high-density monitoring of key environmental metrics of each aquaculture pond on a farm using relatively inexpensive robotic sensing platforms. One important aspect of the HAUCS sensing platform is a robust winch assembly that can stow and automatically deploys with the winch operation.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to the arrangement of steps or operational flow, plain meaning derived from grammatical organization or punctuation, the number or type of embodiments described in the specification.

It will be readily understood that the components of the embodiments, as generally described herein and illustrated in the appended figures, could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout the specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

As used in this document, the singular form "a," "an," and "the" include plural references unless the context clearly dictates otherwise. Unless defined otherwise, all technical and scientific terms used herein have the same meanings as commonly understood by one of ordinary skill in the art. As used in this document, the term "comprising" means "including, but not limited to."

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

It is understood that throughout this specification, the identifiers "first," "second," "third," "fourth," "fifth," "sixth," and such are used solely to aid in distinguishing the various components and steps of the disclosed subject matter. The identifiers "first," "second," "third," "fourth," "fifth," "sixth," and such are not intended to imply any particular order, sequence, amount, preference, or importance to the components or steps modified by these terms.

All references cited and discussed in this specification are incorporated herein by reference in their entirety and to the same extent as if each reference was individually incorporated by reference.

REFERENCES

[1] Y. Li, W. Liu, Y. Deng, W. Hong and H. Yu, "Miuraori enabled stretchable circuit boards," Nature Partner Journals-Flexible Electronics, 2021.
[2] Z. Song, Studies of Origami and Kirigami and Their Applications, Arizona State University, 2016.
[3] M. Wooten, "UGA researchers unfold advances in cardiac catheters," UGA Research, 28 Jul. 2016.

[4] "From Origami to a Prototype Stent," MDDI, 27 Apr. 2012.
[5] K. Miura and T. Tachi, "Synthesis of rigid-foldable cylindrical polyhedra," Gmuend, Austria, 2010.
[6] A. A. Deleo, J. E. O'Neil, H. Yasuda, J. Yang and M. Salviato, "Composite Origami: Foldable Structures Based on Tachi-Miura-Polyhedron Origami Technique," 2018.
[7] S. A. Zirbel, B. P. Trease, S. P. Magleby and L. L. Howell, "Deployment Methods for an Origami-Inspired Rigid-Foldable Array," in 40th Aerospace Mechanisms Symposium, Greenbelt, Maryland, 2014.
[8] T. Tachi, "Rigid-Foldable Thick Origami," 2011.
[9] T. Tachi, "Geometric Considerations for the Design of Rigid Origami Structures," in International Association for Shell and Spatial Structures, Shanghai, China, 2010.
[10] M. Schenk and S. D. Guest, "Geometry of Miura-folded metamaterials," PNAS, vol. 10, no. 9, pp. 3276-3281, 2013.
[11] H. Yasuda, T. Yein, T. Tachi, K. Miura and M. Taya, "Folding behaviour of Tachi-Miura polyhedron bellows," Royal Society, pp. 1-18, 2013.
[12] Y. Nishiyama, "Miura Folding: Applying Origami to Space Exploration," International Journal of Pure and Applied Mathematics, vol. 79, no. 2, pp. 269-279, 2012.
[13] J. J. Park, P. Won and S. H. Ko, "Review on Hierarchical Origami and Kirigami Structure for Engineering Applications," International Journal of Precision Engineering and Manufacturing-Green Technology, vol. 6, pp. 147-161, 2019.
[14] S. Chen, J. Chen, X. Zhang, Z.-Y. Li and J. Li, "Kirigami/origami: unfolding the new regime of advanced 3D microfabrication/nanofabrication with "folding"," CIOMP, vol. 9, no. 75, pp. 1-19, 2020.
[15] T. van Manen, S. Janbaz, M. Ganjian and A. A. Zadpoor, "Kirigami-enabled self-folding origami," Materials Today, vol. 32, pp. 59-67, 2020.
[16] A. Reid, F. Lechenault, S. Rica and M. Adda-Bedia, "Geometry and design of origami bellows with tunable response," 2016.
[17] K. Saito, A. Tsukahara and Y. Okabe, "Designing of self-deploying origami structures using geometrically misaligned crease patterns," Royal Society, pp. 1-16, 2015.
[18] N. Turner, B. Goodwine and M. Sen, "A review of origami applications in mechanical engineering," Institution of Mechanical Engineers, vol. 230, pp. 2345-2362, 2016.
[19] S. J. Kim, D. Y. Lee, G. P. Jung, K. J. Cho, "An origami-inspired, self-locking robotic arm that can be folded flat," Science Robotics, vol 3, pp. 1-10

The invention claimed is:

1. A method for operating a system for water sampling or collection at a wastewater site, a body of water, or an aquaculture farm, the method comprising:
positioning a sensing platform over or next to a water body medium in a sampling or collecting operation, wherein the sensing platform comprises an elongated or elongate-able structure that can extend or hinge-ably move to a first position to put a remote sensor connected to the sensing platform by the elongated or elongate-able structure into the water body medium for water collection or sampling;
transmitting, over a wireless communication channel, a wireless command signal from a first controller located on the sensing platform to a second controller located in the remote sensor, wherein the second controller located in the remote sensor is fully autonomous and is not electrically connected by wire to the first controller;
executing, at the second controller, a set of instructions for a sensing or collection protocol to perform a sensing or collection operation at the remote sensor;
concurrent with the execution of the set of instructions for the sensing or collection protocol, adjusting at the sensing platform the remote sensor from the first position to a plurality of positions, including a second position and a third position, each corresponding to a different water depth to perform the sensing or collection operation of the remote sensor at the respective water depth;
wherein the sensing or collection protocol for the sampling or collecting operation is synchronized to the plurality of positions corresponding to the different water depths.

2. The method of claim 1, wherein the sensing platform is configured to adjust the remote sensor to the plurality of positions at pre-defined time intervals defined in the set of instructions for the sensing or collection protocol, and recordation of measurements by the second controller of the remote sensor is performed according to the pre-defined time intervals, wherein initialization of the pre-defined time intervals is based on the wireless command signal.

3. The method of claim 1,
wherein the sensing platform comprises an aero-amphibious vehicle comprising a winch assembly and the remote sensor, wherein the aero-amphibious vehicle is configured to perform the sensing or collection operation at a plurality of locations, and wherein the winch assembly is configured to i) release the remote sensor from a stowed position to a deployed position and ii) draw the remote sensor from the deployed position to the stowed position in between each of the sensing or collection operations at the plurality of locations.

4. The method of claim 3, wherein the release of the remote sensor from a stowed position to a deployed position and the draw of the remote sensor from the deployed position to the stowed position is performed by:
an actuation of the winch assembly to extend or retract a tether connecting to the remote sensor, the winch assembly comprising a retaining arm subassembly (i) through which the tether connects to the remote sensor and (ii) that which moves (a) from a stowed position to a deployed position when the winch assembly extends the tether to release the remote sensor from the retaining arm subassembly and (b) from the deployed position to the stowed position when the winch assembly retracts the tether to engage the remote sensor with the retaining arm subassembly.

5. The method of claim 1, wherein the sensing platform comprises a terrestrial vehicle, an aero-amphibious vehicle, a buoy, or a fixed location system.

6. The method of claim 1, wherein the sensing platform includes
a winch payload deployment assembly apparatus comprising:
a winch chassis comprising a spool, an actuator, and a coupling between the spool and the actuator;
a tether configured to be wound around the spool, the tether being fixably attached to the winch chassis, at a first end, a payload at a second end; and
a bracket coupled to the winch chassis, wherein the bracket is configured to move between a stowed position to a deployed position when the spool actuates from an initial position to an extended position to release the payload abutting against the bracket, and wherein the bracket is configured to move from the deployed position to the stowed position when the spool actuates from the extended position to the initial position to draw the payload to abut against the bracket.

7. The method of claim 6, wherein the bracket is biased by a torsional spring towards the deployed position.

8. The method of claim 6, wherein the bracket comprises an angled body having (i) a retaining portion configured to abut against a spool plate and (ii) a payload portion configured to support the payload when the bracket is in the stowed position, wherein the retaining portion abut against the spool plate when the spool is in the initial position.

9. The method of claim 6, wherein the actuator actuates to unwound the spool from the initial position, an extension of the tether releasing the payload abutting against the bracket to allow the bracket to move from the stowed position to the deployed position.

10. The method of claim 6, wherein the winch payload deployment assembly apparatus includes a second actuator to actuate the bracket, and wherein the apparatus includes a contact sensor configured to detect when the bracket is in the stowed position, the contact sensor providing a signal to control the actuation of the spool.

11. The winch payload deployment assembly apparatus of claim 6, wherein the winch chassis comprises a first side wall and a second side wall to fixably retain the spool, the actuator, and the bracket and couple the winch payload deployment assembly apparatus to a vehicle.

12. The method of claim 1 comprising: a robotic sensing package, comprising:
an undercarriage substrate disposed on a moving platform; and
a connection arm comprising:
a first end operatively coupled to the moving platform;
a second end removably coupled to a sensing module;
a plurality of plates separated and spaced apart from each other, including a first plate, and a second plate; and
a plurality of sets of elongated links, including a first set of links and a second set of links, wherein the first set of links include a first link hingeably connected to the first plate and a second link, the second link being hingably connected to the second plate,
wherein each of the first link and second link is rotatable to move the second plate between a stowed configuration and a deployed configuration.

13. The method of claim 12, wherein the connection arm further comprises:
a telescoping rod assembly having at least one telescoping section that is slidably coupled to the first plate, the at least one telescoping section extending through the first plate to connect to the second plate through a center hole in the first plate,
wherein rotation of the telescoping rod assembly causes at least the second plate to rotate to move the second plate between the stowed configuration and the deployed configuration.

14. The method of claim 12, wherein the connection arm further comprises:
a telescoping rod assembly having a plurality of sections, including a first section and a second section, wherein the first section is slidably coupled to the first plate, wherein the second section is slidably coupled to the second plate, and wherein rotation of the telescoping rod assembly causes the first plate and the second plate to rotate to move the second plate between the stowed configuration and the deployed configuration.

15. A method of claim 1 further comprising:
remotely gathering samples from a liquid medium or making a direct measurement of the liquid medium
deploying a mobile vehicle platform to a predefined geographic location over the liquid medium, wherein the mobile vehicle platform includes an undercarriage substrate and a connection arm operatively coupled to the undercarriage substrate of the vehicle, the connection arm comprising:
a first end operatively coupled to the moving platform;
a second end removably coupled to a sensing module;
a plurality of plates separated and spaced apart from each other, including a first plate, a second plate, and a third plate;
a plurality of telescoping rod sections operatively coupled to a center hole of each plate; and
a plurality of sets of elongated links, including a first set of links and a second set of links, wherein the first set of links include a first link hingeably connected to the first plate and a second link, the second link being hingably connected to the second plate,
wherein each of the first link and second link is rotatable to move the second plate between a stowed configuration and a deployed configuration,
activating an actuator located on the mobile vehicle platform, wherein the activating causes an output of the actuator to drive the rotation of at least one of the plates or the telescoping rod sections, so to place a sensor module or sampling container located at the end of the connection arm into the liquid medium.

16. The method of claim 15, further comprising:
detecting a sensing signal to start a sampling operation, wherein the sampling operation continues for a predetermined period of time;
stopping a motor as the actuator for a duration of the sampling operation to collect sensor data; and
starting the motor in an opposite direction so to remove the sensor module from the liquid medium and collapse the connection arm towards the stowed configuration.

17. The method of claim 16, further comprising:
sending the sensor data from the sensing module to the mobile vehicle platform; and
relaying the sensor data from the mobile vehicle platform to a central control center.

18. The method of claim 15, wherein the liquid medium is a body of water.

19. The method of claim 15, wherein the gathered samples or direct measurements include dissolved oxygen, pressure, and/or temperature data.

20. The method of claim 15, wherein the activating an actuator occurs upon the mobile vehicle platform reaching a predefined GPS location.

* * * * *